(12) United States Patent
Utsumi et al.

(10) Patent No.: US 9,017,919 B2
(45) Date of Patent: Apr. 28, 2015

(54) RESIST COMPOSITION, METHOD OF FORMING RESIST PATTERN, NOVEL COMPOUND AND ACID GENERATOR

(75) Inventors: Yoshiyuki Utsumi, Kawasaki (JP); Akiya Kawaue, Kawasaki (JP); Yoshitaka Komuro, Kawasaki (JP); Kenichiro Miyashita, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 234 days.

(21) Appl. No.: 13/282,920

(22) Filed: Oct. 27, 2011

(65) Prior Publication Data

US 2012/0107744 A1    May 3, 2012

(30) Foreign Application Priority Data

Oct. 29, 2010  (JP) ................. 2010-244298

(51) Int. Cl.
| | | |
|---|---|---|
| G03F 7/004 | (2006.01) | |
| C07D 307/00 | (2006.01) | |
| C07D 327/02 | (2006.01) | |
| C07D 327/04 | (2006.01) | |
| C07D 493/18 | (2006.01) | |
| C07D 497/18 | (2006.01) | |
| G03F 7/039 | (2006.01) | |

(52) U.S. Cl.
CPC ............ *G03F 7/0045* (2013.01); *C07D 307/00* (2013.01); *C07D 327/02* (2013.01); *C07D 327/04* (2013.01); *C07D 493/18* (2013.01); *C07D 497/18* (2013.01); *G03F 7/0046* (2013.01); *G03F 7/0397* (2013.01); *Y10S 430/115* (2013.01)

(58) Field of Classification Search
None
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,444,397 B2 | 9/2002 | Hada et al. | |
| 6,949,325 B2 | 9/2005 | Li et al. | |
| 7,074,543 B2 | 7/2006 | Iwai et al. | |
| 2004/0185378 A1 | 9/2004 | Kodama et al. | |
| 2007/0148592 A1 | 6/2007 | Wada et al. | |
| 2008/0187860 A1 | 8/2008 | Tsubaki et al. | |
| 2010/0239978 A1* | 9/2010 | Wada et al. | 430/270.1 |
| 2010/0304294 A1* | 12/2010 | Ichikawa et al. | 430/270.1 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2004-277303 | 10/2004 |
| JP | A-2005-336452 | 12/2005 |
| JP | A-2006-259582 | 9/2006 |
| JP | A-2006-317803 | 11/2006 |
| JP | A-2007-178848 | 7/2007 |
| JP | A-2008-292975 | 12/2008 |
| JP | A-2010-061043 | 3/2010 |
| WO | WO 2004/074242 A2 | 9/2004 |

OTHER PUBLICATIONS

English Translation of JP2004277303.*
Notice of Allowance mailed May 20, 2014 in Japanese Patent Application No. 2010-244298.

\* cited by examiner

*Primary Examiner* — Martin Angebranndt
*Assistant Examiner* — Anna Malloy
(74) *Attorney, Agent, or Firm* — Knobbe Martens Olson & Bear LLP

(57) ABSTRACT

A resist composition containing a base component (A) which exhibits changed solubility in a developing solution under the action of acid, and an acid generator component (B) which generates acid upon exposure, wherein the acid generator component (B) includes an acid generator (B1) having a group represented by general formula (b1-1) shown below in the cation moiety.

[Chemical Formula 1]

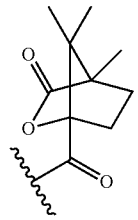

(b1-1)

9 Claims, No Drawings

RESIST COMPOSITION, METHOD OF FORMING RESIST PATTERN, NOVEL COMPOUND AND ACID GENERATOR

TECHNICAL FIELD

The present invention relates to a resist composition, a method of forming a resist pattern using the resist composition, a novel compound that is useful as an acid generator for the resist composition, and an acid generator.

Priority is claimed on Japanese Patent Application No. 2010-244298, filed Oct. 29, 2010, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (and increasing the energy) of the exposure light source. Conventionally, ultraviolet radiation typified by g-line and i-line radiation has been used, but nowadays KrF excimer lasers and ArF excimer lasers are starting to be introduced in the mass production of semiconductor elements. Furthermore, research is also being conducted into lithography techniques that use an exposure light source having a shorter wavelength (and a higher energy level) than these excimer lasers, such as $F_2$ excimer lasers, electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base component which exhibits changed solubility in a developing solution under the action of acid and an acid generator which generates acid upon exposure.

For example, in the case where the aforementioned developing solution is an alkali developing solution (namely, an alkali developing process), a chemically amplified positive resist containing, as a base component (base resin), a resin which exhibits increased solubility in an alkali developing solution under the action of acid, and an acid generator is typically used. If the resist film formed using the resist composition is selectively exposed during formation of a resist pattern, then within the exposed portions, acid is generated from the acid generator component, and the action of this acid causes an increase in the solubility of the resin component in an alkali developing solution, making the exposed portions soluble in the alkali developing solution. The unexposed portions remain as a pattern, resulting in formation of a positive-type pattern. The aforementioned base resin uses a resin for which the polarity increases under the action of acid, resulting in an increase in the solubility of the resin in an alkali developing solution, but a decrease in the solubility of the resin within organic solvents. Accordingly, if a process that uses a developing solution containing an organic solvent (an organic developing solution) is employed (hereinafter also referred to as a solvent developing process or negative-type developing process) instead of the alkali developing process, then within the exposed portions, the solubility in the organic developing solution decreases relatively, meaning that in the solvent developing process, the unexposed portions of the resist film are dissolved in the organic developing solution and removed, whereas the exposed portions remain as a pattern, resulting in formation of a negative-type resist pattern. Patent Document 1 proposes a negative-type developing process.

Currently, resins and the like that contain structural units derived from (meth)acrylate esters within the main chain (acrylic resins) are now widely used as base resins for resist compositions that use ArF excimer laser lithography or the like, as they exhibit excellent transparency in the vicinity of 193 nm (for example, see Patent Document 2).

Further, all manner of acid generators have been proposed for use in chemically amplified resist compositions, and known acid generators include onium salt acid generators, oxime sulfonate acid generators, diazomethane acid generators, nitrobenzylsulfonate acid generators, iminosulfonate acid generators, and disulfone acid generators. Among these, as the onium salt acid generators, iodonium salts having an iodonium ion as the cation and sulfonium salts having a sulfonium ion as the cation are conventionally used. In recent years, acid generators having a sulfonium salt with a lactone structure have been proposed (for example, see Patent Documents 3 and 4).

PRIOR ART DOCUMENTS

Patent Documents

[Patent Document 1] JP-2008-292975-A
[Patent Document 2] JP-2003-241385-A
[Patent Document 3] JP-2007-178848-A
[Patent Document 4] JP-2010-61043-A

DISCLOSURE OF INVENTION

Problems to be Solved by the Invention

With the expectation of further progress in lithography techniques and ongoing reductions in the size of resist patterns, there are growing demands for further improvements in a variety of lithography properties for resist materials. Examples of lithography properties for which improvements are sought include the line width roughness (LWR), the mask error enhancement factor (MEEF) and the EL margin.

However, in those cases where conventional acid generators such as those disclosed in Patent Documents 3 and 4 are used, the lithography properties of the resulting resist patterns still leave room for improvement.

The present invention takes the above circumstances into consideration, with an object of providing a resist composition, a method of forming a resist pattern using the resist composition, a novel compound that is useful as an acid generator for the resist composition, and an acid generator.

Means to Solve the Problems

In order to achieve the above object, the present invention adopts the aspects described below.

Namely, a first aspect of the present invention is a resist composition containing a base component (A) which exhibits changed solubility in a developing solution under the action of acid, and an acid generator component (B) which generates acid upon exposure, wherein the acid generator component (B) includes an acid generator (B1) having a group represented by general formula (b1-1) shown below in the cation moiety.

[Chemical Formula 1]

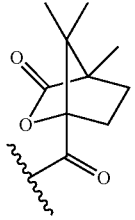

(b1-1)

A second aspect of the present invention is a method of forming a resist pattern, the method including: forming a resist film on a substrate using the resist composition of the first aspect, conducting exposure of the resist film, and developing the resist film to form a resist pattern.

A third aspect of the present invention is a compound represented by general formula (b1-2) shown below.

[Chemical Formula 2]

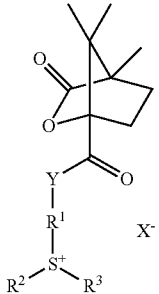

(b1-2)

In the formula, Y represents a divalent linking group, $R^1$ represents an arylene group which may have a substituent, each of $R^2$ and $R^3$ independently represents an organic group, $R^2$ and $R^3$ may be bonded to each other to form a ring with the sulfur atom in the formula, and $X^-$ represents a counter anion.

A fourth aspect of the present invention is an acid generator formed from the compound of the third aspect.

In the present description and claims, the term "aliphatic" is a relative concept used in relation to the term "aromatic", and defines a group or compound or the like that has no aromaticity.

The term "alkyl group" includes linear, branched and cyclic monovalent saturated hydrocarbons, unless otherwise specified.

The term "alkylene group" includes linear, branched and cyclic divalent saturated hydrocarbons, unless otherwise specified. The same applies for the alkyl group within an alkoxy group.

A "halogenated alkyl group" is a group in which some or all of the hydrogen atoms of an alkyl group are substituted with halogen atoms. Examples of halogen atoms include fluorine atoms, chlorine atoms, bromine atoms and iodine atoms.

A "fluorinated alkyl group" or a "fluorinated alkylene group" is a group in which some or all of the hydrogen atoms of an alkyl group or an alkylene group have been substituted with fluorine atoms.

The term "structural unit" refers to a monomer unit that contributes to the formation of a polymeric compound (resin, polymer, copolymer).

The term "acrylate ester" describes a compound in which the hydrogen atom at the carboxyl group terminal of acrylic acid ($CH_2=CH-COOH$) has been substituted with an organic group.

A "structural unit derived from an acrylate ester" refers to a structural unit that is formed by the cleavage of the ethylenic double bond of an acrylate ester.

In an "acrylate ester that may have an atom other than a hydrogen atom or a substituent bonded to the carbon atom on the α-position", examples of the atom other than a hydrogen atom include halogen atoms, whereas examples of the substituent include alkyl groups of 1 to 5 carbon atoms, halogenated alkyl groups of 1 to 5 carbon atoms and hydroxyalkyl groups. Examples of the halogen atoms include fluorine atoms, chlorine atoms, bromine atoms and iodine atoms.

The "α-position (carbon atom on the α-position) of a structural unit derived from an acrylate ester" refers to the carbon atom bonded to the carbonyl group, unless specified otherwise.

Specific examples of the alkyl groups of 1 to 5 carbon atoms for the substituent that may be bonded to the carbon atom on the α-position include linear or branched alkyl groups such as a methyl group, ethyl group, propyl group, isopropyl group, n-butyl group, isobutyl group, tert-butyl group, pentyl group, isopentyl group or neopentyl group.

Further, specific examples of the halogenated alkyl groups of 1 to 5 carbon atoms for the substituent include groups in which some or all of the hydrogen atoms within an aforementioned "alkyl group of 1 to 5 carbon atoms for the substituent" are substituted with halogen atoms. Examples of these halogen atoms include fluorine atoms, chlorine atoms, bromine atoms and iodine atoms, of which fluorine atoms are particularly desirable.

Specific examples the hydroxyalkyl groups for the substituent include groups in which some or all of the hydrogen atoms within an aforementioned "alkyl group of 1 to 5 carbon atoms for the substituent" are substituted with hydroxyl groups.

In the present invention, a hydrogen atom, an alkyl group of 1 to 5 carbon atoms or a halogenated alkyl group of 1 to 5 carbon atoms is preferably bonded to the carbon atom on the α-position, a hydrogen atom, an alkyl group of 1 to 5 carbon atoms or a fluorinated alkyl group of 1 to 5 carbon atoms is more preferred, and from the viewpoint of industrial availability, a hydrogen atom or a methyl group is the most desirable.

The term "exposure" is used as a general concept that includes irradiation with any form of radiation, including an ArF excimer laser, KrF excimer laser, $F_2$ excimer laser, EUV (extreme ultraviolet radiation), VUV (vacuum ultraviolet radiation), EB (electron beam), X-ray or soft X-ray.

Effect of the Invention

The present invention is able to provide a resist composition having favorable lithography properties, a method of forming a resist pattern using the resist composition, a novel compound that is useful as an acid generator for the resist composition, and an acid generator.

DETAILED DESCRIPTION OF THE INVENTION

<<Resist Composition>>

The resist composition of the first aspect of the present invention includes a base component (A) (hereinafter referred to as "component (A)") which exhibits changed solubility in a developing solution under the action of acid, and an acid generator component (B) (hereinafter referred to as "component (B)") which generates acid upon exposure.

When the resist film that is formed using the resist composition is subjected to selective exposure during resist pattern formation, acid is generated from the component (B), and the solubility of the component (A) in a developing solution is changed by the action of the generated acid. As a result, because the solubility in the developing solution of the exposed portions of the resist film changes, whereas the solubility in the developing solution of the unexposed portions does not change, subsequent developing can be used to form a resist pattern, by dissolving and removing either the exposed portions in the case of a positive-type pattern, or the unexposed portions in the case of a negative-type pattern.

The resist composition of the present invention may be either a negative-type resist composition or a positive-type resist composition.

In this description, a resist composition in which the exposed portions are dissolved and removed to form a positive-type pattern is referred to as a "positive resist composition", whereas a resist composition in which the unexposed portions are dissolved and removed to form a negative-type pattern is referred to as a "negative resist composition".

<Component (A)>

As the component (A), either a single organic compound or a mixture of two or more organic compounds that are typically used as the base component for chemically amplified resists may be used.

In the present invention, the term "base component" refers to an organic compound capable of forming a film, and is preferably an organic compound having a molecular weight of 500 or more. Ensuring that the organic compound has a molecular weight of 500 or more improves the film-forming ability, and facilitates the formation of nano level resist patterns.

The "organic compounds having a molecular weight of 500 or more" that can be used as the base component may be broadly classified into non-polymers and polymers.

In general, compounds which have a molecular weight of at least 500 but less than 4,000 may be used as non-polymers. Hereinafter, a non-polymer having a molecular weight of at least 500 but less than 4,000 is referred to as a "low molecular weight compound".

In terms of the polymers, compounds which have a molecular weight of 1,000 or more may be used. Hereinafter, a polymer having a molecular weight of 1,000 or more is referred to as a "polymeric compound". In the case of a polymeric compound, the "molecular weight" refers to the polystyrene-equivalent weight-average molecular weight determined by gel permeation chromatography (GPC). Hereinafter, a polymeric compound is frequently referred to as simply a "resin".

Either a resin component that exhibits changed solubility in a developing solution under the action of acid, or a low molecular weight compound that exhibits changed solubility in a developing solution under the action of acid may be used as the component (A).

In those cases where the resist composition of the present invention is a "negative resist composition for an alkali developing process" which forms a negative-type pattern in an alkali developing process, a base component that is soluble in the alkali developing solution is used as the component (A), and a cross-linking agent is also added to the composition.

In this negative resist composition for an alkali developing process, when acid is generated from the component (B) upon exposure, the action of the acid causes cross-linking between the base component and the cross-linking agent, and the cross-linked portions become insoluble in an alkali developing solution. Accordingly, during resist pattern formation, by conducting selective exposure of a resist film formed by applying the negative resist composition to a substrate, the exposed portions change to a state that is insoluble in an alkali developing solution, while the unexposed portions remain soluble in an alkali developing solution, meaning alkali developing can be used to form a resist pattern.

Generally, a resin that is soluble in an alkali developing solution (hereinafter, referred to as an "alkali-soluble resin") is used as the component (A) for a negative resist composition for an alkali developing process.

As the alkali-soluble resin, it is preferable to use a resin having a structural unit derived from at least one of an α-(hydroxyalkyl)acrylic acid and an alkyl ester (and preferably an alkyl ester of 1 to 5 carbon atoms) of an α-(hydroxyalkyl) acrylic acid, as disclosed in JP-2000-206694-A; an acrylic resin or polycycloolefin resin having a sulfonamide group, and in which an atom other than a hydrogen atom or a substituent may be bonded to the carbon atom on the α-position, as disclosed in U.S. Pat. No. 6,949,325; an acrylic resin containing a fluorinated alcohol, and in which an atom other than a hydrogen atom or a substituent may be bonded to the carbon atom on the α-position, as disclosed in U.S. Pat. No. 6,949,325, JP-2005-336452-A and JP-2006-317803-A; or a polycycloolefin resin having a fluorinated alcohol as disclosed in JP-2006-259582-A, as such resins enable the formation of a satisfactory resist pattern with minimal swelling.

Among the various acrylic acids including those compounds in which an atom other than a hydrogen atom or a substituent may be bonded to the carbon atom on the α-position, the aforementioned "α-(hydroxyalkyl)acrylic acid" refers to one or both of acrylic acid, in which a hydrogen atom is bonded to the carbon atom on the α-position having the carboxyl group bonded thereto, and α-hydroxyalkylacrylic acid, in which a hydroxyalkyl group (and preferably a hydroxyalkyl group of 1 to 5 carbon atoms) is bonded to the carbon atom on the α-position.

As the cross-linking agent, an amino-based cross-linking agent such as a glycoluril having a methylol group or an alkoxymethyl group, or a melamine-based cross-linking agent is usually preferred, as it enables formation of a favorable resist pattern with minimal swelling. The amount of the cross-linking agent added is preferably within a range from 1 to 50 parts by weight, relative to 100 parts by weight of the alkali-soluble resin.

In those cases where the resist composition of the present invention is a resist composition which forms a positive-type pattern in an alkali developing process, but forms a negative-type pattern in a solvent developing process, a base component (A0) (hereinafter referred to as "component (A0)") which exhibits increased polarity under the action of acid is preferably used as the component (A). By using the component (A0), the polarity of the base component changes upon exposure, and therefore favorable developing contrast can be achieved, not only in an alkali developing process, but also in a solvent developing process.

In those cases where an alkali developing process is used, the component (A0) is substantially insoluble in an alkali developing solution prior to exposure, but when acid is generated from the component (B) upon exposure, the action of the acid causes an increase in the polarity of the component (A0) that increases the solubility in the alkali developing solution. Accordingly, during resist pattern formation, by conducting selective exposure of a resist film formed by applying the resist composition to a substrate, the exposed portions change from being substantially insoluble in an alkali developing solution to being soluble, while the unexposed portions remain substantially insoluble in the alkali developing solution, meaning alkali developing can be used to form a positive-type resist pattern.

Further, in those cases where a solvent developing process is used, the component (A0) exhibits good solubility in an organic developing solution prior to exposure, but when acid is generated from the component (B) upon exposure, the action of the acid causes an increase in the polarity of the component (A0) that reduces the solubility in the organic developing solution. Accordingly, during resist pattern formation, by conducting selective exposure of a resist film formed by applying the resist composition to a substrate, the exposed portions change from being soluble in an organic developing solution to being substantially insoluble, while the unexposed portions remain soluble in the organic developing solution, meaning developing with an organic developing solution can be used to achieve contrast between the exposed portions and unexposed portions, enabling formation of a negative-type pattern.

In the resist composition of the present invention, the component (A) is preferably a base component that exhibits increased polarity under the action of acid (namely, the component (A0)). In other words, the resist composition of the present invention is preferably a chemically amplified resist composition that functions as a positive-type composition in an alkali developing process, and functions as a negative-type composition in a solvent developing process.

The component (A0) may be a resin component (A1) (hereinafter referred to as "component (A1)") which exhibits increased polarity under the action of acid, a low molecular weight compound (A2) (hereinafter referred to as "component (A2)") which exhibits increased polarity under the action of acid, or a mixture of the two.

[Component (A1)]

As the component (A1), a single resin component (base resin) typically used as a base component for a chemically amplified resist may be used alone, or two or more of such resin components may be mixed together.

In the present invention, the component (A1) preferably includes a structural unit derived from an acrylate ester that may have an atom other than a hydrogen atom or a substituent bonded to the carbon atom on the α-position.

In the resist composition of the present invention, the component (A1) preferably includes a structural unit (a1), which is derived from an acrylate ester that may have an atom other than a hydrogen atom or a substituent bonded to the carbon atom on the α-position, and contains an acid-degradable group that exhibits increased polarity under the action of acid.

Further, in addition to the structural unit (a1), the component (A1) preferably also includes at least one structural unit (a2) selected from the group consisting of structural units derived from an acrylate ester which contains an —SO$_2$-containing cyclic group and may have an atom other than a hydrogen atom or a substituent bonded to the carbon atom on the α-position, and structural units derived from an acrylate ester which contains a lactone-containing cyclic group and may have an atom other than a hydrogen atom or a substituent bonded to the carbon atom on the α-position.

Furthermore, in addition to the structural unit (a1), or in addition to the combination of the structural unit (a1) and the structural unit (a2), the component (A1) preferably also includes a structural unit (a3) derived from an acrylate ester which contains a polar group-containing aliphatic hydrocarbon group and may have an atom other than a hydrogen atom or a substituent bonded to the carbon atom on the α-position.

(Structural Unit (a1))

The structural unit (a1) is a structural unit which is derived from an acrylate ester that may have an atom other than a hydrogen atom or a substituent bonded to the carbon atom on the α-position, and contains an acid-degradable group that exhibits increased polarity under the action of acid.

The term "acid-degradable group" describes a group having acid degradability which, under the action of acid (such as the acid generated from the component (B) upon exposure), undergoes cleavage of some of the bonds within the structure of the acid-degradable group.

Examples of the acid-degradable group that exhibits increased polarity under the action of acid include, for example, groups which dissociate under the action of acid to form a polar group.

Examples of this polar group include a carboxyl group, hydroxyl group, amino group and sulfo group (—SO$_3$H). Among these groups, polar groups that contain an —OH within the structure (hereinafter referred to as "OH-containing polar groups) are preferred, a carboxyl group or a hydroxyl group is more preferred, and a carboxyl group is particularly desirable.

More specific examples of the acid-degradable group include groups in which an aforementioned polar group is protected with an acid-dissociable group (such as a group in which the hydrogen atom of an OH-containing polar group is protected with an acid-dissociable group).

An "acid-dissociable group" describes a group having acid dissociability which, under the action of acid (such as the acid generated from the component (B) upon exposure), undergoes cleavage of at least the bond between the acid-dissociable group and the atom adjacent to the acid-dissociable group. An acid-dissociable group that constitutes an acid-degradable group must be a group of lower polarity than the polar group generated by dissociation of the acid-dissociable group, so that when the acid-dissociable group dissociates under the action of acid, a polar group having a higher polarity than the acid-dissociable group is generated, resulting in an increase in the polarity. This results in an increase in the polarity of the overall component (A1). In those cases where an alkali developing process is used, increasing the polarity causes the component to become relatively more soluble in the alkali developing solution. In contrast, in those cases where a solvent developing process is used, the solubility in an organic developing solution containing an organic solvent decreases.

As the acid-dissociable group in the structural unit (a1), any of the groups that have been proposed as acid-dissociable groups for the base resins of chemically amplified resists can be used. Generally, groups that form either a cyclic or chain-like tertiary alkyl ester with the carboxyl group of the (meth) acrylic acid, and acetal-type acid-dissociable groups such as alkoxyalkyl groups are widely known.

Here, a "tertiary alkyl ester" describes a structure in which an ester is formed by substituting the hydrogen atom of a carboxyl group with a chain-like or cyclic alkyl group, and a tertiary carbon atom within the chain-like or cyclic alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxyl group and increasing the polarity of the component (A1).

The chain-like or cyclic alkyl group may have a substituent.

Hereinafter, for the sake of simplicity, groups that exhibit acid dissociability as a result of the formation of a tertiary alkyl ester with a carboxyl group are referred to as "tertiary alkyl ester-type acid-dissociable groups".

Examples of tertiary alkyl ester-type acid-dissociable groups include aliphatic branched acid-dissociable groups and aliphatic cyclic group-containing acid-dissociable groups.

In the present description and claims, the term "aliphatic branched" refers to a branched structure having no aromaticity.

The structure of the "aliphatic branched acid-dissociable group" is not limited to groups constituted of only carbon atoms and hydrogen atoms (not limited to hydrocarbon groups), but is preferably a hydrocarbon group.

Further, the "hydrocarbon group" may be either saturated or unsaturated, but in most cases, is preferably saturated.

Examples of preferred aliphatic branched acid-dissociable groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of the substituent include alkyl groups of 1 to 5 carbon atoms, alkoxy groups of 1 to 5 carbon atoms, a fluorine atom, fluorinated alkyl groups of 1 to 5 carbon atoms, and an oxygen atom (=O).

The basic ring structure of the "aliphatic cyclic group" excluding substituents is not limited to structures constituted from only carbon and hydrogen (not limited to hydrocarbon groups), but is preferably a hydrocarbon group. Further, the "hydrocarbon group" may be either saturated or unsaturated, but in most cases, is preferably saturated. The "aliphatic cyclic group" is preferably a polycyclic group.

Examples of such aliphatic cyclic groups include groups in which one or more hydrogen atoms have been removed from a monocycloalkane or a polycycloalkane such as a bicycloalkane, tricycloalkane or tetracycloalkane, which may or may not be substituted with an alkyl group of 1 to 5 carbon atoms, a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

Examples of the aliphatic cyclic group-containing acid-dissociable group include groups having a tertiary carbon atom on the ring structure of a cycloalkyl group. Specific examples include groups represented by general formulas (1-1) to (1-9) shown below, such as a 2-methyl-2-adamantyl group and 2-ethyl-2-adamantyl group.

Further, additional examples of the aliphatic branched acid-dissociable groups include groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, such as the groups represented by general formulas (2-1) to (2-6) shown below.

Chemical Formula 3]

(1-1)

(1-2)

(1-3)

(1-4)

(1-5)

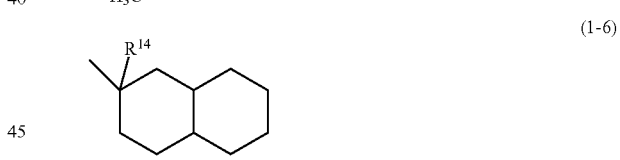

(1-6)

(1-7)

(1-8)

(1-9)

In the formulas above, $R^{14}$ represents an alkyl group, and g represents an integer of 0 to 8

[Chemical Formula 4]

(2-1)
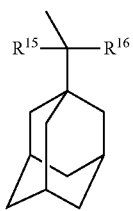

(2-2)
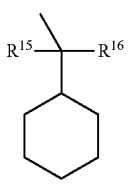

(2-3)
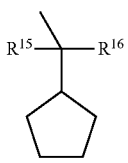

(2-4)
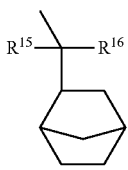

(2-5)
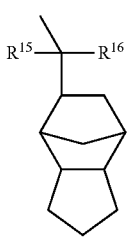

(2-6)
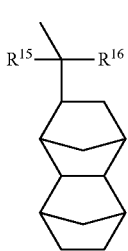

In the formulas above, each of $R^{15}$ and $R^{16}$ independently represents an alkyl group (which may be linear or branched, but preferably contains 1 to 5 carbon atoms).

As the alkyl group for $R^{14}$, a linear or branched alkyl group is preferable.

The linear alkyl group preferably has 1 to 5 carbon atoms, more preferably 1 to 4 carbon atoms, and still more preferably 1 or 2 carbon atoms. Specific examples include a methyl group, ethyl group, n-propyl group, n-butyl group and n-pentyl group. Among these, a methyl group, ethyl group or n-butyl group is preferable, and a methyl group or ethyl group is more preferable.

The branched alkyl group preferably has 3 to 10 carbon atoms, and more preferably 3 to 5 carbon atoms. Specific examples of such branched alkyl groups include an isopropyl group, isobutyl group, tert-butyl group, isopentyl group and neopentyl group, and an isopropyl group is particularly desirable.

g is preferably an integer of 0 to 3, more preferably an integer of 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), some of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid-dissociable group" generally substitutes a hydrogen atom at the terminal of an OH-containing polar group such as a carboxyl group or hydroxyl group, so as to be bonded with an oxygen atom. When acid is generated upon exposure, the generated acid acts to break the bond between the acetal-type acid-dissociable group and the oxygen atom to which the acetal-type acid-dissociable group is bonded, thereby forming an OH-containing polar group such as a carboxyl group or hydroxyl group, and increasing the polarity of the component (A1).

Examples of acetal-type acid-dissociable groups include groups represented by general formula (p1) shown below.

[Chemical Formula 5]

(p1)
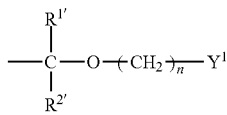

In the formula, each of $R^{1'}$ and $R^{2'}$ independently represents a hydrogen atom or an alkyl group of 1 to 5 carbon atoms, n represents an integer of 0 to 3, and $Y^1$ represents an alkyl group of 1 to 5 carbon atoms or an aliphatic cyclic group.

In the above formula, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, although a methyl group or ethyl group is preferable, and a methyl group is particularly desirable.

In the present invention, it is preferable that at least one of $R^{1'}$ and $R^{2'}$ is a hydrogen atom. That is, it is preferable that the acid-dissociable group (p1) is a group represented by general formula (p1-1) shown below.

[Chemical Formula 6]

(p1-1)
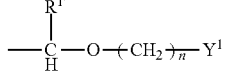

In the formula, $R^{1'}$, n and $Y^1$ are the same as defined above.

As the alkyl group of 1 to 5 carbon atoms for Y, the same alkyl groups of 1 to 5 carbon atoms as those described above for R above can be used.

As the aliphatic cyclic group for $Y^1$, any of the monocyclic or polycyclic aliphatic cyclic groups which have been proposed for conventional ArF resists and the like can be appropriately selected for use. For example, the same groups as those described above in connection with the "aliphatic cyclic group" can be used.

Further, as the acetal-type acid-dissociable group, groups represented by general formula (p2) shown below can also be used.

[Chemical Formula 7]

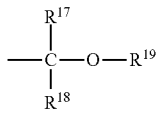

(p2)

In the formula, each of $R^{17}$ and $R^{18}$ independently represents a linear or branched alkyl group or a hydrogen atom, and $R^{19}$ represents a linear, branched or cyclic alkyl group, or alternatively, each of $R^{17}$ and $R^{19}$ may independently represent a linear or branched alkylene group, wherein $R^{17}$ and $R^{19}$ are bonded to each other to form a ring.

The alkyl group for $R^{17}$ and $R^{18}$ preferably has 1 to 15 carbon atoms, and may be either linear or branched. As the alkyl group, an ethyl group or methyl group is preferable, and a methyl group is most preferable. It is particularly desirable that either one of $R^{17}$ and $R^{18}$ is a hydrogen atom, and the other is a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. Examples of the cycloalkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane and cyclohexane, and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

Further, in the above formula, each of $R^{17}$ and $R^{19}$ may independently represent a linear or branched alkylene group (preferably an alkylene group of 1 to 5 carbon atoms), wherein $R^{19}$ and $R^{17}$ are bonded to each other.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

As the structural unit (a1), it is preferable to use one or more structural units selected from the group consisting of structural units represented by general formula (a1-0-1) shown below and structural units represented by general formula (a1-0-2) shown below.

[Chemical Formula 8]

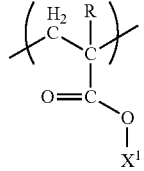

(a1-0-1)

In the formula, R represents a hydrogen atom, an alkyl group of 1 to 5 carbon atoms or a halogenated alkyl group of 1 to 5 carbon atoms, and $X^1$ represents an acid-dissociable group.

[Chemical Formula 9]

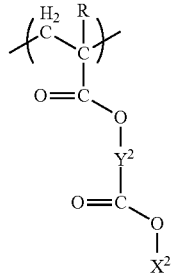

(a1-0-2)

In the formula, R represents a hydrogen atom, an alkyl group of 1 to 5 carbon atoms or a halogenated alkyl group of 1 to 5 carbon atoms, $X^2$ represents an acid-dissociable group, and $Y^2$ represents a divalent linking group.

In general formula (a1-0-1), the alkyl group of 1 to 5 carbon atoms and halogenated alkyl group of 1 to 5 carbon atoms for R are the same as defined above for the alkyl group of 1 to 5 carbon atoms and halogenated alkyl group of 1 to 5 carbon atoms which may be bonded to the carbon atom on the α-position.

$X^1$ is not particularly limited as long as it is an acid-dissociable group. Examples thereof include the aforementioned tertiary alkyl ester-type acid-dissociable groups and acetal-type acid-dissociable groups, and of these, tertiary alkyl ester-type acid-dissociable groups are preferable.

In general formula (a1-0-2), R is the same as defined above.

$X^2$ is the same as defined for $X^1$ in general formula (a1-0-1).

Examples of the divalent linking group for $Y^2$ include the same divalent linking groups as those described below for Y in formula (b1-2). Of these, $Y^2$ in the present invention is preferably a divalent linking group containing a hetero atom, is more preferably a group represented by a formula -A-O-B-, -[A-C(=O)-O]$_m$-B- or -C(=O)-B-, and is still more preferably a group represented by -C(=O)-O-(CH$_2$)$_b$- (wherein A, B, m and b are the same as defined below).

Specific examples of the structural unit (a1) include structural units represented by general formulas (a1-1) to (a1-4) shown below.

[Chemical Formula 10]

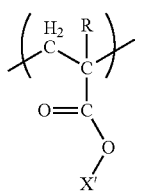 (a1-1)

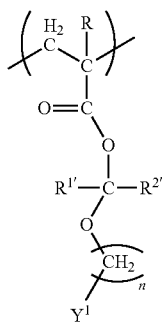 (a1-2)

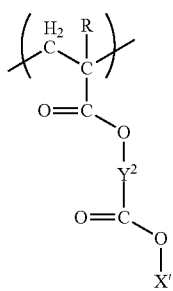 (a1-3)

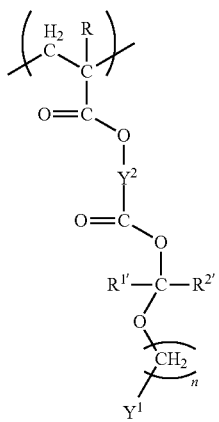 (a1-4)

In the formulas, X' represents a tertiary alkyl ester-type acid-dissociable group, represents an alkyl group of 1 to 5 carbon atoms or an aliphatic cyclic group, n represents an integer of 0 to 3, $Y^2$ represents a divalent linking group, R is the same as defined above, and each of $R^{1'}$ and $R^{2'}$ independently represents a hydrogen atom or an alkyl group of 1 to 5 carbon atoms.

In the above formulas, examples of the tertiary alkyl ester-type acid-dissociable group for X' include the same tertiary alkyl ester-type acid-dissociable groups as those described above for $X^1$.

$R^{1'}$, $R^{2'}$, n and $Y^1$ are respectively the same as defined for $R^{1'}$, $R^{2'}$, n and $Y^1$ in general formula (p1) described above in connection with the "acetal-type acid-dissociable group".

Examples of $Y^2$ include the same groups as those described above for $Y^2$ in general formula (a1-0-2).

Specific examples of the structural units represented by general formulas (a1-1) to (a1-4) are shown below.

In the formulas shown below, $R^\alpha$ represents a hydrogen atom, a methyl group or a trifluoromethyl group.

[Chemical Formula 11]

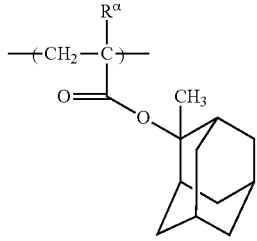 (a1-1-1)

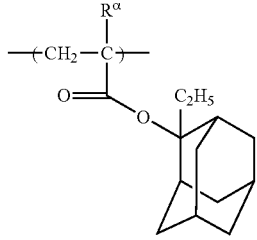 (a1-1-2)

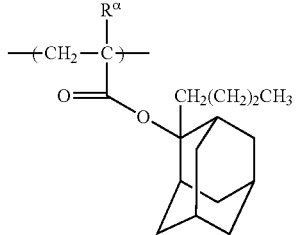 (a1-1-3)

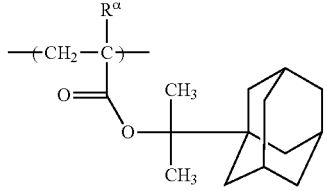 (a1-1-4)

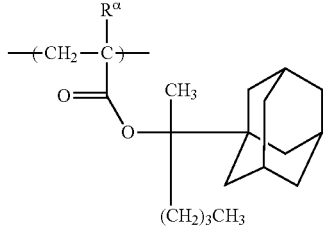 (a1-1-5)

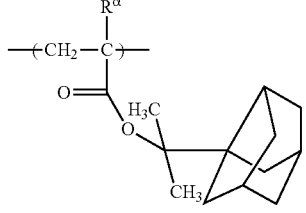 (a1-1-6)

(a1-1-7) 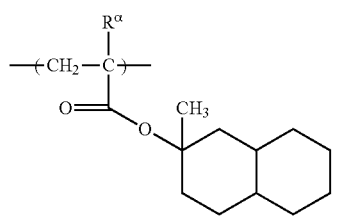
(a1-1-8) 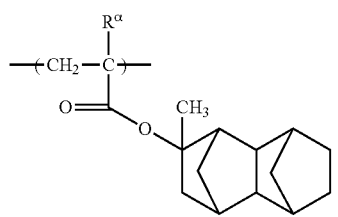
(a1-1-9) 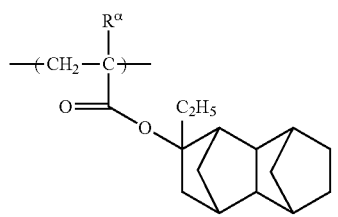
[Chemical Formula 12]
(a1-1-10) 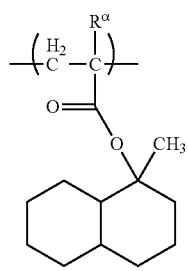
(a1-1-11) 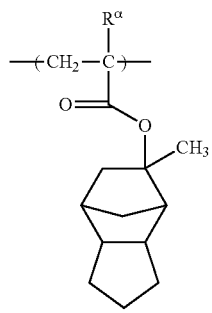
(a1-1-12) 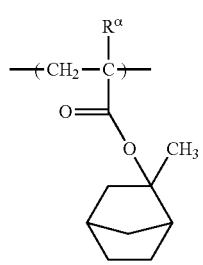
(a1-1-13) 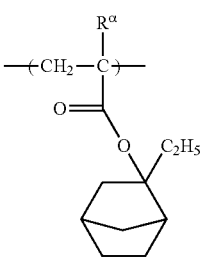
(a1-1-14) 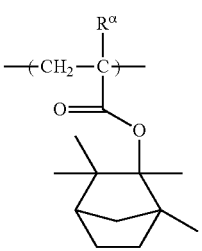
(a1-1-15) 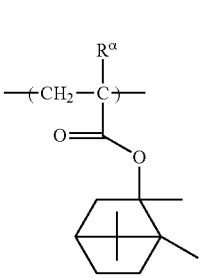
(a1-1-16) 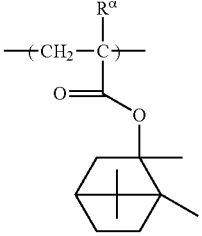
(a1-1-17) 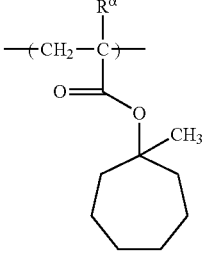
(a1-1-18) 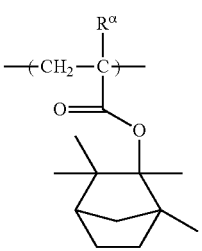

(a1-1-19)
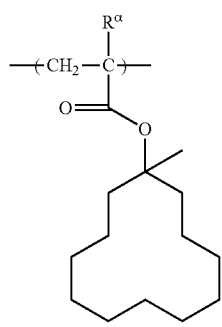
(a1-1-20)
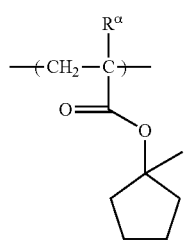
(a1-1-21)
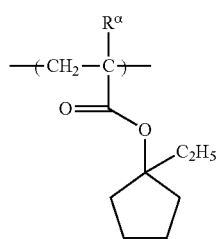
[Chemical Formula 13]
(a1-1-22)
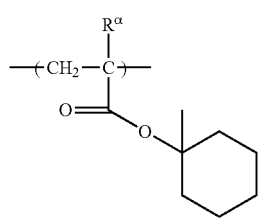
(a1-1-23)
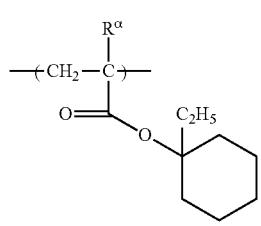
(a1-1-24)
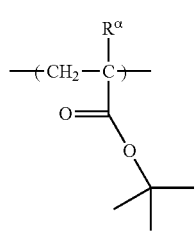
(a1-1-25)
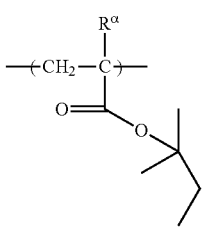
(a1-1-26)
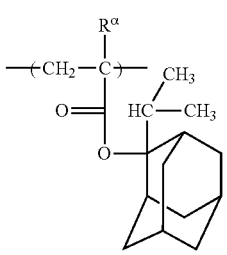
(a1-1-27)
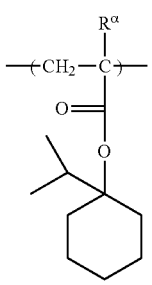
(a1-1-28)
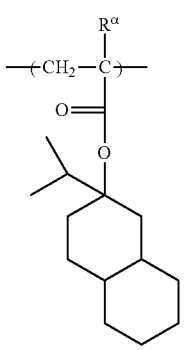
(a1-1-29)

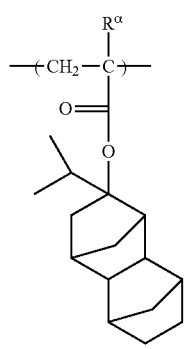 (a1-1-30)
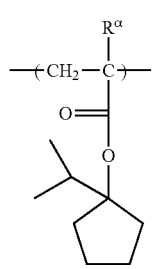 (a1-1-31)
[Chemical Formula 14]
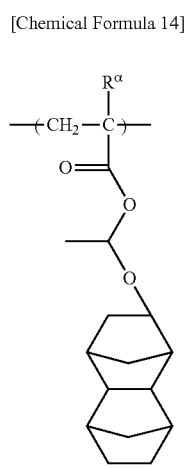 (a1-2-1)
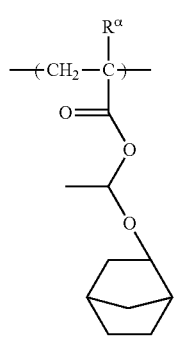 (a1-2-2)
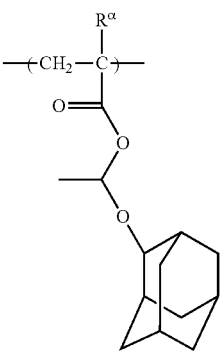 (a1-2-3)
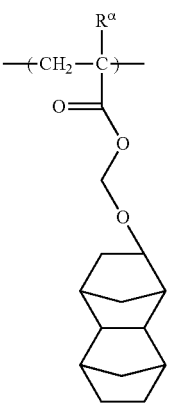 (a1-2-4)
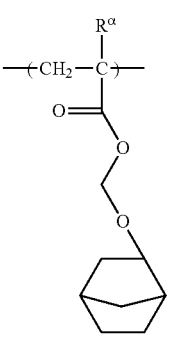 (a1-2-5)
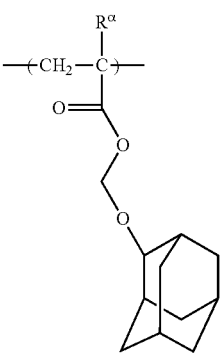 (a1-2-6)

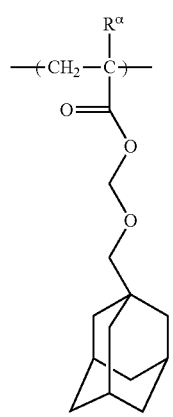
(a1-2-7)
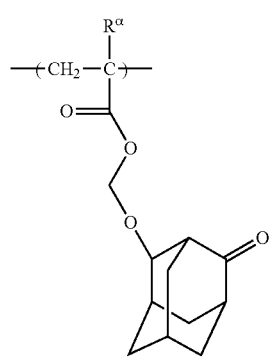
(a1-2-8)
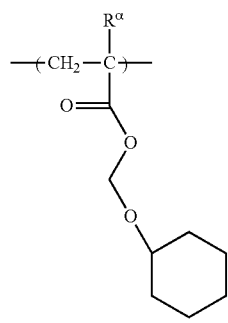
(a1-2-9)
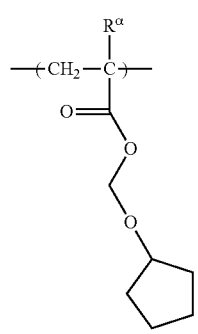
(a1-2-10)
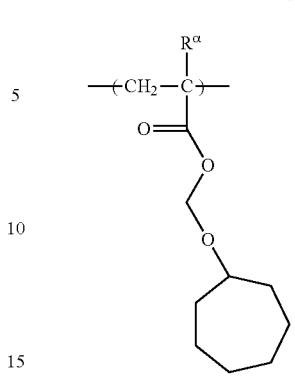
(a1-2-11)
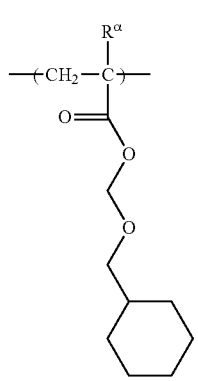
(a1-2-12)
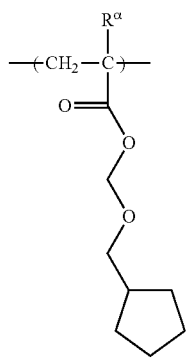
(a1-2-13)
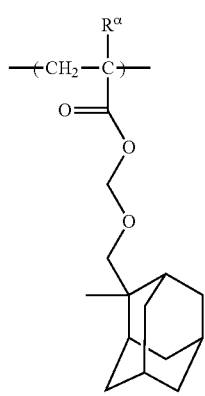
(a1-2-14)

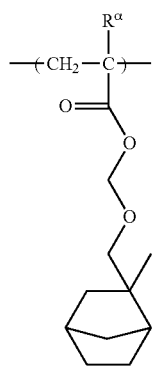 (a1-2-15)
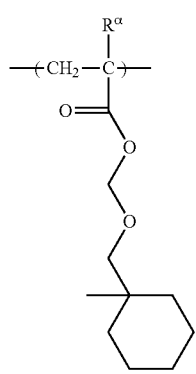 (a1-2-16)
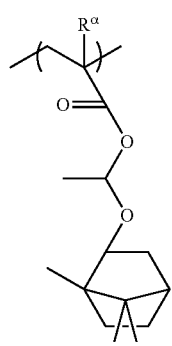 (a1-2-17)
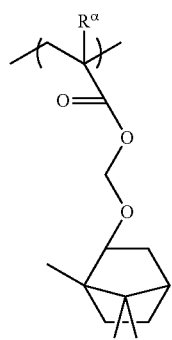 (a1-2-18)
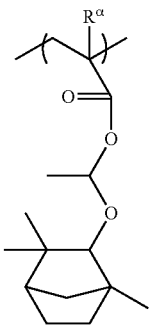 (a1-2-19)
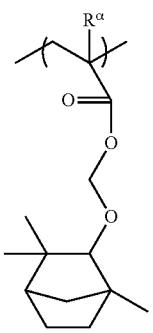 (a1-2-20)
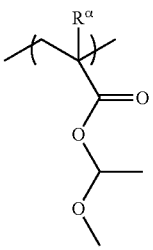 (a1-2-21)
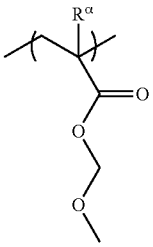 (a1-2-22)
(a1-2-23)

(a1-2-24)
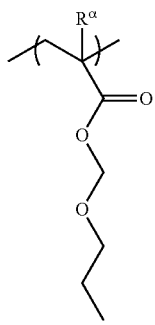
[Chemical Formula 15]
(a1-3-1)
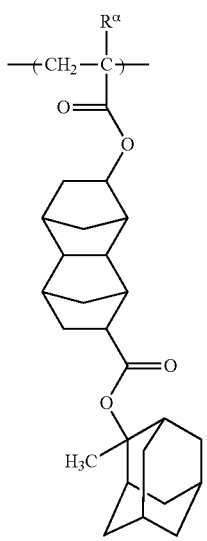
(a1-3-2)
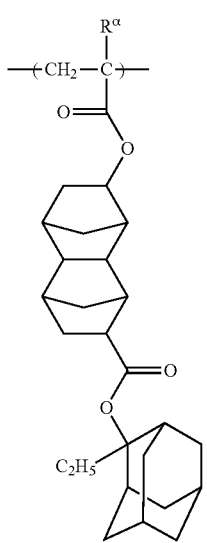
(a1-3-3)
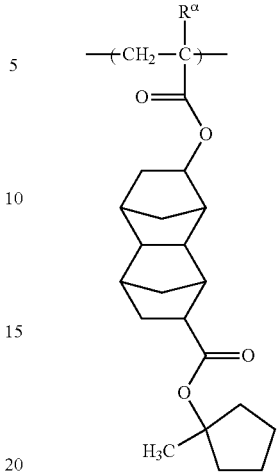
(a1-3-4)
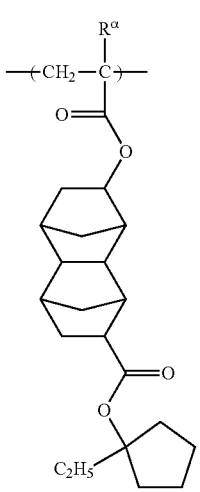
(a1-3-5)
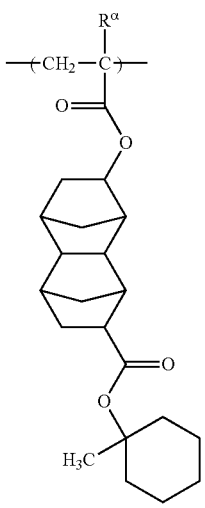

(a1-3-6)
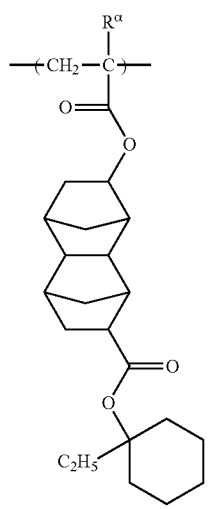
(a1-3-7)
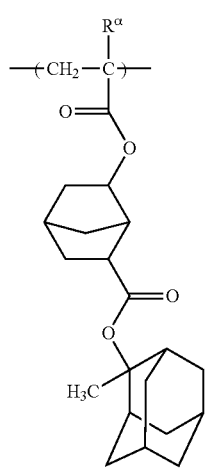
(a1-3-8)
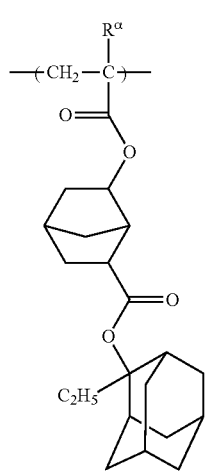
(a1-3-9)
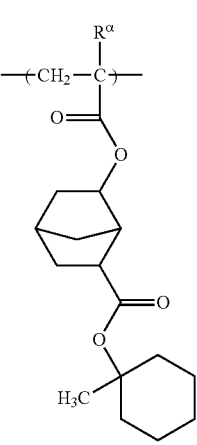
(a1-3-10)
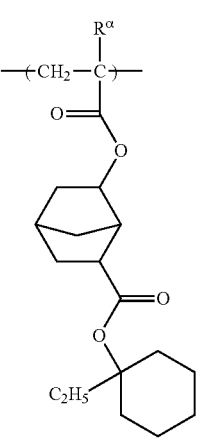
(a1-3-11)
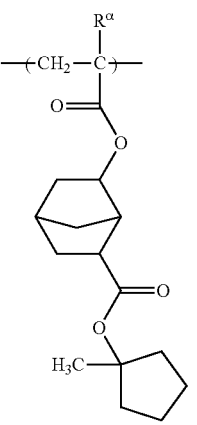

(a1-3-12) 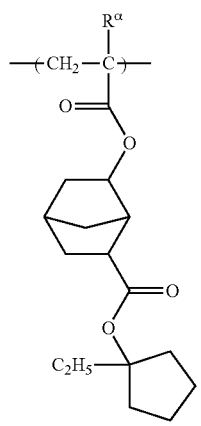
(a1-3-13) 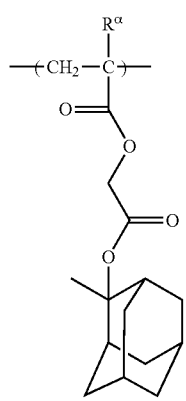
(a1-3-14) 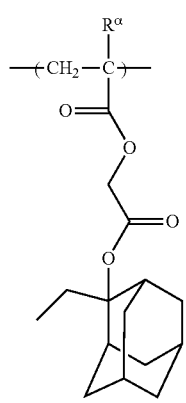
(a1-3-15) 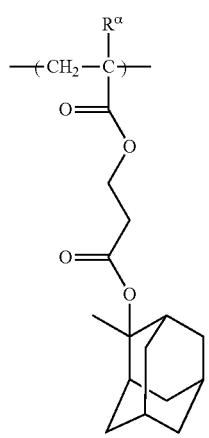
(a1-3-16) 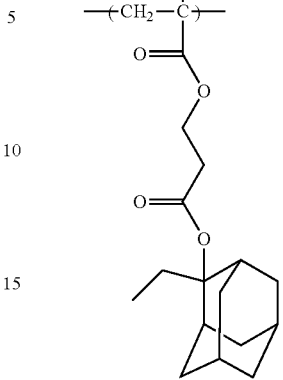
(a1-3-17) 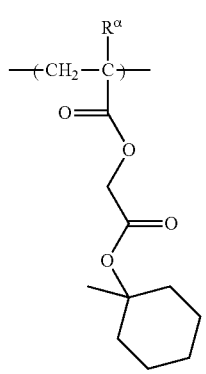
(a1-3-18) 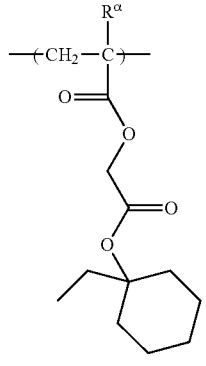
[Chemical Formula 16]
(a1-3-19) 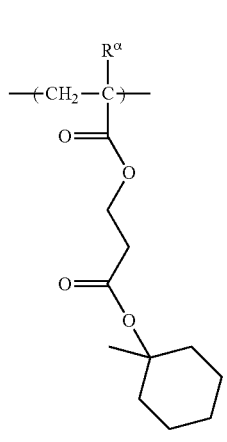

(a1-3-20) 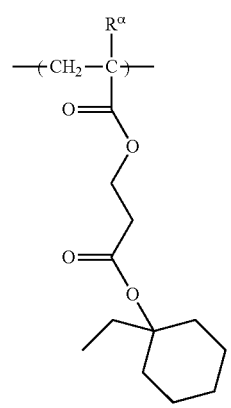
(a1-3-24) 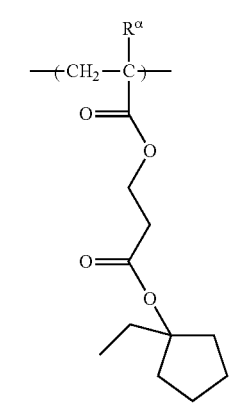
(a1-3-21) 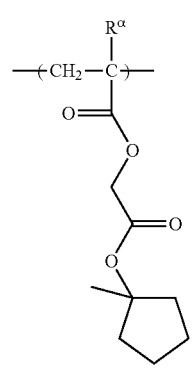
[Chemical Formula 17]
(a1-3-25) 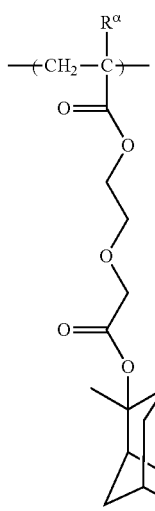
(a1-3-22)
(a1-3-23)
(a1-3-26) 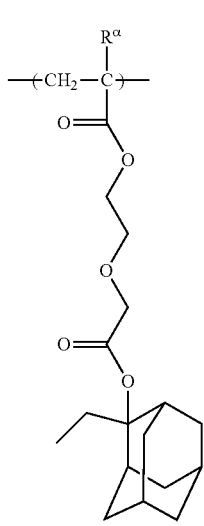
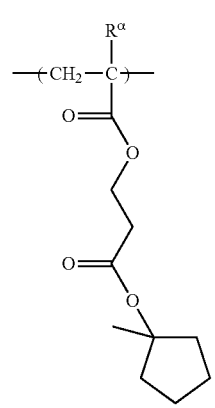

(a1-3-27) 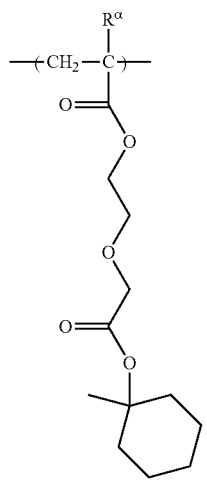
(a1-3-28) 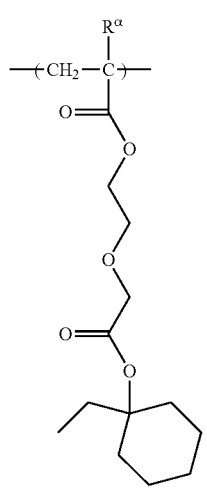
(a1-3-29) 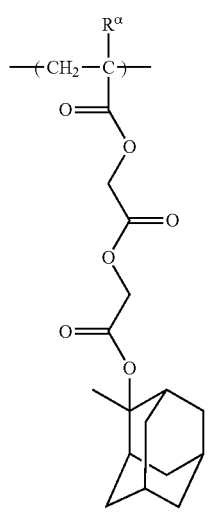
(a1-3-30) 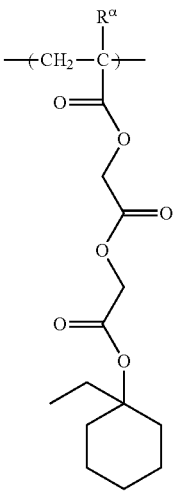
(a1-3-31) 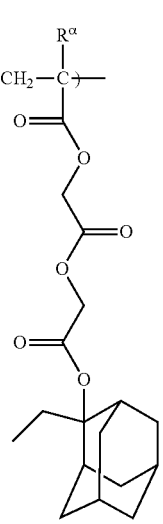
(a1-3-32) 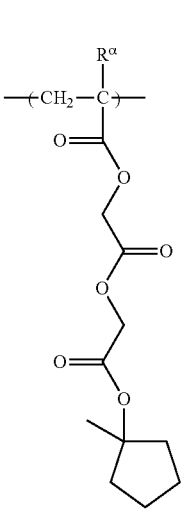

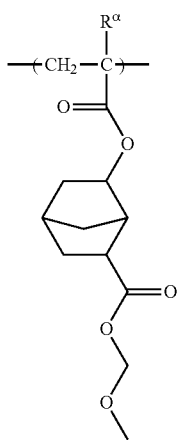
(a1-4-1)
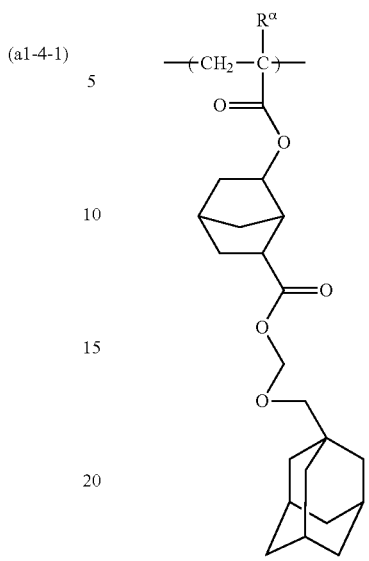
(a1-4-2)
(a1-4-3)
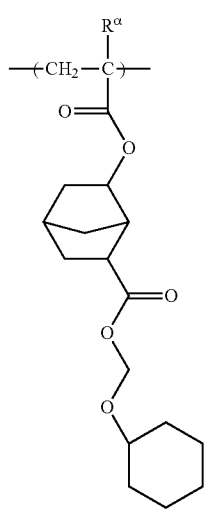
(a1-4-4)
(a1-4-5)
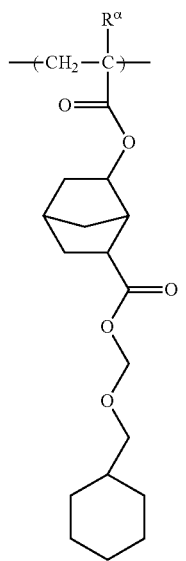
(a1-4-6)

(a1-4-7)
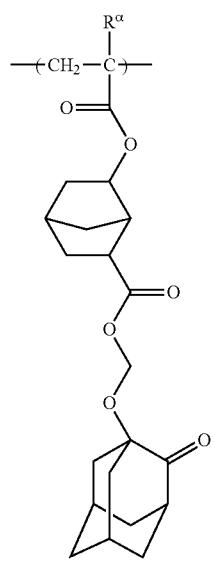
(a1-4-9)
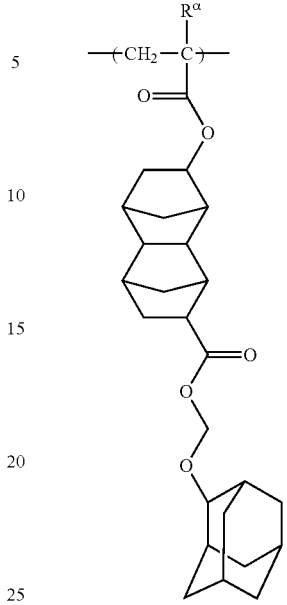
(a1-4-8)
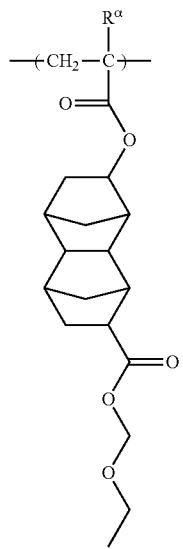
(a1-4-10)
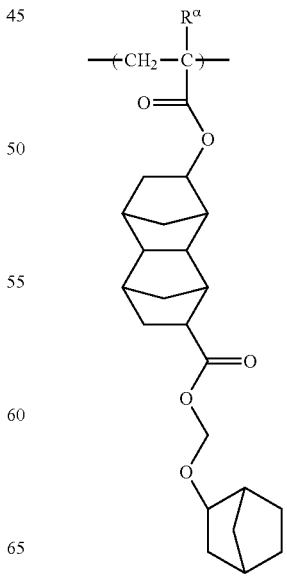

(a1-4-11)
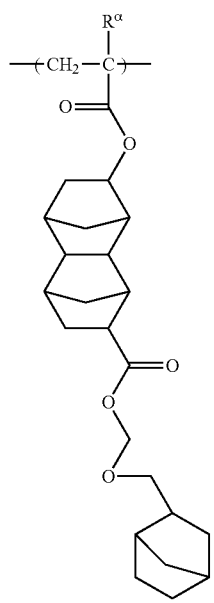
(a1-4-13)
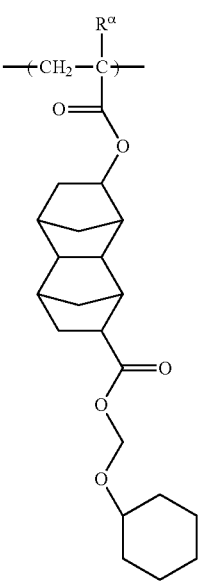
(a1-4-12)
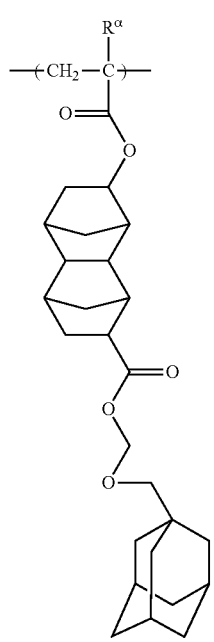
(a1-4-14)
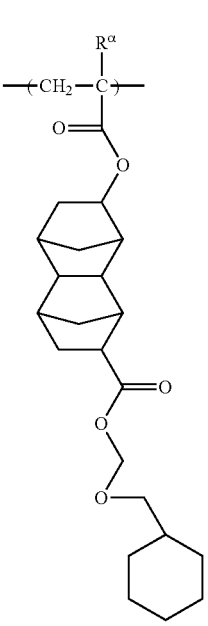

(a1-4-15)

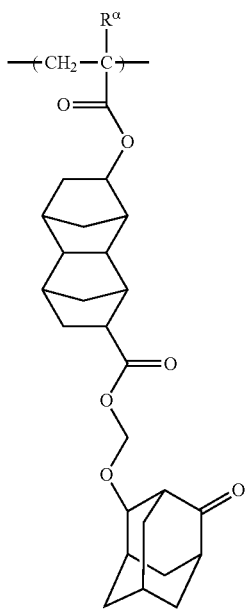

As the structural unit (a1), one type of structural unit may be used alone, or two or more types may be used in combination.

Among these, structural units represented by general formula (a1-1), (a1-2) or (a1-3) are preferable, and more specifically, the use of at least one structural unit selected from the group consisting of structural units represented by formulas (a1-1-1) to (a1-1-4), formulas (a1-1-20) to (a1-1-23), formulas (a1-2-1) to (a1-2-24), and formulas (a1-3-25) to (a1-3-28) is more preferable.

Moreover, as the structural unit (a1), structural units represented by general formula (a1-1-01) shown below, which includes the structural units represented by formulas (a1-1-1) to (a1-1-3) and formula (a1-1-26), structural units represented by general formula (a1-1-02) shown below, which includes the structural units represented by formulas (a1-1-16) and (a1-1-17) and formulas (a1-1-20) to (a1-1-23), structural units represented by general formula (a1-3-01) shown below, which includes the structural units represented by formulas (a1-3-25) and (a1-3-26), structural units represented by general formula (a1-3-02) shown below, which includes the structural units represented by formulas (a1-3-27) and (a1-3-28), and structural units represented by general formula (a1-3-03) shown below, which includes the structural units represented by formulas (a1-3-29) and (a1-3-30) are preferred.

[Chemical Formula 19]

(a1-1-01)

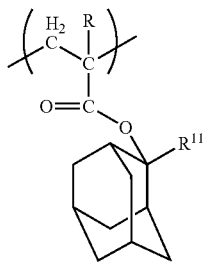

(a1-1-02)

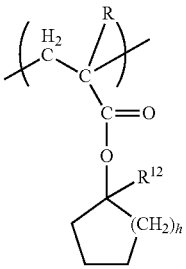

In the formulas, each R independently represents a hydrogen atom, an alkyl group of 1 to 5 carbon atoms or a halogenated alkyl group of 1 to 5 carbon atoms, $R^{11}$ represents an alkyl group of 1 to 5 carbon atoms, $R^{12}$ represents an alkyl group of 1 to 7 carbon atoms, and h represents an integer of 1 to 6.

In general formula (a1-1-01), R is the same as defined above. The alkyl group of 1 to 5 carbon atoms for $R^{11}$ is the same as defined above for the alkyl group of 1 to 5 carbon atoms for R, and is preferably a methyl group, ethyl group or isopropyl group.

In general formula (a1-1-02), R is the same as defined above for R. The alkyl group of 1 to 5 carbon atoms for $R^{12}$ is the same as defined above for the alkyl group of 1 to 5 carbon atoms for R, and is preferably a methyl group, ethyl group or isopropyl group. h is preferably 1 or 2, and most preferably 2.

[Chemical Formula 20]

(a1-3-01)

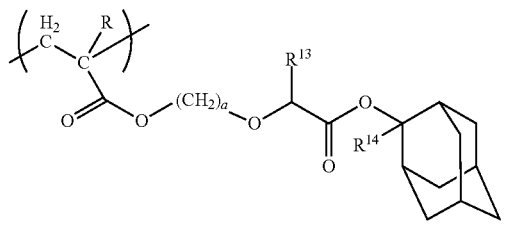

In the formula, R represents a hydrogen atom, an alkyl group of 1 to 5 carbon atoms or a halogenated alkyl group of 1 to 5 carbon atoms, $R^{14}$ is the same as defined above, $R^{13}$ represents a hydrogen atom or a methyl group, and a represents an integer of 1 to 10.

[Chemical Formula 21]

(a1-3-02)

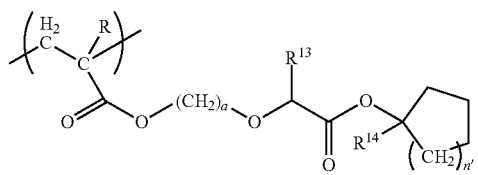

In the formula, R represents a hydrogen atom, an alkyl group of 1 to 5 carbon atoms or a halogenated alkyl group of 1 to 5 carbon atoms, $R^{14}$ is the same as defined above, $R^{13}$ represents a hydrogen atom or a methyl group, a represents an integer of 1 to 10, and n' represents an integer of 1 to 6.

[Chemical Formula 22]

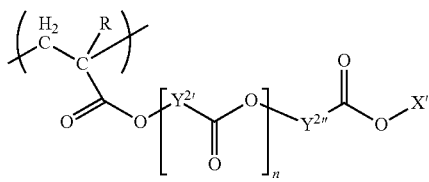

(a1-3-03)

In the formula, R is the same as defined above, each of $Y^{2\prime}$ and $Y^{2\prime\prime}$ independently represents a divalent linking group, $X'$ represents an acid-dissociable group, and n represents an integer of 0 to 3.

In general formulas (a1-3-01) to (a1-3-03), R is the same as defined above.

$R^{13}$ is preferably a hydrogen atom.

n' is preferably 1 or 2, and is most preferably 2.

a is preferably an integer of 1 to 8, more preferably an integer of 2 to 5, and most preferably 2.

Examples of the divalent linking groups for $Y^{2\prime}$ and $Y^{2\prime\prime}$ include the same groups as those described above for $Y^2$ in general formula (a1-3).

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid-dissociable group for $X'$, the same groups as those described above for $X'$ in formula (a1-0-1) can be used. $X'$ is preferably a tertiary alkyl ester-type acid-dissociable group, and more preferably an aforementioned group which has a tertiary carbon atom on the ring structure of a monovalent aliphatic cyclic group. Among the aforementioned groups, a group represented by general formula (1-1) above is preferable.

n represents an integer of 0 to 3, preferably an integer of 0 to 2, more preferably 0 or 1, and most preferably 1.

In the component (A1), the amount of the structural unit (a1), based on the combined total of all the structural units that constitute the component (A1), is preferably within a range from 5 to 80 mol %, more preferably from 10 to 80 mol %, and still more preferably from 15 to 75 mol %. By ensuring that the amount of the structural unit (a1) is at least as large as the lower limit of the aforementioned range, a pattern can be formed easily using a resist composition prepared from the component (A1), whereas by ensuring that the amount is not more than the upper limit of the above range, a good balance can be achieved with the other structural units.

(Structural Unit (a2))

The structural unit (a2) is at least one structural unit selected from the group consisting of structural units derived from an acrylate ester which contains an —$SO_2$-containing cyclic group and may have an atom other than a hydrogen atom or a substituent bonded to the carbon atom on the α-position (hereinafter referred to as "structural unit ($a2^S$)"), and structural units derived from an acrylate ester which contains a lactone-containing cyclic group and may have an atom other than a hydrogen atom or a substituent bonded to the carbon atom on the α-position (hereinafter referred to as "structural unit ($a2^L$)").

By incorporating an —$SO_2$-containing cyclic group or a lactone-containing cyclic group, the structural unit (a2) contributes to improvements in the lithography properties, including improving the adhesion between the substrate and a resist film formed using a positive resist composition containing the component (A1), and increasing the compatibility with developing solutions containing water (particularly in the case of an alkali developing process).

Structural Unit ($a2^S$)

The structural unit ($a2^S$) is a structural unit derived from an acrylate ester which contains an —$SO_2$-containing cyclic group and may have an atom other than a hydrogen atom or a substituent bonded to the carbon atom on the α-position.

In this description, the term "—$SO_2$-containing cyclic group" refers to a cyclic group which includes a ring containing an —$SO_2$— moiety within the ring structure, and specifically refers to cyclic groups in which the sulfur atom (S) of the —$SO_2$— forms a part of the ring structure of the cyclic group. The ring containing the —$SO_2$— moiety within the ring structure is counted as the first ring, so that groups containing only that ring are referred to as monocyclic groups, and groups containing other ring structures are described as polycyclic groups regardless of the structure of the other rings. The —$SO_2$-containing cyclic group may be either monocyclic or polycyclic.

The —$SO_2$-containing cyclic group is preferably a cyclic group containing an —O—$SO_2$— moiety within the ring structure, namely a cyclic group containing a sultone ring in which the —O—S— within the —O—$SO_2$— forms a part of the ring structure.

The —$SO_2$-containing cyclic group preferably contains 3 to 30 carbon atoms, more preferably 4 to 20 carbon atoms, still more preferably 4 to 15 carbon atoms, and most preferably 4 to 12 carbon atoms. Here, the number of carbon atoms refers to the number of carbon atoms that constitute the ring structure, and does not include carbon atoms contained within substituents.

The —$SO_2$-containing cyclic group may be an —$SO_2$-containing aliphatic cyclic group or an —$SO_2$-containing aromatic cyclic group. An —$SO_2$-containing aliphatic cyclic group is preferred.

Examples of the —$SO_2$-containing aliphatic cyclic group include groups in which at least one hydrogen atom has been removed from an aliphatic hydrocarbon ring in which some of the carbon atoms that constitute the ring structure have been substituted with either —$SO_2$— or —O—$SO_2$—. More specific examples include groups in which at least one hydrogen atom has been removed from an aliphatic hydrocarbon ring in which a —$CH_2$— moiety that constitutes part of the ring structure has been substituted with an —$SO_2$— moiety, and groups in which at least one hydrogen atom has been removed from an aliphatic hydrocarbon ring in which a —$CH_2$—$CH_2$— moiety that constitutes part of the ring structure has been substituted with an —O—$SO_2$— moiety.

The alicyclic hydrocarbon group preferably contains 3 to 20 carbon atoms, and more preferably 3 to 12 carbon atoms.

The alicyclic hydrocarbon group may be either polycyclic or monocyclic. As the monocyclic alicyclic hydrocarbon group, groups in which two hydrogen atoms have been removed from a monocycloalkane of 3 to 6 carbon atoms are preferable, and specific examples of such monocycloalkanes include cyclopentane and cyclohexane. As the polycyclic alicyclic hydrocarbon group, groups in which two hydrogen atoms have been removed from a polycycloalkane of 7 to 12 carbon atoms are preferable, and specific examples of such polycycloalkanes include adamantane, norbornane, isobornane, tricyclodecane and tetracyclododecane.

The —SO$_2$-containing cyclic group may have a substituent. Examples of the substituent include an alkyl group, alkoxy group, halogen atom, halogenated alkyl group, hydroxyl group, oxygen atom (=O), —COOR", —OC(=O)R", hydroxyalkyl group and cyano group.

The alkyl group for the substituent is preferably an alkyl group of 1 to 6 carbon atoms. The alkyl group is preferably a linear or branched group. Specific examples include a methyl group, ethyl group, propyl group, isopropyl group, n-butyl group, isobutyl group, tert-butyl group, pentyl group, isopentyl group, neopentyl group or hexyl group. Among these, a methyl group or ethyl group is preferred, and a methyl group is particularly desirable.

The alkoxy group for the substituent is preferably an alkoxy group of 1 to 6 carbon atoms. The alkoxy group is preferably a linear or branched group. Specific examples include groups in which an oxygen atom (—O—) is bonded to any of the substituent alkyl groups described above.

Examples of the halogen atom for the substituent include a fluorine atom, chlorine atom, bromine atom or iodine atom, and a fluorine atom is preferable.

Examples of the halogenated alkyl group for the substituent include groups in which some or all of the hydrogen atoms of an aforementioned alkyl group have been substituted with the above halogen atoms. A fluorinated alkyl group is preferred as the halogenated alkyl group, and a perfluoroalkyl group is particularly desirable.

In the aforementioned —COOR" group and —O(C=O)R" group, R" represents a hydrogen atom, or a linear, branched or cyclic alkyl group of 1 to 15 carbon atoms.

In those cases where R" represents a linear or branched alkyl group, the alkyl group preferably contains 1 to 10 carbon atoms, and more preferably 1 to 5 carbon atoms, and is most preferably a methyl group or ethyl group.

In those cases where R" is a cyclic alkyl group, the alkyl group preferably contains 3 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

The hydroxyalkyl group for the substituent preferably contains 1 to 6 carbon atoms, and specific examples thereof include groups in which at least one hydrogen atom within an aforementioned alkyl group substituent has been substituted with a hydroxyl group.

More specific examples of the —SO$_2$-containing cyclic group include groups represented by general formulas (3-1) to (3-4) shown below.

[Chemical Formula 23]

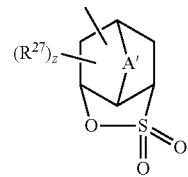

(3-1)

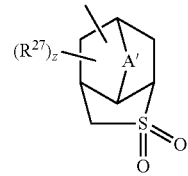

(3-2)

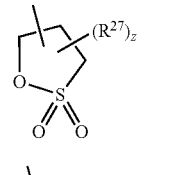

(3-3)

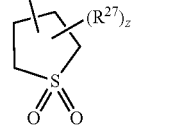

(3-4)

In the formulas, A' represents an oxygen atom, a sulfur atom, or an alkylene group of 1 to 5 carbon atoms which may contain an oxygen atom or a sulfur atom, z represents an integer of 0 to 2, and R$^{27}$ represents an alkyl group, alkoxy group, halogenated alkyl group, hydroxyl group, —COOR", —OC(=O)R", hydroxyalkyl group or cyano group, wherein R" represents a hydrogen atom or an alkyl group.

In general formulas (3-1) to (3-4) above, A' represents an oxygen atom (—O—), a sulfur atom (—S—), or an alkylene group of 1 to 5 carbon atoms which may contain an oxygen atom or a sulfur atom.

As the alkylene group of 1 to 5 carbon atoms for A', a linear or branched alkylene group is preferable, and examples thereof include a methylene group, ethylene group, n-propylene group and isopropylene group.

Examples of the alkylene groups which contain an oxygen atom or a sulfur atom include the aforementioned alkylene groups in which —O— or —S— is either bonded to the terminal of the alkylene group or interposed within the alkylene group. Specific examples of such alkylene groups include —O—CH$_2$—, —CH$_2$—O—CH$_2$—, —S—CH$_2$— and —CH$_2$—S—CH$_2$—.

A' is preferably an alkylene group of 1 to 5 carbon atoms or —O—, more preferably an alkylene group of 1 to 5 carbon atoms, and most preferably a methylene group.

z represents an integer of 0 to 2, and is most preferably 0.

When z is 2, the plurality of R$^{27}$ groups may be the same or different from each other.

Examples of the alkyl group, alkoxy group, halogenated alkyl group, —COOR" groups, —OC(=O)R" groups and hydroxyalkyl group for R$^{27}$ include the same alkyl groups, alkoxy groups, halogenated alkyl groups, —COOR" groups, —OC(=O)R" groups and hydroxyalkyl groups as those described above for the substituent which the —SO$_2$-containing cyclic group may have.

Specific examples of the cyclic groups represented by general formulas (3-1) to (3-4) are shown below. In the formulas shown below, "Ac" represents an acetyl group.
[Chemical Formula 24]
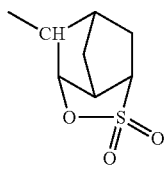 (3-1-1)
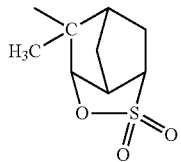 (3-1-2)
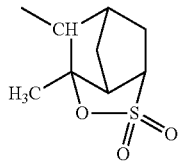 (3-1-3)
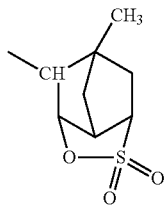 (3-1-4)
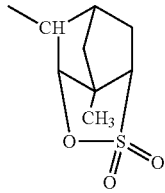 (3-1-5)
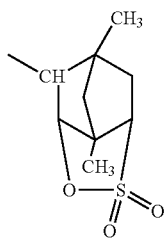 (3-1-6)
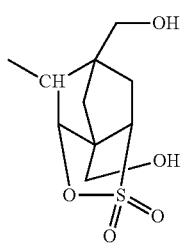 (3-1-7)
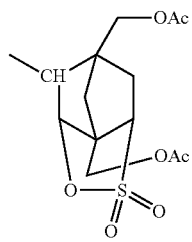 (3-1-8)
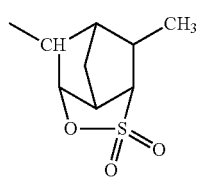 (3-1-9)
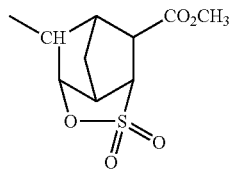 (3-1-10)
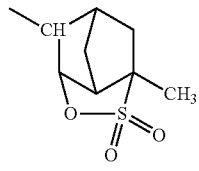 (3-1-11)
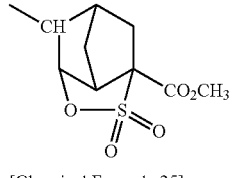 (3-1-12)
[Chemical Formula 25]
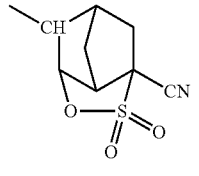 (3-1-13)
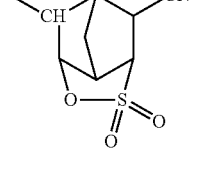 (3-1-14)
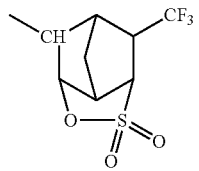 (3-1-15)

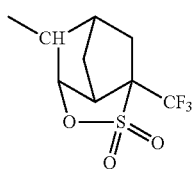 (3-1-16)
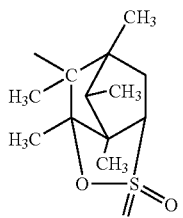
[Chemical Formula 26]
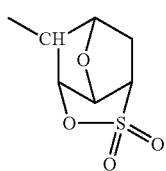 (3-1-18)
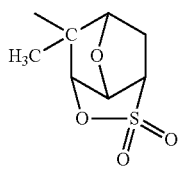 (3-1-19)
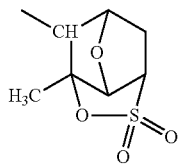 (3-1-20)
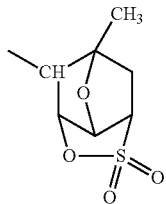 (3-1-21)
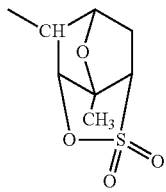 (3-1-22)
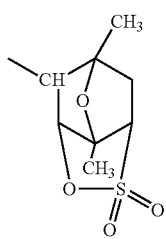 (3-1-23)
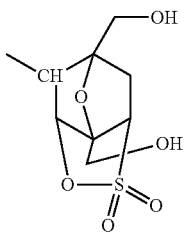 (3-1-24)
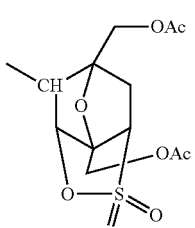 (3-1-25)
[Chemical Formula 27]
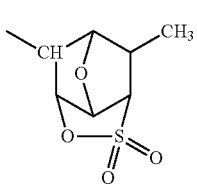 (3-1-26)
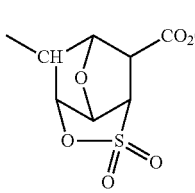 (3-1-27)
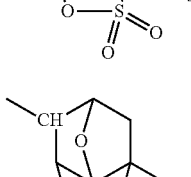 (3-1-28)
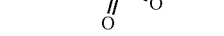 (3-1-29)
 (3-1-30)
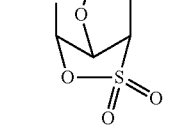 (3-1-31)

(3-1-32)
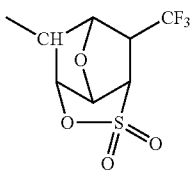

(3-1-33)
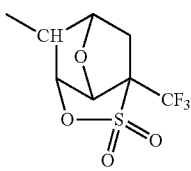

[Chemical Formula 28]

(3-2-1)
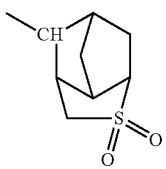

(3-2-2)
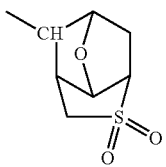

(3-3-1)
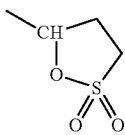

(3-4-1)
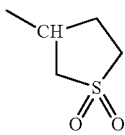

Of the groups shown above, the —$SO_2$-containing cyclic group is preferably a group represented by general formula (3-1), more preferably at least one group selected from the group consisting of groups represented by the above chemical formulas (3-1-1), (3-1-18), (3-3-1) and (3-4-1), and most preferably a group represented by chemical formula (3-1-1).

More specific examples of the structural unit ($a2^S$) include structural units represented by general formula (a2-0) shown below.

[Chemical Formula 29]

(a2-0)
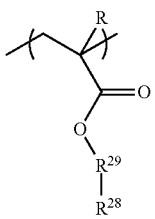

In the formula, R represents a hydrogen atom, an alkyl group of 1 to 5 carbon atoms or a halogenated alkyl group of 1 to 5 carbon atoms, $R^{28}$ represents an —$SO_2$-containing cyclic group, and $R^{29}$ represents a single bond or a divalent linking group.

In the formula (a2-0), R is the same as defined above.

$R^{28}$ is the same as the —$SO_2$-containing cyclic group described above.

$R^{29}$ may be either a single bond or a divalent linking group. A divalent linking group is preferable in terms of achieving superior effects for the present invention.

There are no particular limitations on the divalent linking group for $R^{29}$, and examples include the same groups as those described below for Y in formula (b1-2). Among these groups, an alkylene group or a group containing an ester linkage (—C(=O)—O—) is preferred.

The alkylene group is preferably a linear or branched alkylene group. Specific examples include the same groups as the linear alkylene groups and branched alkylene groups described above for the aliphatic hydrocarbon group for $Y^2$.

As the divalent linking group containing an ester linkage, groups represented by general formula: —$R^{30}$—C(=O)—O— (wherein $R^{30}$ represents the divalent linking group) are preferred. In other words, the structural unit ($a2^S$) is preferably a structural unit represented by general formula (a2-0-1) shown below.

[Chemical Formula 30]

(a2-0-1)
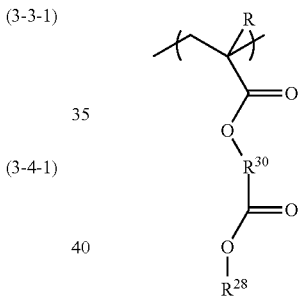

In the formula, R and $R^{28}$ are each the same as defined above, and $R^{30}$ is a divalent linking group.

There are no particular limitations on $R^{30}$, and the same groups as the divalent linking groups described below for Y in formula (b1-2) may be used.

As the divalent linking group for $R^{30}$, a linear or branched alkylene group, a divalent alicyclic hydrocarbon group, or a divalent linking group containing a hetero atom is preferred.

Examples of the linear or branched alkylene group, divalent alicyclic hydrocarbon group, and divalent linking group containing a hetero atom include the same linear or branched alkylene groups, divalent alicyclic hydrocarbon groups, and divalent linking groups containing a hetero atom as those described below as preferred groups for Y.

Of the above groups, a linear or branched alkylene group, or a divalent linking group containing an oxygen atom as a hetero atom is preferred.

As the linear alkylene group, a methylene group or ethylene group is preferred, and a methylene group is particularly desirable.

As the branched alkylene group, an alkylmethylene group or alkylethylene group is preferred, and —CH($CH_3$)—, —C($CH_3$)$_2$— and —C($CH_3$)$_2$$CH_2$— are particularly desirable.

The divalent linking group containing an oxygen atom is preferably a divalent linking group containing an ether linkage or an ester linkage, and is more preferably a group represented by a formula -A-O—B—, -[A-C(=O)—O]$_m$—B— or -A-O—C(=O)—B—.

Among these, groups represented by -A-O—C(=O)—B— are preferred, and groups represented by —(CH$_2$)$_c$—C(=O)—O—(CH$_2$)$_d$— are particularly desirable. c represents an integer of 1 to 5, and is preferably 1 or 2. d represents an integer of 1 to 5, and is preferably 1 or 2.

As the structural unit (a2$^S$), structural units represented by general formula (a0-1-11) or (a0-1-12) shown below are preferred, and structural units represented by formula (a0-1-12) are particularly desirable.

[Chemical Formula 31]

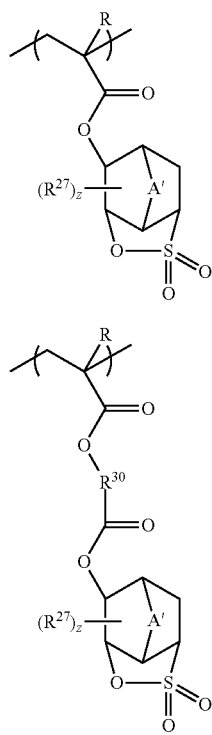

(a0-1-11)

(a0-1-12)

In the formulas, R, A', R$^{27}$, z and R$^{30}$ are each the same as defined above.

In formula (a0-1-11), A' is preferably a methylene group, an oxygen atom (—O—) or a sulfur atom (—S—).

R$^{30}$ is preferably a linear or branched alkylene group, or a divalent linking group containing an oxygen atom. Examples of the linear or branched alkylene group, and the divalent linking group containing an oxygen atom for R$^{30}$ include the same linear or branched alkylene groups, and divalent linking groups containing an oxygen described above.

As the structural unit represented by formula (a0-1-12), structural units represented by general formula (a0-1-12a) and (a0-1-12b) shown below are particularly desirable.

[Chemical Formula 32]

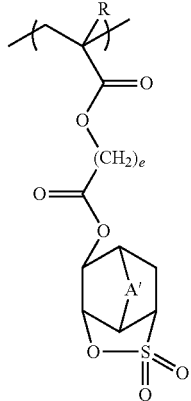

(a0-1-12a)

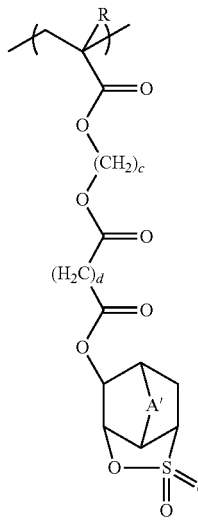

(a0-1-12b)

In the formulas, R and A' are each the same as defined above, and each of c to e independently represents an integer of 1 to 3.

Structural Unit (a2$^L$)

The structural unit (a2$^L$) is a structural unit derived from an acrylate ester which contains a lactone-containing cyclic group and may have an atom other than a hydrogen atom or a substituent bonded to the carbon atom on the α-position.

In this description, the term "lactone-containing cyclic group" refers to a cyclic group including a ring (lactone ring) containing an —O—C(O)— moiety within the ring structure. The lactone ring is counted as the first ring, and a lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

There are no particular limitations on the lactone-containing cyclic group within the structural unit (a2$^L$), and an arbitrary lactone-containing cyclic group may be used. Specific examples of lactone-containing monocyclic groups include groups in which one hydrogen atom has been removed from a 4- to 6-membered lactone ring, including a group in which one hydrogen atom has been removed from β-propiolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

Examples of the structural unit ($a2^L$) include structural units of the above general formula (a2-0) in which $R^{28}$ has been substituted with a lactone-containing cyclic group, and more specific examples include structural units represented by general formulas (a2-1) to (a2-5) shown below.

[Chemical Formula 33]

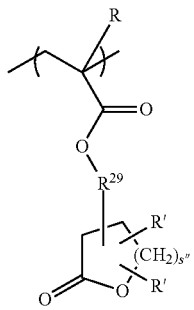
(a2-1)

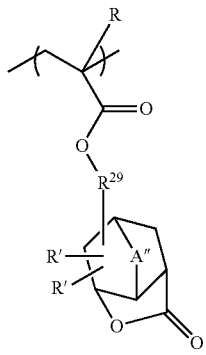
(a2-2)

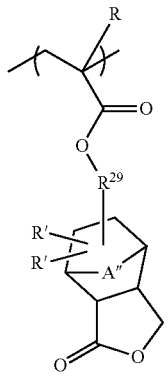
(a2-3)

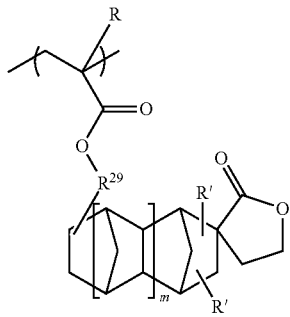
(a2-4)

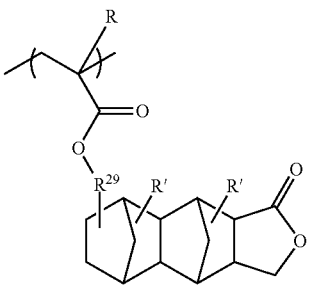
(a2-5)

In the formulas, R represents a hydrogen atom, an alkyl group of 1 to 5 carbon atoms or a halogenated alkyl group of 1 to 5 carbon atoms, each R' independently represents a hydrogen atom, an alkyl group of 1 to 5 carbon atoms, an alkoxy group of 1 to 5 carbon atoms or —COOR", wherein R" represents a hydrogen atom or an alkyl group, $R^{29}$ represents a single bond or a divalent linking group, s" represents an integer of 0 to 2, A" represents an oxygen atom, a sulfur atom or an alkylene group of 1 to 5 carbon atoms which may contain an oxygen atom or a sulfur atom, and m represents 0 or 1.

In general formulas (a2-1) to (a2-5), R is the same as defined above for R in the structural unit (a1).

Examples of the alkyl group of 1 to 5 carbon atoms for R' include a methyl group, ethyl group, propyl group, n-butyl group and tert-butyl group.

Examples of the alkoxy group of 1 to 5 carbon atoms for R' include a methoxy group, ethoxy group, n-propoxy group, iso-propoxy group, n-butoxy group and tert-butoxy group.

In terms of factors such as industrial availability, R' is preferably a hydrogen atom.

The alkyl group for R" may be a linear, branched or cyclic alkyl group.

When R" is a linear or branched alkyl group, the alkyl group preferably contains 1 to 10 carbon atoms, and more preferably 1 to 5 carbon atoms When R" is a cyclic alkyl group, the alkyl group preferably contains 3 to 15 carbon atoms, more preferably 4 to 12 carbon atoms, and most preferably 5 to 10 carbon atoms. Examples include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

Examples of A" include the same groups as those described above for A' in general formula (3-1). A" is preferably an alkylene group of 1 to 5 carbon atoms, an oxygen atom (—O—) or a sulfur atom (—S—), and is more preferably an alkylene group of 1 to 5 carbon atoms or —O—. As the alkylene group of 1 to 5 carbon atoms, a methylene group or dimethylmethylene group is preferable, and a methylene group is the most desirable.

$R^{29}$ is the same as defined above for $R^{29}$ in general formula (a2-0).

In formula (a2-1), s" is preferably 1 or 2.

Specific examples of the structural units represented by general formulas (a2-1) to (a2-5) are shown below. In each of the following formulas, $R^\alpha$ represents a hydrogen atom, a methyl group or a trifluoromethyl group.

[Chemical Formula 34]
(a2-1-1) 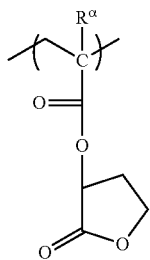
(a2-1-2) 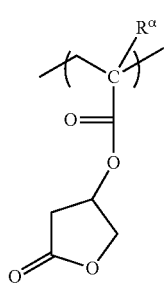
(a2-1-3) 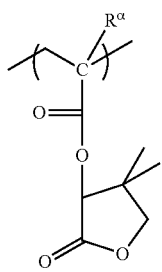
(a2-1-4) 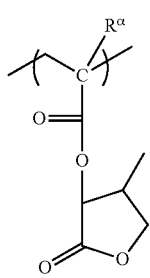
(a2-1-5) 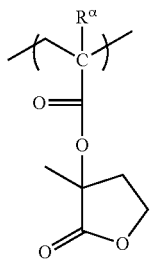
(a2-1-6) 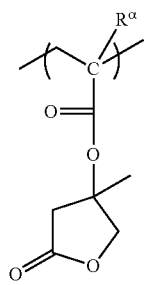
(a2-1-7) 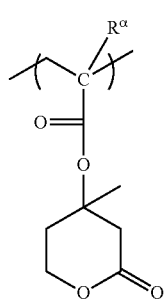
(a2-1-8) 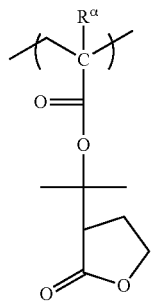
(a2-1-9) 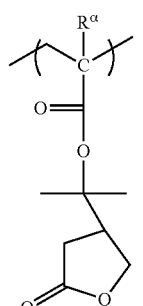
(a2-1-10) 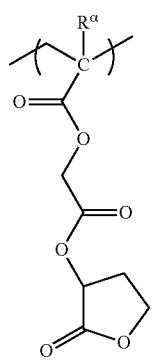

(a2-1-11)
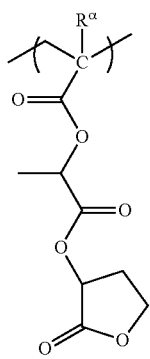
(a2-1-12)
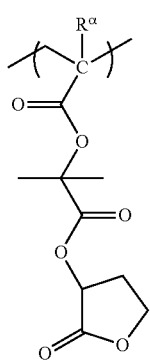
(a2-1-13)
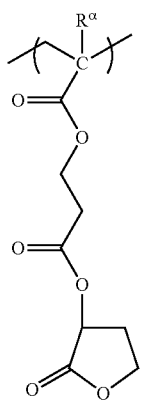
[Chemical Formula 35]
(a2-2-1)
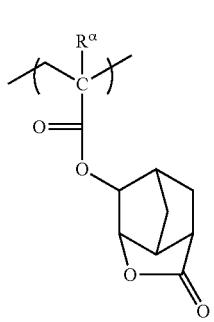
(a2-2-2)
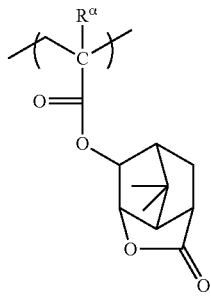
(a2-2-3)
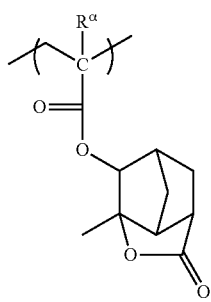
(a2-2-4)
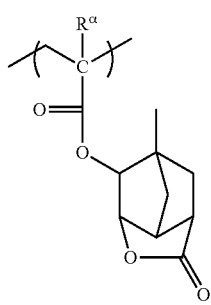
(a2-2-5)
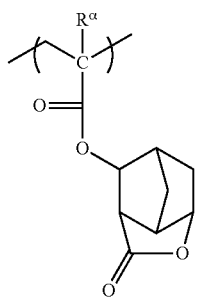
(a2-2-6)
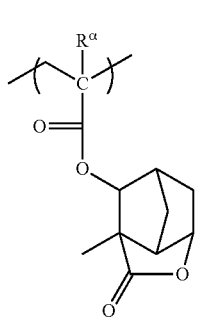

(a2-2-7) 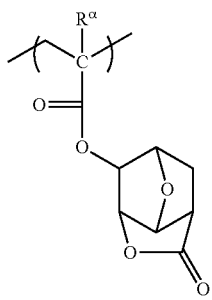
(a2-2-8) 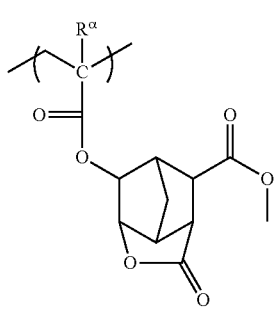
(a2-2-9) 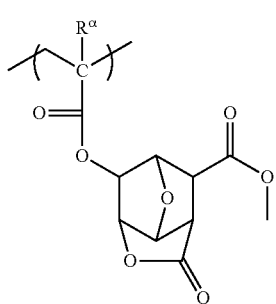
(a2-2-10) 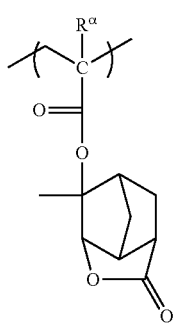
(a2-2-11) 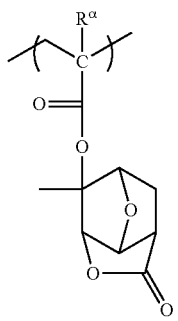
(a2-2-12) 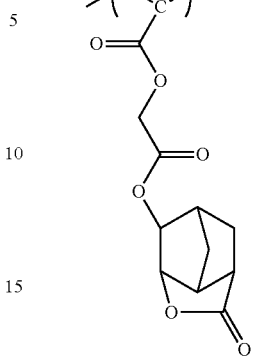
(a2-2-13) 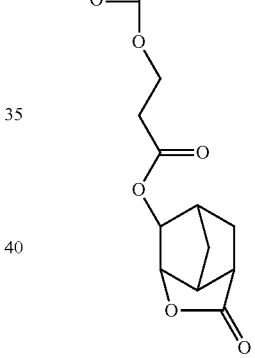
(a2-2-14) 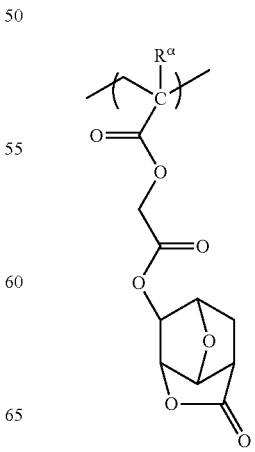

(a2-2-15)
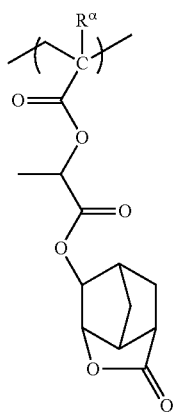
(a2-2-16)
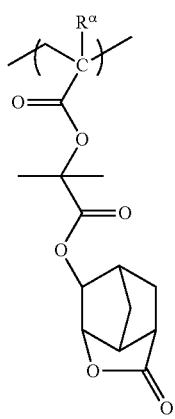
(a2-2-17)
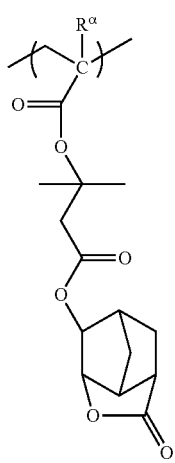
[Chemical Formula 36]
(a2-3-1)
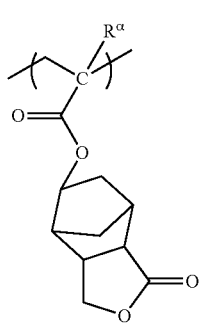
(a2-3-2)
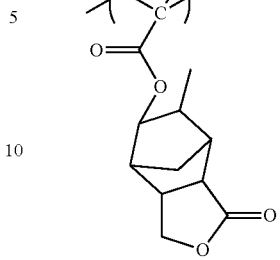
(a2-3-3)
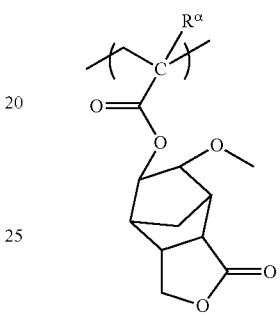
(a2-3-4)
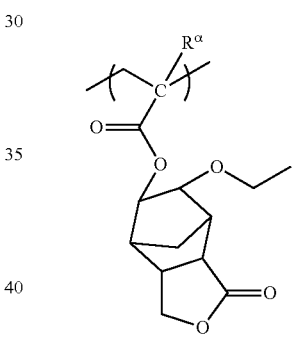
(a2-3-5)
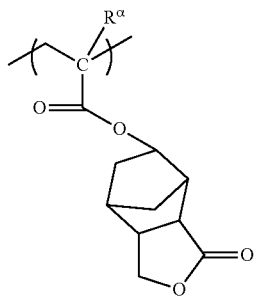
[Chemical Formula 37]
(a2-4-1)
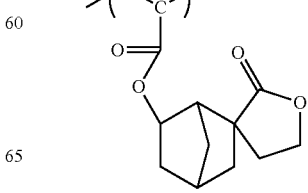

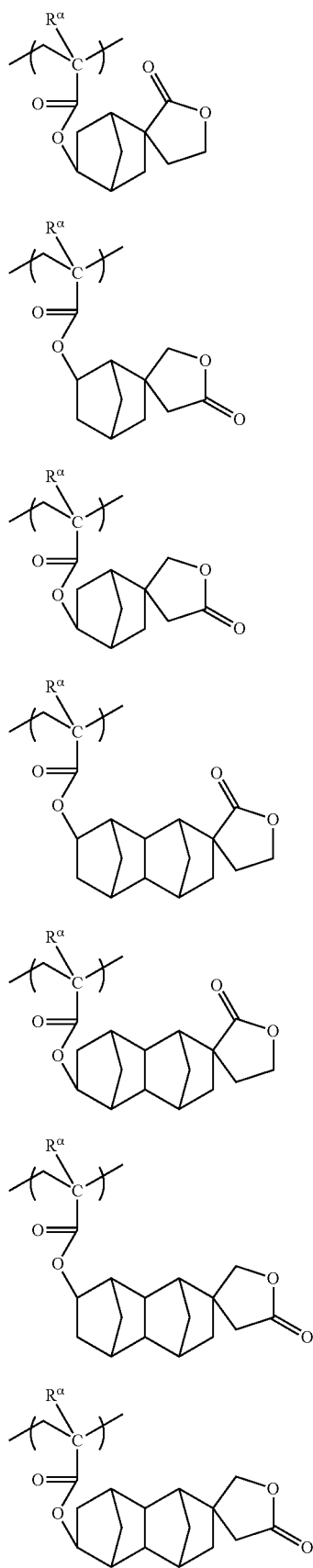
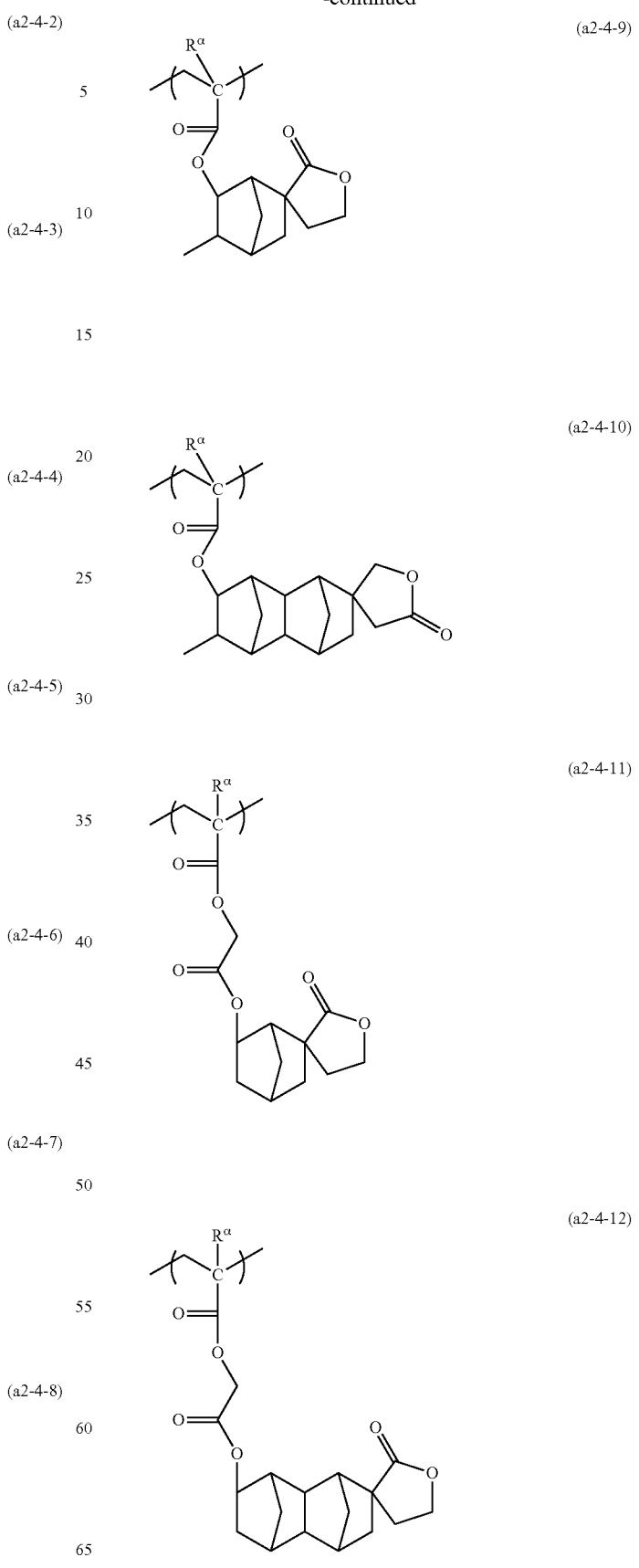

[Chemical Formula 38]

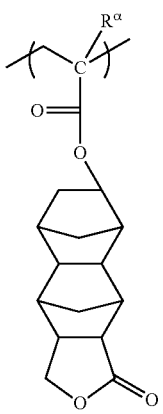 (a2-5-1)

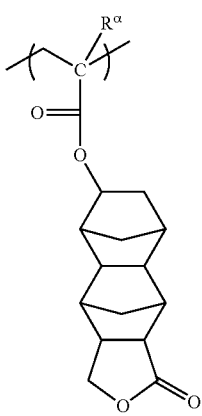 (a2-5-2)

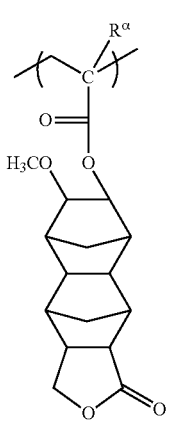 (a2-5-3)

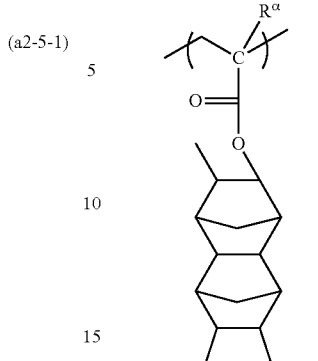 (a2-5-4)

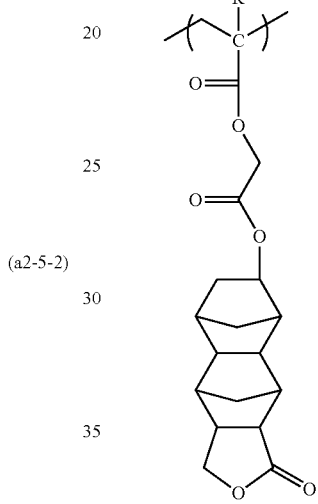 (a2-5-5)

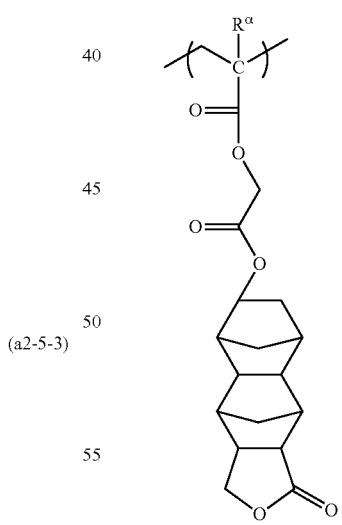 (a2-5-6)

The structural unit (a2$^L$) is preferably at least one structural unit selected from the group consisting of structural units represented by general formulas (a2-1) to (a2-5), is more preferably at least one structural unit selected from the group consisting of structural units represented by general formulas (a2-1) to (a2-3), and is still more preferably at least one structural unit selected from the group consisting of structural units represented by general formulas (a2-1) and (a2-2).

Among these structural units, the structural unit (a2$^L$) is preferably at least one structural unit selected from the group consisting of structural units represented by the above formulas (a2-1-1), (a2-1-2), (a2-2-1), (a2-2-7), (a2-2-12), (a2-2-14), (a2-3-1) and (a2-3-5).

In the component (A1), as the structural unit (a2), one type of structural unit may be used alone, or two or more types may be used in combination. For example, the structural unit (a2$^S$) may be used alone as the structural unit (a2), the structural unit (a2$^L$) may be used alone, or the structural units (a2$^S$) and (a2$^L$) may be used in combination. Further, as the structural unit (a2$^S$) or the structural unit (a2$^L$), one type of structural unit may be used alone, or two or more types may be used in combination.

In the present invention, in terms of achieving superior effects for the present invention, the structural unit (a2) preferably includes at least the structural unit (a2$^S$).

The amount of the structural unit (a2) within the component (A1), based on the combined total of all the structural units that constitute the component (A1), is preferably within a range from 1 to 80 mol %, more preferably from 10 to 70 mol %, still more preferably from 10 to 65 mol %, and most preferably from 10 to 60 mol %. Ensuring that the amount of the structural unit (a2) is at least as large as the lower limit of the aforementioned range enables the effects achieved be including the structural unit (a2) to be satisfactorily realized, whereas by ensuring that the amount is not more than the upper limit of the above range, a good balance can be achieved with the other structural units, and lithography properties such as DOF and CDU and the pattern shape can all be improved.

(Structural Unit (a3))

The structural unit (a3) is a structural unit derived from an acrylate ester which contains a polar group-containing aliphatic hydrocarbon group and may have an atom other than a hydrogen atom or a substituent bonded to the carbon atom on the α-position.

When the component (A1) includes the structural unit (a3), the hydrophilicity of the component (A) is improved, which contributes to a favorable improvement in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 39]

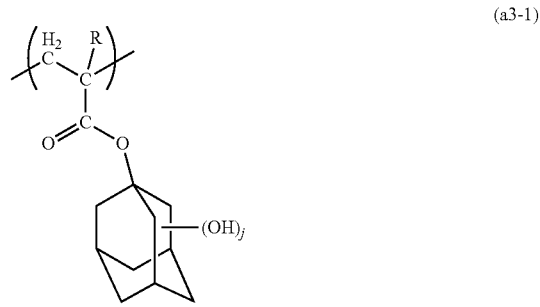

(a3-1)

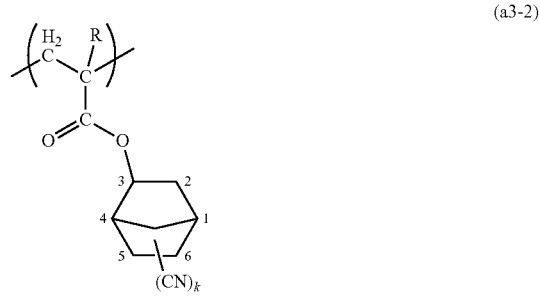

(a3-2)

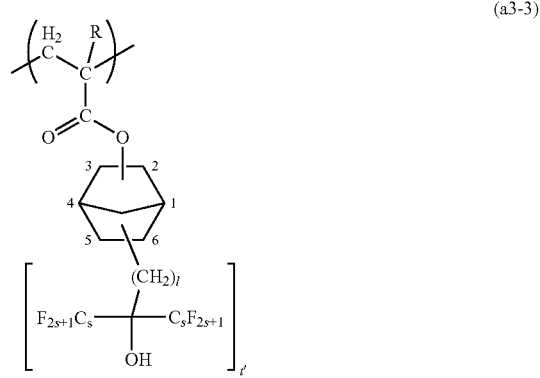

(a3-3)

In the formulas, R is the same as defined above, j is an integer of 1 to 3, k is an integer of 1 to 3, t' is an integer of 1 to 3, l is an integer of 1 to 5, and s is an integer of 1 to 3.

In formula (a3-1), j is preferably 1 or 2, and more preferably 1. When j is 2, it is preferable that the hydroxyl groups are bonded to the 3rd and 5th positions of the adamantyl group. When j is 1, it is preferable that the hydroxyl group is bonded to the 3rd position of the adamantyl group.

j is preferably 1, and it is particularly desirable that the hydroxyl group is bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group is bonded to the terminal of the carboxyl group of the acrylic acid. The fluorinated alkyl alcohol is preferably bonded to the 5th or 6th position of the norbornyl group.

As the structural unit (a3), one type of structural unit may be used alone, or two or more types may be used in combination.

The amount of the structural unit (a3) within the component (A1), based on the combined total of all the structural units that constitute the component (A1), is preferably within a range from 1 to 50 mol %, more preferably from 3 to 45 mol %, and still more preferably from 5 to 40 mol %. Ensuring that the amount of the structural unit (a3) is at least as large as the lower limit of the aforementioned range enables the effects achieved be including the structural unit (a3) to be satisfactorily realized, whereas by ensuring that the amount is not more than the upper limit of the above range, a good balance can be achieved with the other structural units.

(Other Structural Units)

The component (A1) may also include a structural unit (hereinafter referred to as "structural unit (a4)") which is other than the aforementioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

Preferred examples of the structural unit (a4) include structural units derived from an acrylate ester which contains a non-acid-dissociable aliphatic polycyclic group and may have an atom other than a hydrogen atom or a substituent bonded to the carbon atom on the α-position, and structural units derived from a styrene monomer or vinylnaphthalene monomer. Examples of the above polycyclic group include the same groups as those described above in connection with the structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 40]

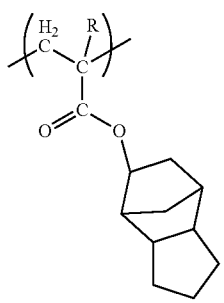

(a4-1)

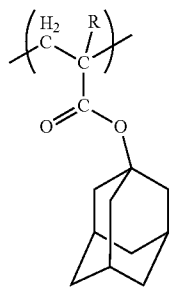

(a4-2)

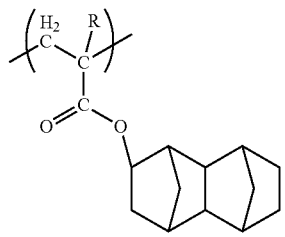

(a4-3)

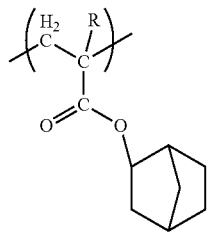

(a4-4)

(a4-5)

In the formulas, R is the same as defined above.

As the structural unit (a4), one type of structural unit may be used alone, or two or more types may be used in combination.

When the structural unit (a4) is included in the component (A1), the amount of the structural unit (a4), based on the combined total of all the structural units that constitute the component (A1), is preferably within the range from 1 to 20 mol %, more preferably from 1 to 15 mol %, and still more preferably from 1 to 10 mol %.

The component (A1) is preferably a copolymer containing the structural unit (a1).

Examples of such copolymers include copolymers consisting of the structural units (a1) and (a3), copolymers consisting of the structural units (a1) and (a2), and copolymers consisting of the structural units (a1), (a2) and (a3).

In the present invention, as the component (A1), copolymers including the structural unit combinations shown below in general formulas (A1-11) and (A1-12) are preferred. In the general formulas below, R, $R^{29}$, s''', $R^{11}$, j, e, A', $R^{12}$ and h are each the same as defined above, and the plurality of R groups in the formulas may be the same or different from each other.

[Chemical Formula 41]

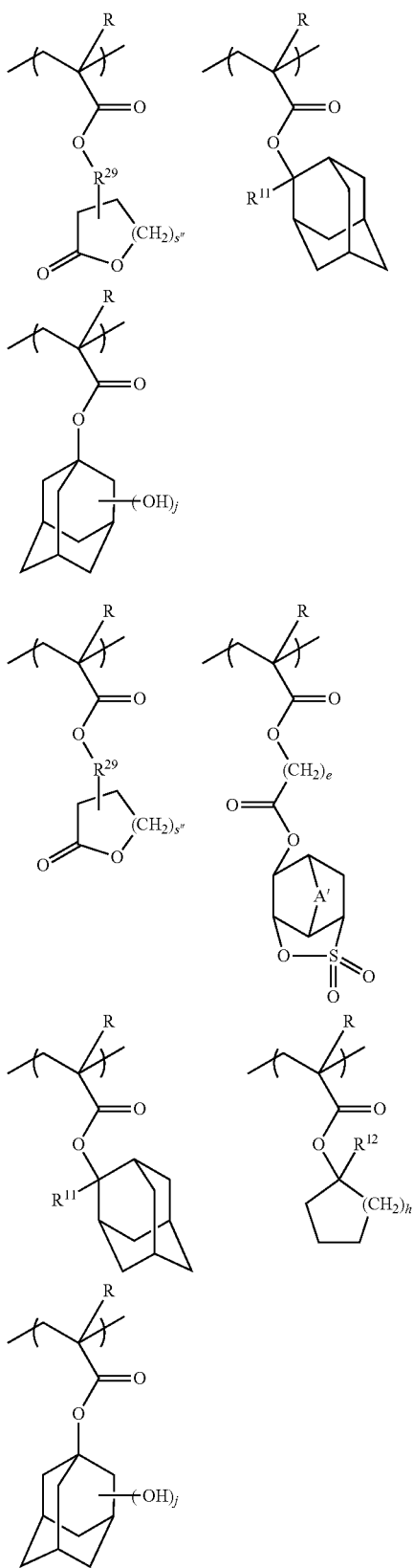

(A1-11)

(A1-12)

The weight-average molecular weight (Mw) (the polystyrene equivalent value determined by gel permeation chromatography) of the component (A1) is not particularly limited, but is preferably within a range from 1,000 to 50,000, more preferably from 1,500 to 30,000, and most preferably from 2,500 to 20,000. By ensuring that the weight average molecular weight is not more than the upper limit of the aforementioned range, the polymeric compound (A1) exhibits satisfactory solubility in a resist solvent when used as a resist, whereas by ensuring that the weight average molecular weight is at least as large as the lower limit of the aforementioned range, dry etching resistance and the cross-sectional shape of the resist pattern are improved.

Further, although there are no particular limitations on the dispersity (Mw/Mn) of the component (A1), the dispersity is preferably from 1.0 to 5.0, more preferably from 1.0 to 3.0, and most preferably from 1.2 to 2.5. Here, Mn is the number-average molecular weight.

In the component (A), either a single component (A1) may be used alone, or two or more different types of the component (A1) may be used in combination.

The amount of the component (A1) within the component (A), based on the total weight of the component (A), is preferably not less than 25% by weight, more preferably 50% by weight or more, and still more preferably 75% by weight or more. The amount of the component (A1) may also represent 100% by weight of the component (A). Provided the amount is not less than 25% by weight, effects such as an improvement in the lithography properties can be obtained.

[Component (A2)]

The component (A2) is preferably a low molecular weight compound that has a molecular weight of at least 500 but less than 2,500, contains a hydrophilic group, and also contains an acid-dissociable group as described above in connection with the component (A1).

Specific examples of the component (A2) include compounds containing a plurality of phenol structures in which some of the hydrogen atoms of the hydroxyl groups have been substituted with the aforementioned acid-dissociable groups.

Examples of the component (A2) include low molecular weight phenolic compounds in which a portion of the hydroxyl group hydrogen atoms have been substituted with an aforementioned acid-dissociable group. These types of compounds are known, for example, as sensitizers or heat resistance improvers for use in non-chemically amplified g-line or i-line resists, and any of these compounds may be used.

Examples of these low molecular weight phenolic compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers to hexamers of formalin condensation products of phenols such as phenol, m-cresol, p-cresol and xylenol. Needless to say, the low molecular weight phenol compound is not limited to these examples. Phenolic compounds having from 2 to 6 triphenylmethane structures are particularly preferred, as they yield superior levels of resolution and LWR.

There are no particular limitations on the acid-dissociable group, and examples include the groups described above.

A single component (A2) may be used alone, or two or more different types of the component (A2) may be used in combination.

In the resist composition of the present invention, a single component (A) may be used alone, or two or more different types of the component (A) may be used in combination.

Of the various possibilities, the component (A) preferably includes the component (A1).

In the resist composition of the present invention, the amount of the component (A) can be adjusted appropriately depending on factors such as the thickness of the resist film that is to be formed.

<Component (B)>

In the resist composition of the present invention, the component (B) includes an acid generator (B1) (hereinafter referred to as "component (B1)") having a group represented by general formula (b1-1) shown below in the cation moiety.

[Chemical Formula 42]

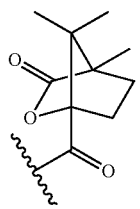

(b1-1)

There are no particular limitations on the component (B1) in the present invention, provided it contains a group represented by the above formula (b1-1), and for example, compounds having a group represented by formula (b1-1) as a substituent within the cation moiety of a sulfonium salt or iodonium salt used in conventional onium salt acid generators may be used.

Of the various possibilities, compounds represented by formula (b1-2) shown below are preferred as the component (B1) of the present invention.

[Chemical Formula 43]

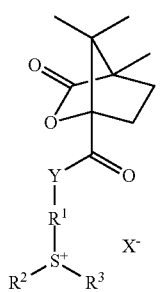

(b1-2)

In the formula, Y represents a divalent linking group, $R^1$ represents an arylene group which may have a substituent, each of $R^2$ and $R^3$ independently represents an organic group, $R^2$ and $R^3$ may be bonded to each other to form a ring with the sulfur atom in the formula, and $X^-$ represents a counter anion.

(Cation Moiety of Compound Represented by Formula (b1-2))

In formula (b1-2), Y represents a divalent linking group.

As the divalent linking group for Y, a divalent hydrocarbon group which may have a substituent or a divalent linking group containing a hetero atom or the like is preferred.

The expression that the hydrocarbon group "may have a substituent" means that some or all of the hydrogen atoms within the hydrocarbon group may each be substituted with a group or atom other than a hydrogen atom.

The hydrocarbon group may be an aliphatic hydrocarbon group or an aromatic hydrocarbon group. An "aliphatic hydrocarbon group" refers to a hydrocarbon group that has no aromaticity.

The aliphatic hydrocarbon group may be either saturated or unsaturated, but in most cases, is preferably saturated.

More specific examples of the aliphatic hydrocarbon group for the hydrocarbon group for Y include linear or branched aliphatic hydrocarbon groups and aliphatic hydrocarbon groups that include a ring within the structure.

The linear and branched aliphatic hydrocarbon groups preferably contain 1 to 10 carbon atoms, and more preferably 1 to 8 carbon atoms, still more preferably 1 to 5 carbon atoms, and most preferably 1 or 2 carbon atoms.

As the linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—, alkylethylene groups such as —CH($CH_3$)$CH_2$—, —CH($CH_3$)CH($CH_3$)—, —C($CH_3$)$_2CH_2$—, —CH($CH_2CH_3$)$CH_2$— and —C($CH_2CH_3$)$_2$—$CH_2$—, alkyltrimethylene groups such as —CH($CH_3$)$CH_2CH_2$— and —$CH_2$CH($CH_3$)$CH_2$—, and alkyltetramethylene groups such as —CH($CH_3$)$CH_2CH_2CH_2$— and —$CH_2$CH($CH_3$)$CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Examples of the aliphatic hydrocarbon groups that include a ring within the structure include cyclic aliphatic hydrocarbon groups (groups in which two hydrogen atoms have been removed from an aliphatic hydrocarbon ring), and groups in which the cyclic aliphatic hydrocarbon group is bonded to the terminal of an aforementioned chain-like aliphatic hydrocarbon group or interposed within the chain of an aforementioned chain-like aliphatic hydrocarbon group.

The cyclic aliphatic hydrocarbon group preferably contains 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

Examples of the aromatic hydrocarbon group for the hydrocarbon group for Y include divalent aromatic hydrocarbon groups in which an additional hydrogen atom has been removed from the aromatic hydrocarbon nucleus of a monovalent aromatic hydrocarbon group such as a phenyl group, biphenylyl group, fluorenyl group, naphthyl group, anthryl group or phenanthryl group; aromatic hydrocarbon groups in which some of the carbon atoms that constitute the ring of an aforementioned divalent aromatic hydrocarbon group have been substituted with a hetero atom such as an oxygen atom, sulfur atom or nitrogen atom; and aromatic hydrocarbon groups in which an additional hydrogen atom has been removed from the aromatic hydrocarbon nucleus of an arylalkyl group such as a benzyl group, phenethyl group, 1-naphthylmethyl group, 2-naphthylmethyl group, 1-naphthylethyl group or 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

In the "divalent linking group containing a hetero atom" for Y, the hetero atom is an atom other than a carbon atom or hydrogen atom, and examples include an oxygen atom, a nitrogen atom, a sulfur atom and a halogen atom.

Specific examples of divalent linking groups containing a hetero atom include —O—, —C(=O)—, —C(=O)—O—, a carbonate linkage (—O—C(=O)—O—), —NH—, —NR$^{04}$— (wherein R$^{04}$ represents an alkyl group), —NH—C(=O)—, and =N—. Further, combinations of any of these divalent linking groups containing a hetero atom with a divalent hydrocarbon group can also be used. Examples of the divalent hydrocarbon group include the same groups as those described above for the hydrocarbon group which may have a substituent, although a linear or branched aliphatic hydrocarbon group or an aliphatic hydrocarbon group that includes a ring within the structure is preferable.

Y may or may not include an acid-dissociable portion within the structure.

An "acid-dissociable portion" refers to a portion within the organic group which is dissociated from the organic group under the action of the acid generated upon exposure. When Y has an acid-dissociable portion, it preferably has an acid-dissociable portion having a tertiary carbon atom.

In the present invention, Y is preferably a single bond, an alkylene group, a divalent aliphatic cyclic group or a divalent linking group containing a hetero atom, and is more preferably a single bond, an alkylene group or a divalent linking group containing a hetero atom.

When Y represents an alkylene group, the alkylene group preferably contains 1 to 10 carbon atoms, more preferably 1 to 6 carbon atoms, still more preferably 1 to 4 carbon atoms, and most preferably 1 to 3 carbon atoms. Specific examples of the alkylene group include the linear alkylene groups and branched alkylene groups mentioned above.

When Y represents a divalent aliphatic cyclic group, examples of the aliphatic cyclic group include the same groups as those described above for the "aliphatic hydrocarbon group that includes a ring within the structure".

As the aliphatic cyclic group, a group in which two or more hydrogen atoms have been removed from cyclopentane, cyclohexane, norbornane, isobornane, adamantane, tricyclodecane or tetracyclododecane is particularly desirable.

When Y represents a divalent linking group containing a hetero atom, examples of preferred linking groups include —O—, —C(=O)—O—, —C(=O)—, —O—C(=O)—O—, —C(=O)—NH—, —NH— (wherein H may be replaced with a substituent such as an alkyl group or an acyl group), —S—, —S(=O)$_2$—, —S(=O)$_2$—O—, groups represented by general formulas -A-O—B—, —O-A-O—, —O-D-O—, —NH-A-O— (wherein H may be replaced with a substituent such as an alkyl group or an acyl group), -[A-C(=O)—O]$_m$—B—, -A-O—C(=O)—B— and —C(=O)—O—B— [wherein each of A, B and D independently represents a divalent hydrocarbon group which may have a substituent, O represents an oxygen atom, and m represents an integer of 0 to 3].

When Y represents —NH— or —NH-A-O—, H may be replaced with a substituent such as an alkyl group or an acyl group (aromatic group) or the like. The substituent (the alkyl group or acyl group or the like) preferably contains 1 to 10 carbon atoms, more preferably 1 to 8 carbon atoms, and most preferably 1 to 5 carbon atoms.

In the groups represented by general formulas -A-O—B—, —O-A-O—, —O-D-O—, —NH-A-O—, -[A-C(=O)—O]$_m$—B—, -A-O—C(=O)—B— and —C(=O)—O—B—, each of A, B and D independently represents a divalent hydrocarbon group which may have a substituent. Examples of these divalent hydrocarbon groups include the same groups as those described above for the "divalent hydrocarbon group which may have a substituent" for Y.

A is preferably a linear aliphatic hydrocarbon group, more preferably a linear alkylene group, still more preferably a linear alkylene group of 1 to 5 carbon atoms, and most preferably a methylene group or ethylene group.

B is preferably a linear or branched aliphatic hydrocarbon group, and is more preferably a methylene group, ethylene group or alkylmethylene group. The alkyl group within the alkylmethylene group is preferably a linear alkyl group of 1 to 5 carbon atoms, more preferably a linear alkyl group of 1 to 3 carbon atoms, and most preferably a methyl group.

D is preferably a linear aliphatic hydrocarbon group, an aliphatic hydrocarbon group that includes a ring within the structure, or a combination thereof, and a combination of a linear alkylene group of 1 to 5 carbon atoms and a group having two hydrogen atoms removed from a monocycloalkane of 3 to 6 carbon atoms is particularly desirable.

In the group represented by formula -[A-C(=O)—O]$_m$—B—, m represents an integer of 0 to 3, and is preferably an integer of 0 to 2, more preferably 0 or 1, and most preferably 1.

The divalent linking group containing a hetero atom is preferably a linear group containing an oxygen atom or nitrogen atom as the hetero atom, such as a group containing an ether linkage or an ester linkage, and is more preferably a group represented by one of the aforementioned formulas —O—, —NH—, —O-A-O—, —O-D-O—, —NH-A-O—, -A-O—B—, -[A-C(=O)—O]$_m$—B—, -A-O—C(=O)—B— or —C(=O)—O—B—.

Among these, groups represented by the formulas —O—, —NH—, —O-A-O—, —O-D-O—, —NH-A-O—, -A-O—B—, -[A-C(=O)—O]$_m$—B— or —C(=O)—O—B— are preferable, groups represented by the formulas —O—, —NH—, —O-A-O—, —O-D-O—, —NH-A-O—, -[A-C(=O)—O]$_m$—B— (wherein m is preferably 1) or —C(=O)—O—B— are more preferable, and groups represented by —O—, —NH—, —O—(CH$_2$)$_a$—O—, —NH—(CH$_2$)$_a$—O—, —O—(CH$_2$)$_a$-D$_1$-(CH$_2$)$_b$—O— (wherein D$_1$ represents an aliphatic cyclic group), —(CH$_2$)$_a$—C(=O)—O—(CH$_2$)$_b$— or —C(=O)—O—(CH$_2$)$_b$— are particularly desirable.

Each of a and b independently represents an integer of 1 to 10, preferably an integer of 1 to 8, more preferably an integer of 1 to 5, and most preferably 1 or 2.

In the present invention, Y is preferably a divalent linking group containing a hetero atom, is more preferably a group represented by one of the formulas —O—, —NH—, —O—(CH$_2$)$_a$—O—, —NH—(CH$_2$)$_a$—O— or —O—(CH$_2$)$_a$-D$_1$-(CH$_2$)$_b$—O— (wherein D$_1$ represents an aliphatic cyclic group), and is most preferably —O—.

In formula (b1-2), R$^1$ represents an arylene group which may have a substituent. The arylene group may have either a single substituent or a plurality of substituents.

There are no particular limitations on the arylene group for R1, and examples include arylene groups having 6 to 20 carbon atoms in which some or all of the hydrogen atoms of the arylene group may or may not be substituted with alkyl groups, alkoxy groups, halogen atoms or hydroxyl groups or the like.

This type of arylene group is preferably an arylene group of 6 to 10 carbon atoms, as such groups can be synthesized at low cost. Specific examples include a phenylene group and a naphthylene group, and a phenylene group is particularly desirable.

The alkyl group with which hydrogen atoms of the arylene group may be substituted is preferably an alkyl group of 1 to 5 carbon atoms, more preferably a methyl group, ethyl group, propyl group, n-butyl group or a tert-butyl group, and most preferably a methyl group.

The alkoxy group with which hydrogen atoms of the arylene group may be substituted is preferably an alkoxy group of 1 to 5 carbon atoms, and is more preferably a methoxy group, ethoxy group, n-propoxy group, iso-propoxy group, n-butoxy group or tert-butoxy group.

The halogen atom with which hydrogen atoms of the arylene group may be substituted is preferably a fluorine atom.

In formula (b1-2), each of R$^2$ and R$^3$ independently represents an organic group.

The organic groups of R$^2$ and R$^3$ are carbon-containing groups, which may also include atoms besides the carbon atoms (such as a hydrogen atom, oxygen atom, nitrogen atom, sulfur atom or halogen atom (such as a fluorine atom or chlorine atom) or the like).

As the organic groups for R$^2$ and R$^3$, aryl groups or alkyl groups are preferred.

There are no particular limitations on the aryl group for R$^2$ or R$^3$, and examples include aryl groups of 6 to 20 carbon atoms, wherein some or all of the hydrogen atoms of the aryl group may or may not be substituted with alkyl groups, alkoxy groups, halogen atoms or hydroxyl groups or the like.

This type of aryl group is preferably an aryl group of 6 to 10 carbon atoms, as such groups can be synthesized at low cost. Specific examples include a phenyl group and a naphthyl group, and a phenyl group is particularly desirable.

Examples of the alkyl groups, alkoxy groups and halogen atoms with which hydrogen atoms of the aryl group may be substituted include the same groups as those described above for the alkyl groups, alkoxy groups and halogen atoms with which hydrogen atoms of the aforementioned arylene group for R$^1$ may be substituted.

Further, structures in which a hydrogen atom of the aryl group of R$^2$ or R$^3$ is substituted with either a group represented by the above formula (b1-1), or a combination of a group represented by formula (b1-1) and Y from within the above formula (b1-2) are also preferred. In this case, the plurality of Y groups within the component (B1) of the present invention may be either the same or different from each other.

There are no particular limitations on the alkyl group for R$^2$ or R$^3$, and examples include linear, branched or cyclic alkyl groups of 1 to 10 carbon atoms. In terms of achieving excellent resolution, the alkyl group preferably has 1 to 5 carbon atoms. Specific examples include a methyl group, ethyl group, n-propyl group, isopropyl group, n-butyl group, isobutyl group, n-pentyl group, cyclopentyl group, hexyl group, cyclohexyl group, nonyl group and decanyl group. Among these, a methyl group is most preferable because it provides excellent resolution and enables synthesis to be performed at a low cost.

In formula (b1-2), R$^2$ and R$^3$ may be bonded to each other to form a ring in combination with the sulfur atom in the formula.

In such cases, it is preferable that the ring that is formed is a 3- to 10-membered ring including the sulfur atom, and a 5- to 7-membered ring including the sulfur atom is particularly desirable.

The ring structure formed in combination with the sulfur atom may also include a hetero atom such as a sulfur atom or an oxygen atom (—O—, =O).

Specific examples of the ring that is formed include a benzene ring, naphthalene ring, anthracene ring, phenanthrene ring, fluorene ring, triphenylene ring, naphthacene ring, biphenyl ring, pyrrole ring, furan ring, thiophene ring, imidazole ring, oxazole ring, thiazole ring, pyridine ring, pyrazine ring, pyrimidine ring, pyridazine ring, indolizine ring, indole ring, benzofuran ring, benzothiophene ring, isobenzofuran ring, quinolidine ring, quinoline ring, phthalazine ring, naphthylidine ring, quinoxaline ring, quinoxazoline ring, isoquinoline ring, carbazole ring, phenanthridine ring, acridine ring, phenanthroline ring, thianthrene ring, chromene ring, xanthene ring, phenoxazine ring, phenothiazine ring, phenazine ring, tetrahydrothiophene ring or tetrahydrothiopyran ring.

Specific examples of preferred cation moieties for the compound represented by formula (b1-2) are shown below.

[Chemical Formula 44]

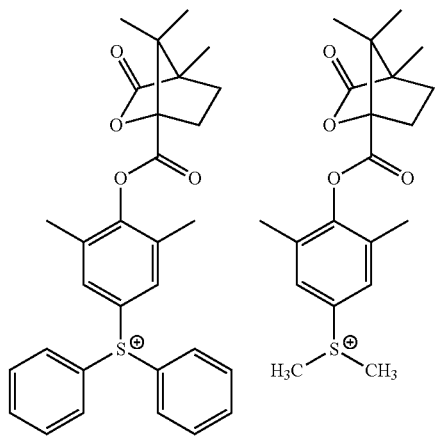

83
-continued
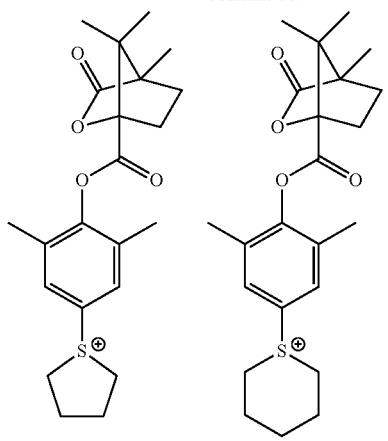
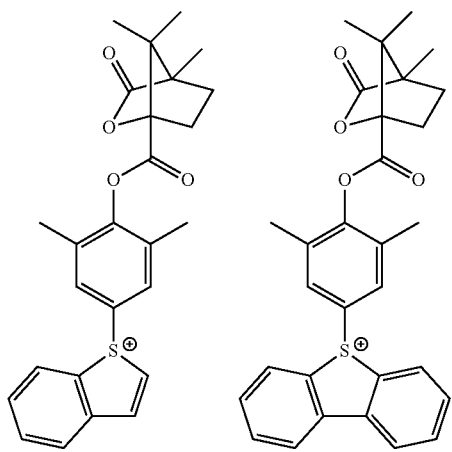
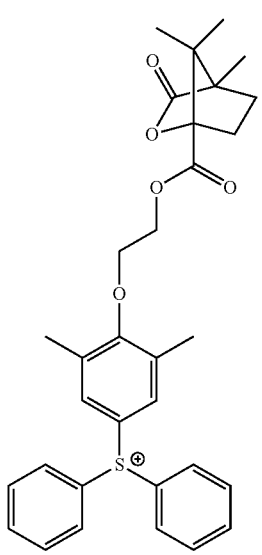
84
-continued
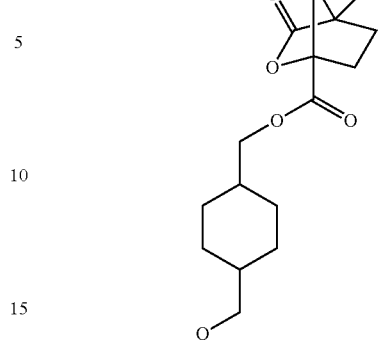
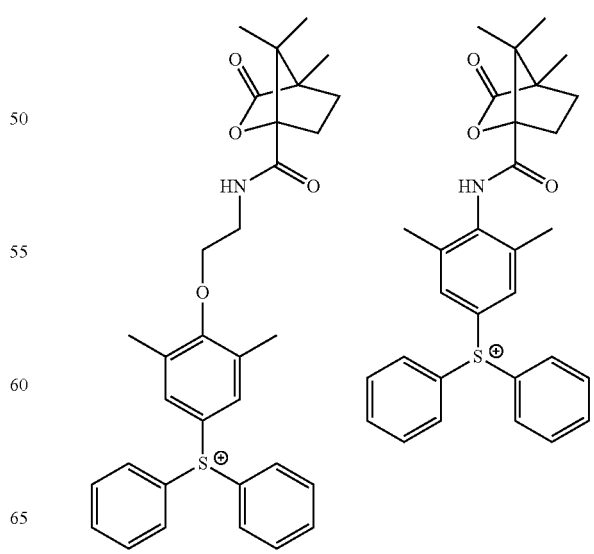

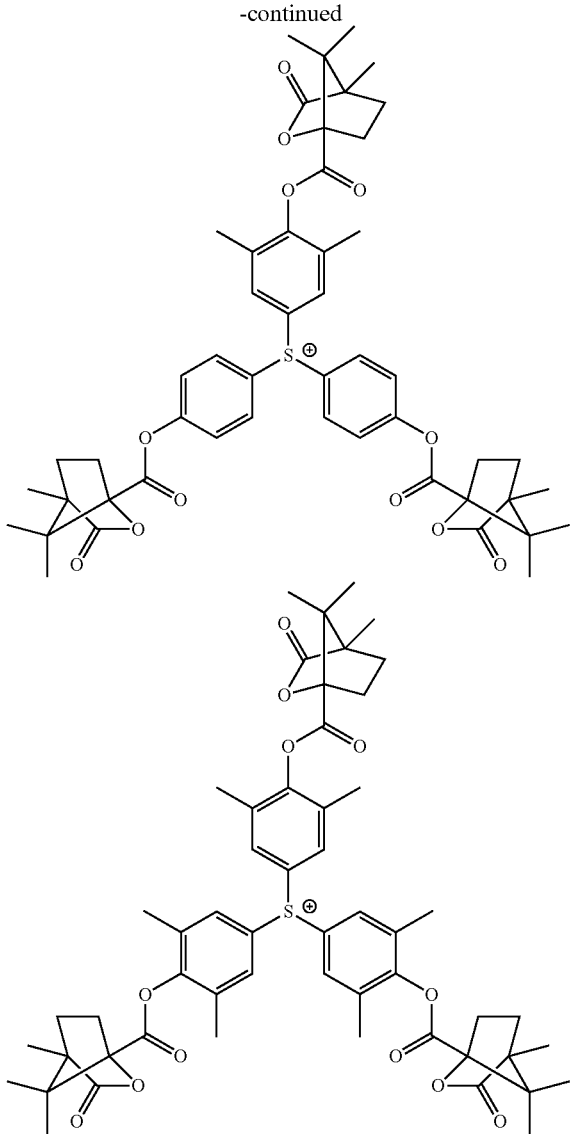

(Anion Moiety of Compound Represented by Formula (b1-2))

In formula (b1-2), X$^-$ represents a counter anion.

There are no particular limitations on the counter anion for X$^-$, and for example, any of the conventional anions known as anion moieties for onium salt acid generators may be used appropriately.

Examples of X$^-$ include anions represented by the general formula R$^{20}$SO$_3^-$ (wherein R$^{20}$ represents a linear, branched or cyclic alkyl group, a halogenated alkyl group, an aryl group or an alkenyl group, wherein the group may have a substituent).

In the general formula R$^{20}$SO$_3^-$, R$^{20}$ represents a linear, branched or cyclic alkyl group, a halogenated alkyl group, an aryl group or an alkenyl group, wherein the group may have a substituent.

The linear or branched alkyl group for R$^{20}$ is preferably a group of 1 to 10 carbon atoms, more preferably 1 to 8 carbon atoms, and most preferably 1 to 4 carbon atoms.

The cyclic alkyl group for R$^{20}$ is preferably a cyclic group of 4 to 15 carbon atoms, more preferably 4 to 10 carbon atoms, and most preferably 6 to 10 carbon atoms.

Examples of R$^{20}$SO$_3^-$ when R$^{20}$ is an alkyl group include alkylsulfonate ions such as methanesulfonate, n-propanesulfonate, n-butanesulfonate, n-octanesulfonate, 1-adamantanesulfonate, 2-norbornanesulfonate and d-camphor-10-sulfonate.

The halogenated alkyl group for R$^{20}$ is a group in which some or all of the hydrogen atoms within an alkyl group have been substituted with halogen atoms, wherein the alkyl group is preferably an alkyl group of 1 to 5 carbon atoms, is more preferably a linear or branched alkyl group, and is most preferably a methyl group, ethyl group, propyl group, isopropyl group, n-butyl group, tert-butyl group, tert-pentyl group, or isopentyl group. Examples of the halogen atoms used for substituting the hydrogen atoms include fluorine atoms, chlorine atoms, iodine atoms and bromine atoms.

In the halogenated alkyl group, it is preferable that 50 to 100% of all the hydrogen atoms within the alkyl group (the alkyl group prior to halogenation) are substituted with halogen atoms, and groups in which all of the hydrogen atoms have been substituted with halogen atoms are particularly desirable.

As the halogenated alkyl group, a fluorinated alkyl group is preferable. The fluorinated alkyl group is preferably a group of 1 to 10 carbon atoms, more preferably 1 to 8 carbon atoms, and most preferably 1 to 4 carbon atoms.

Furthermore, the fluorination ratio of the fluorinated alkyl group is preferably within a range from 10 to 100%, and more preferably from 50 to 100%. Groups in which all of the hydrogen atoms have been substituted with fluorine atoms are particularly desirable as they yield stronger acids.

Specific examples of these types of preferred fluorinated alkyl groups include a trifluoromethyl group, pentafluoro-n-propyl group and nonafluoro-n-butyl group.

The aryl group for R$^{20}$ is preferably an aryl group of 6 to 20 carbon atoms.

The alkenyl group for R$^{20}$ is preferably an alkenyl group of 2 to 10 carbon atoms.

The expression that R$^{20}$ "may have a substituent" means that some or all of the hydrogen atoms within the aforementioned linear, branched or cyclic alkyl group, halogenated alkyl group, aryl group or alkenyl group may be substituted with a substituent (an atom other than a hydrogen atom or a group).

The number of substituents within R$^{20}$ may be either 1, or 2 or more.

Examples of the substituent include a halogen atom, a hetero atom, an alkyl group, and a group represented by the formula X$^3$-Q$^1$- (wherein Q$^1$ represents a divalent linking group containing an oxygen atom, and X$^3$ represents a hydrocarbon group of 3 to 30 carbon atoms which may have a substituent).

Examples of the halogen atoms and alkyl groups include the same halogen atoms and alkyl groups as those described above with respect to the halogenated alkyl group for R$^{20}$.

Examples of the hetero atoms include an oxygen atom, a nitrogen atom, and a sulfur atom.

In the group represented by formula X$^3$-Q$^1$-, Q$^1$ represents a divalent linking group containing an oxygen atom.

Q$^1$ may also contain atoms other than the oxygen atom. Examples of these atoms other than the oxygen atom include a carbon atom, hydrogen atom, sulfur atom and nitrogen atom.

Examples of the divalent linking group containing an oxygen atom include non-hydrocarbon, oxygen atom-containing linking groups such as an oxygen atom (an ether bond, —O—), an ester linkage (—C(=O)—O—), an amide linkage (—C(=O)—NH—), a carbonyl group (—C(=O)—), a carbonate linkage (—O—C(=O)—O—), and combinations of these non-hydrocarbon, hetero atom-containing linking groups with an alkylene group. These combinations may also include an additional sulfonyl (—SO$_2$—) linkage.

Specific examples of the combinations of the aforementioned non-hydrocarbon, hetero atom-containing linking groups and an alkylene group include —R$^{91}$—O—, —R$^{92}$—O—C(=O)—, —C(=O)—O—R$^{93}$—O—C(=O)—, —SO$_2$—O—R$^{94}$—O—C(=O)—, and —R$^{95}$—SO$_2$—O—R$^{94}$—O—C(=O)— (wherein each of R$^{91}$ to R$^{95}$ independently represents an alkylene group).

The alkylene group for R$^{91}$ to R$^{95}$ is preferably a linear or branched alkylene group, and preferably contains 1 to 12 carbon atoms, more preferably 1 to 5 carbon atoms, and most preferably 1 to 3 carbon atoms.

Specific examples of alkylene groups include a methylene group [—CH$_2$—], alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—, an ethylene group [—CH$_2$CH$_2$—], alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—, a trimethylene group (n-propylene group) [—CH$_2$CH$_2$CH$_2$—], alkyltrimethylene groups such as —CH(CH$_3$)CH$_2$CH$_2$— and —CH$_2$CH(CH$_3$)CH$_2$—, a tetramethylene group [—CH$_2$CH$_2$CH$_2$CH$_2$—], alkyltetramethylene groups such as —CH(CH$_3$)CH$_2$CH$_2$CH$_2$— and —CH$_2$CH(CH$_3$)CH$_2$CH$_2$—, and a pentamethylene group [—CH$_2$CH$_2$CH$_2$CH$_2$CH$_2$—].

Q$^1$ is preferably a divalent linking group containing an ester linkage or ether linkage, and more preferably a group of —R$^{91}$—O—, —R$^{92}$—O—C(=O)— or —C(=O)—O—R$^{93}$—O—C(=O)—.

In the group represented by the formula X$^3$-Q$^1$-, the hydrocarbon group for X$^3$ may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within substituents is not included in the number of carbon atoms of the aromatic hydrocarbon group.

Specific examples of the aromatic hydrocarbon group include aryl groups, which are aromatic hydrocarbon rings having one hydrogen atom removed therefrom, such as a phenyl group, biphenylyl group, fluorenyl group, naphthyl group, anthryl group or phenanthryl group, and arylalkyl groups such as a benzyl group, phenethyl group, 1-naphthylmethyl group, 2-naphthylmethyl group, 1-naphthylethyl group or 2-naphthylethyl group. The alkyl chain within the arylalkyl group preferably has 1 to 4 carbon atoms, more preferably 1 or 2 carbon atoms, and most preferably 1 carbon atom.

The aromatic hydrocarbon group may have a substituent. For example, some of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Examples of the former case include heteroaryl groups in which some of the carbon atoms constituting the ring within an aforementioned aryl group have been substituted with a hetero atom such as an oxygen atom, a sulfur atom or a nitrogen atom, and heteroarylalkyl groups in which some of the carbon atoms constituting the aromatic hydrocarbon ring within an aforementioned arylalkyl group have been substituted with an aforementioned hetero atom.

In the latter case, examples of the substituent for the aromatic hydrocarbon group include an alkyl group, alkoxy group, halogen atom, halogenated alkyl group, hydroxyl group or oxygen atom (=O) or the like.

The alkyl group as the substituent for the aromatic hydrocarbon group is preferably an alkyl group of 1 to 5 carbon atoms, and a methyl group, ethyl group, propyl group, n-butyl group or tert-butyl group is the most desirable.

The alkoxy group as the substituent for the aromatic hydrocarbon group is preferably an alkoxy group of 1 to 5 carbon atoms, is more preferably a methoxy group, ethoxy group, n-propoxy group, iso-propoxy group, n-butoxy group or tert-butoxy group, and is most preferably a methoxy group or an ethoxy group.

Examples of the halogen atom as the substituent for the aromatic hydrocarbon group include a fluorine atom, chlorine atom, bromine atom and iodine atom, and a fluorine atom is preferable.

Examples of the halogenated alkyl group as the substituent for the aromatic hydrocarbon group include groups in which some or all of the hydrogen atoms within an aforementioned alkyl group have been substituted with aforementioned halogen atoms.

The aliphatic hydrocarbon group for X$^3$ may be either a saturated aliphatic hydrocarbon group or an unsaturated aliphatic hydrocarbon group. Further, the aliphatic hydrocarbon group may be linear, branched or cyclic.

In the aliphatic hydrocarbon group for X$^3$, some of the carbon atoms constituting the aliphatic hydrocarbon group may be substituted with a substituent containing a hetero atom, and/or some or all of the hydrogen atoms constituting the aliphatic hydrocarbon group may be substituted with a substituent containing a hetero atom.

There are no particular limitations on this "hetero atom" within X$^3$, provided it is an atom other than a carbon atom or a hydrogen atom. Examples of the hetero atom include a halogen atom, oxygen atom, sulfur atom and nitrogen atom.

Examples of the halogen atom include a fluorine atom, chlorine atom, iodine atom and bromine atom.

The substituent containing a hetero atom may consist solely of the hetero atom, or may be a group that also contains a group or atom other than a hetero atom.

Specific examples of the substituent for substituting some of the carbon atoms include —O—, —C(=O)—O—, —C(=O)—, —O—C(=O)—O—, —C(=O)—NH—, —NH— (wherein H may be replaced with a substituent such as an alkyl group or an acyl group), —S—, —S(=O)$_2$— and —S(=O)$_2$—O—. When the aliphatic hydrocarbon group is cyclic, any of these substituents may be included within the ring structure of the aliphatic hydrocarbon group.

Examples of the substituent for substituting some or all of the hydrogen atoms include an alkoxy group, halogen atom, halogenated alkyl group, hydroxyl group, oxygen atom (=O) and cyano group.

The alkoxy group is preferably an alkoxy group of 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom include a fluorine atom, chlorine atom, bromine atom and iodine atom, and a fluorine atom is preferable.

Examples of the halogenated alkyl group include groups in which some or all of the hydrogen atoms within an alkyl group of 1 to 5 carbon atoms (such as a methyl group, ethyl group, propyl group, n-butyl group or tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably contains 1 to 20 carbon atoms, more preferably 1 to 15 carbon atoms, and most preferably 1 to 10 carbon atoms. Specific examples include a methyl group, ethyl group, propyl group, butyl group, pentyl group, hexyl group, heptyl group, octyl group, nonyl group, decyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group or docosyl group.

The branched saturated hydrocarbon group (alkyl group) preferably contains 3 to 20 carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group or 4-methylpentyl group.

The unsaturated hydrocarbon group preferably contains 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (allyl group) and a butynyl group. Examples of branched monovalent unsaturated hydrocarbon groups include a 1-methylpropenyl group and a 2-methylpropenyl group.

Among the above examples, a propenyl group is particularly desirable as the unsaturated hydrocarbon group.

The aliphatic cyclic group may be either a monocyclic group or a polycyclic group. The aliphatic cyclic group preferably contains 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples of the aliphatic cyclic group include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent in the ring structure, the aliphatic cyclic group is preferably a polycyclic group, more preferably a group in which one or more hydrogen atoms have been removed from a polycycloalkane, and most preferably a group in which one or more hydrogen atoms have been removed from adamantane.

When the aliphatic cyclic group contains a hetero atom-containing substituent in the ring structure, the hetero atom-containing substituent is preferably —O—, —C(=O)—O—, —S—, —S(=O)$_2$— or —S(=O)$_2$—O—. Specific examples of such aliphatic cyclic groups include the groups represented by formulas (L1) to (L7) and (S1) to (S4) shown below.

[Chemical Formula 45]

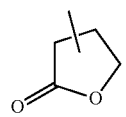
(L1)

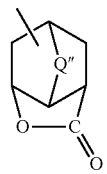
(L2)

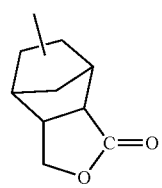
(L3)

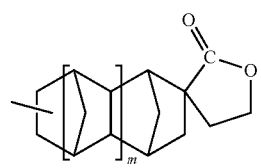
(L4)

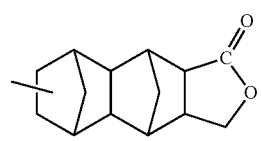
(L5)

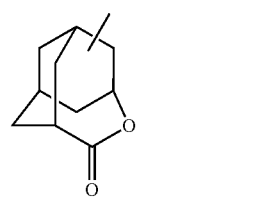
(L6)

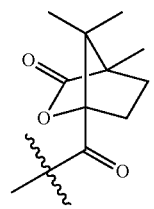
(L7)

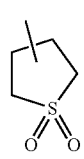
(S1)

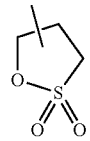
(S2)

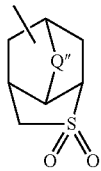
(S3)

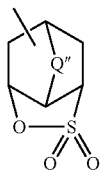
(S4)

In the formulas, Q" represents an alkylene group of 1 to 5 carbon atoms, —O—, —S—, —O—$R^{94'}$— or —S—$R^{95'}$— (wherein each of $R^{94'}$ and $R^{95'}$ independently represents an alkylene group of 1 to 5 carbon atoms), and m represents 0 or 1.

Examples of the alkylene groups for Q", $R^{94'}$ and $R^{95'}$ include the same alkylene groups as those described above for $R^{91}$ to $R^{93}$.

In these aliphatic cyclic groups, some of the hydrogen atoms bonded to the carbon atoms that constitute the ring structure may be substituted with a substituent. Examples of this substituent include an alkyl group, alkoxy group, halogen atom, halogenated alkyl group, hydroxyl group or oxygen atom (=O).

As the alkyl group, an alkyl group of 1 to 5 carbon atoms is preferable, and a methyl group, ethyl group, propyl group, n-butyl group or tert-butyl group is particularly desirable.

Examples of the alkoxy group and the halogen atom include the same groups and atoms as those listed above for the substituent used for substituting some or all of the hydrogen atoms.

In the present invention, $X^3$ is preferably a cyclic group which may have a substituent. This cyclic group may be either an aromatic hydrocarbon group which may have a substituent, or an aliphatic cyclic group which may have a substituent, although an aliphatic cyclic group which may have a substituent is preferable.

As the aromatic hydrocarbon group, a naphthyl group which may have a substituent or a phenyl group which may have a substituent is preferable.

As the aliphatic cyclic group which may have a substituent, a polycyclic aliphatic cyclic group which may have a substituent is preferable. As this polycyclic aliphatic cyclic group, groups in which one or more hydrogen atoms have been removed from an aforementioned polycycloalkane, and groups represented by the above formulas (L2) to (L7), and (S3) and (S4) are preferable.

Among the above possibilities, $R^{20}$ is preferably a halogenated alkyl group or a group having $X^3$-$Q^1$- as a substituent.

In those cases where $R^{20}$ has $X^3$-$Q^1$- as a substituent, $R^{20}$ is preferably a group represented by the formula $X^3$-$Q^1$-$Y^3$— (wherein $Q^1$ and $X^3$ are the same as defined above, and $Y^3$ represents an alkylene group of 1 to 4 carbon atoms which may have a substituent, or a fluorinated alkylene group of 1 to 4 carbon atoms which may have a substituent).

In the group represented by the formula $X^3$-$Q^1$-$Y^3$—, examples of the alkylene group represented by $Y^3$ include those alkylene groups described above for $Q^1$ in which the number of carbon atoms is within a range from 1 to 4.

Examples of the fluorinated alkylene group for $Y^3$ include groups in which some or all of the hydrogen atoms of an aforementioned alkylene group have been substituted with fluorine atoms.

Specific examples of $Y^3$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—, —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—, —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$— and —$C(CH_3)(CH_2CH_3)$—.

$Y^3$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CH_2CF_2$—, —$CH_2CH_2CF_2$—, —$CH_2CF_2CF_2$—, —$CH_2CH_2CH_2CF_2$—, —$CH_2CH_2CF_2CF_2$— and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The expression that the alkylene group or fluorinated alkylene group "may have a substituent" means that some or all of the hydrogen atoms or fluorine atoms in the alkylene group or fluorinated alkylene group may be substituted, either with atoms other than hydrogen atoms and fluorine atoms, or with groups.

Examples of substituents which the alkylene group or fluorinated alkylene group may have include alkyl groups of 1 to 4 carbon atoms, alkoxy groups of 1 to 4 carbon atoms, and a hydroxyl group.

Specific examples of $R^{20}$—$SO_3^-$ in those cases where $R^{20}$ is a group represented by $X^3$-$Q^1$-$Y^3$— include anions represented by formulas (b1) to (b12) shown below.

[Chemical Formula 46]

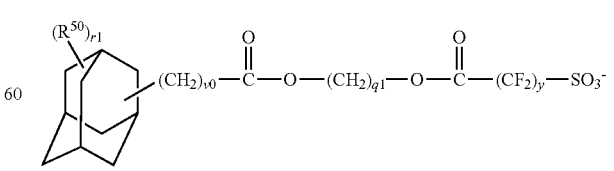
(b1)

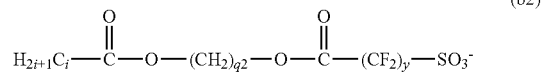
(b2)

-continued (b3)
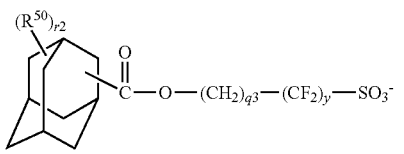

(b4)
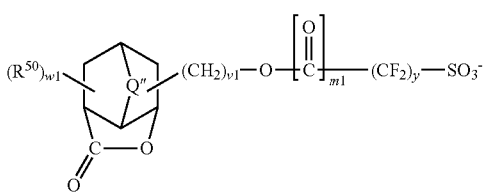

(b5)
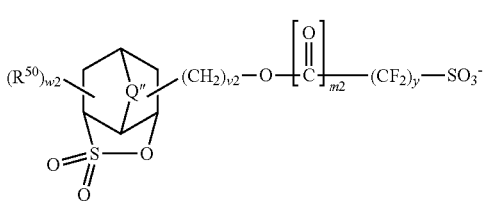

(b6)
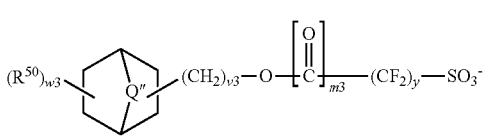

[Chemical Formula 47]

(b7)
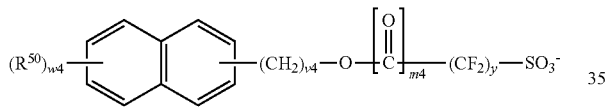

(b8)
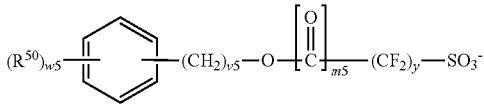

(b9)
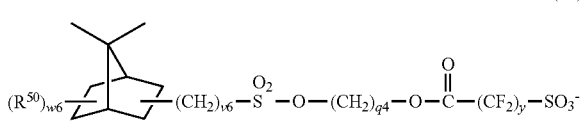

(b10)
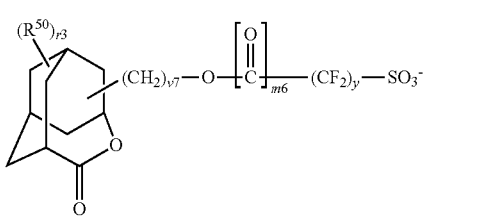

(b11)
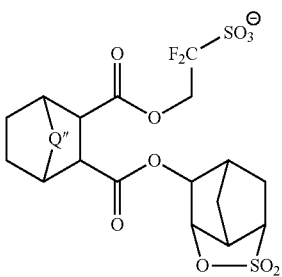

-continued (b12)
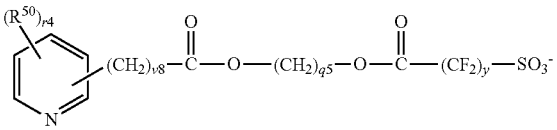

In the formulas, y represents an integer of 1 to 3, each of q1, q2 and q5 independently represents an integer of 1 to 5, q3 represents an integer of 1 to 12, q4 represents an integer of 1 to 3, each of r1 to r4 independently represents an integer of 0 to 3, i represents an integer of 1 to 20, $R^{50}$ represents a substituent, each of m1 to m6 independently represents 0 or 1, each of v0 to v8 independently represents an integer of 0 to 3, each of w1 to w6 independently represents an integer of 0 to 3, and Q" is the same as defined above.

Examples of the substituent for $R^{50}$ include the same groups as those which the aforementioned aliphatic hydrocarbon group or aromatic hydrocarbon group for $X^3$ may have as a substituent.

If there are two or more $R^{50}$ groups, as indicated by the values r1 to r4 and w1 to w6, then the plurality of $R^{50}$ groups within the compound may be the same or different from each other.

Further, in the above general formula (b1-2), $X^-$ may also be an anion represented by general formula (b-3) shown below, or an anion represented by general formula (b-4) shown below.

[Chemical Formula 48]

(b-3)
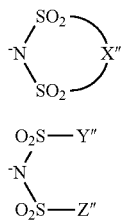

(b-4)
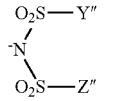

In the formulas, X" represents an alkylene group of 2 to 6 carbon atoms in which at least one hydrogen atom has been substituted with a fluorine atom, and each of Y" and Z" independently represents an alkyl group of 1 to 10 carbon atoms in which at least one hydrogen atom has been substituted with a fluorine atom.

In general formula (b-3), X" represents a linear or branched alkylene group in which at least one hydrogen atom has been substituted with a fluorine atom, wherein the alkylene group preferably contains 2 to 6 carbon atoms, more preferably 3 to 5 carbon atoms, and most preferably 3 carbon atoms.

In general formula (b-4), each of Y" and Z" independently represents a linear or branched alkyl group in which at least one hydrogen atom has been substituted with a fluorine atom, wherein the alkyl group preferably contains 1 to 10 carbon atoms, more preferably 1 to 7 carbon atoms, and most preferably 1 to 3 carbon atoms.

The smaller the number of carbon atoms of the alkylene group for X" or the alkyl group for Y" and Z" within the above-mentioned ranges of the number of carbon atoms, the more the solubility in a resist solvent is improved, and therefore a smaller number of carbon atoms is preferred.

Further, in the alkylene group for X″ or the alkyl group for Y″ and Z″, it is preferable that the number of hydrogen atoms substituted with fluorine atoms is as large as possible, because the acid strength increases and the transparency to high energy radiation of 200 nm or less and electron beams is improved.

The fluorination ratio of the alkylene group or alkyl group is preferably within a range from 70 to 100%, and more preferably from 90 to 100%. A perfluoroalkylene or perfluoroalkyl group in which all the hydrogen atoms are substituted with fluorine atoms is the most desirable.

Additional examples of X⁻ in the above general formula (b1-2) include anions represented by general formulas (b-5) to (b-7) shown below.

[Chemical Formula 49]

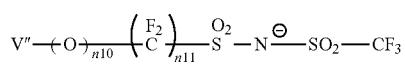 (b-5)

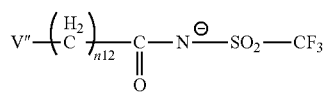 (b-6)

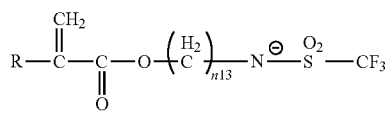 (b-7)

In the formulas, V″ represents an aliphatic cyclic group, R is the same as defined above for R in formula (a1-0-1), and each of n11 to n13 independently represents an integer of 0 to 3.

Examples of the aliphatic cyclic group for V″ include the same groups as those described above for the aliphatic cyclic group for $X^3$, and a group in which one hydrogen atom has been removed from cyclohexane or adamantane is preferred.

R is preferably a methyl group.

Furthermore, in the above general formula (b1-2), X⁻ may also be represented by $R^a$—COO⁻ [wherein $R^a$ represents an alkyl group or a fluorinated alkyl group].

Specific examples of the group $R^a$ in the above formula include the same groups as those listed above for $R^{20″}$.

Specific examples of $R^a$—COO⁻ include a trifluoroacetate ion, an acetate ion, and a 1-adamantanecarboxylate ion.

Additional examples of X⁻ within the general formula (b1-2) include anions represented by general formulas (b-8) and (b-9) shown below.

[Chemical Formula 50]

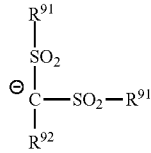 (b-8)

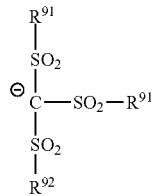 (b-9)

In the formulas, $R^{91}$ represents an alkyl group or a fluorinated alkyl group of 1 to 10 carbon atoms, and $R^{92}$ represents a hydrocarbon which may have a substituent, provided that at least one of $R^{91}$ and $R^{92}$ within each formula contains a fluorine atom.

The alkyl group for $R^{91}$ is preferably a linear or branched alkyl group, and is most preferably a linear alkyl group. The alkyl group contains 1 to 10 carbon atoms, preferably 1 to 5 carbon atoms, and more preferably 1 to 3 carbon atoms. The fluorinated alkyl group for $R^{91}$ is an aforementioned alkyl group in which at least one hydrogen atom has been substituted with a fluorine atom, and is preferably a perfluoroalkyl group.

$R^{92}$ represents a hydrocarbon group which may have a substituent, and examples include the same hydrocarbon groups as those described above for $X^3$. Among these, functional groups that are sterically more bulky are better able to control diffusion of the acid, and therefore $R^{92}$ is preferably an aliphatic cyclic group or aromatic hydrocarbon group which may have a substituent, and is more preferably an aromatic hydrocarbon group which may have a substituent. Further, some or all of the hydrogen atoms of the aromatic hydrocarbon group are preferably substituted with fluorine atoms, and the aromatic hydrocarbon group is most preferably a perfluoroaryl group.

Examples of the substituents include the same substituents as those described above in connection with $X^3$.

Furthermore, in general formula (b1-2), X⁻ may also represent a halogen anion.

Examples of this halogen anion include a fluoride ion, chloride ion, bromide ion or iodide ion.

Of the various possibilities described above, X⁻ within general formula (b1-2) is preferably an anion represented by general formula $R^{20}SO_3^-$ (and in particular, an anion represented by one of the above formulas (b1) to (b12) in which $R^{20}$ is a group represented by $X^3$-$Q^1$-$Y^3$—), or an anion represented by one of the above formulas (b-3) to (b-9).

A single component (B1) may be used alone, or two or more different types of the component (B1) may be used in combination. Using two or more different types of the component (B1) in combination yields better improvement in the MEEF, and is therefore preferred. Further, in those cases where two or more types of the component (B1) are combined, one type is preferably a component (hereinafter referred to as "component (B11)") containing an anion moiety selected from among (b1) to (b11), and another type is preferably a component (hereinafter referred to as "component (B12)") containing a d-camphor-10-sulfonate ion, an anion represented by formula (b12) or (b-7), or a 1-adamantanecarboxylate ion as the anion moiety.

In the resist composition of the present invention, the amount of the component (B1) within the component (B) is preferably not less than 40% by weight, is more preferably 60% by weight or more, and may be 100% by weight.

[Component (B2)]

In the resist composition of the present invention, if required, the component (B) may also include, in addition to the component (B1) described above, another acid generator (hereinafter referred to as "component (B2)") that does not correspond with the definition of the component (B1) described above.

As the component (B2), there are no particular limitations provided the acid generator falls outside the definition for the component (B1), and any of the known acid generators used in conventional chemically amplified resist compositions can be used. Examples of these acid generators are numerous, and include onium salt acid generators such as iodonium salts and sulfonium salts, oxime sulfonate acid generators, diazomethane acid generators such as bisalkyl or bisaryl sulfonyl diazomethanes and poly(bis-sulfonyl)diazomethanes, nitrobenzylsulfonate acid generators, iminosulfonate acid generators, and disulfone acid generators.

As an onium salt acid generator, compounds represented by general formulas (b-1) and (b-2) shown below may be used.

[Chemical Formula 51]

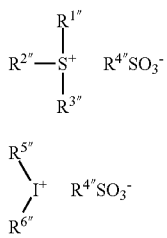

In the formulas, each of $R^{1''}$ to $R^{3''}$, $R^{5''}$ and $R^{6''}$ independently represents an aryl group or alkyl group, wherein two of $R^{1''}$ to $R^{3''}$ in formula (b-1) may be bonded to each other to form a ring together with the sulfur atom in the formula, and $R^{4''}$ represents a linear, branched or cyclic alkyl group, a halogenated alkyl group, an aryl group or an alkenyl group which may have a substituent, with the provision that at least one of $R^{1''}$ to $R^{3''}$ represents an aryl group, and at least one of $R^{5''}$ and $R^{6''}$ represents an aryl group.

In formula (b-1), each of $R^{1''}$ to $R^{3''}$ independently represents an aryl group or an alkyl group. In formula (b-1), two of $R^{1''}$ to $R^{3''}$ may be bonded to each other to form a ring together with the sulfur atom in the formula.

Further, among $R^{1''}$ to $R^{3''}$, at least one group represents an aryl group. Among $R^{1''}$ to $R^{3''}$, two or more groups are preferably aryl groups, and it is particularly desirable that all of $R^{1''}$ to $R^{3''}$ are aryl groups.

Examples of the aryl groups and alkyl groups for $R^{1''}$ to $R^{3''}$ include the same aryl groups and alkyl groups as those described above for $R^2$ and $R^3$ in formula (b1-2).

When two of $R^{1''}$ to $R^{3''}$ in formula (b-1) are bonded to each other to form a ring together with the sulfur atom in the formula, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom.

When two of $R^{1''}$ to $R^{3''}$ in formula (b-1) are bonded to each other to form a ring together with the sulfur atom in the formula, the remaining one of $R^{1''}$ to $R^{3''}$ is preferably an aryl group. Examples of this aryl group include the same aryl groups as those described above for $R^{1''}$ to $R^{3''}$.

Examples of preferred cation moieties for the compound represented by general formula (b-1) include the cation moieties represented by formulas (I-1-1) to (I-1-10) shown below. Among these, a cation moiety having a triphenylmethane skeleton, such as a cation moiety represented by any one of formulas (I-1-1) to (I-1-8) shown below, is particularly desirable.

In formulas (I-1-9) and (I-1-10) below, each of $R^9$ and $R^{10}$ independently represents a phenyl group or naphthyl group which may have a substituent, an alkyl group of 1 to 5 carbon atoms, an alkoxy group of 1 to 5 carbon atoms, or a hydroxyl group.

u is an integer of 1 to 3, and most preferably 1 or 2.

[Chemical Formula 52]

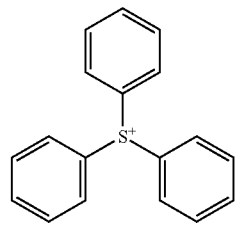
(I-1-1)

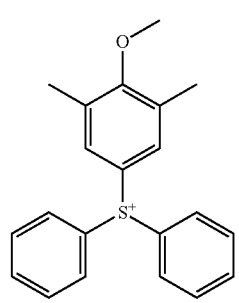
(I-1-2)

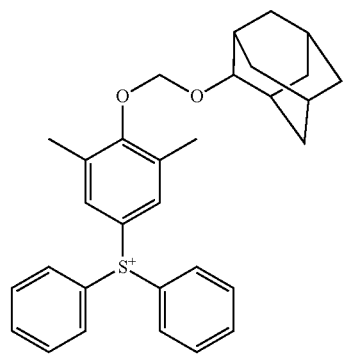
(I-1-3)

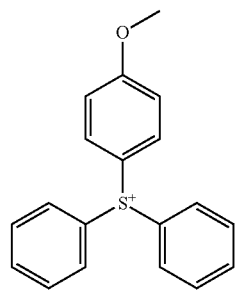
(I-1-4)

-continued

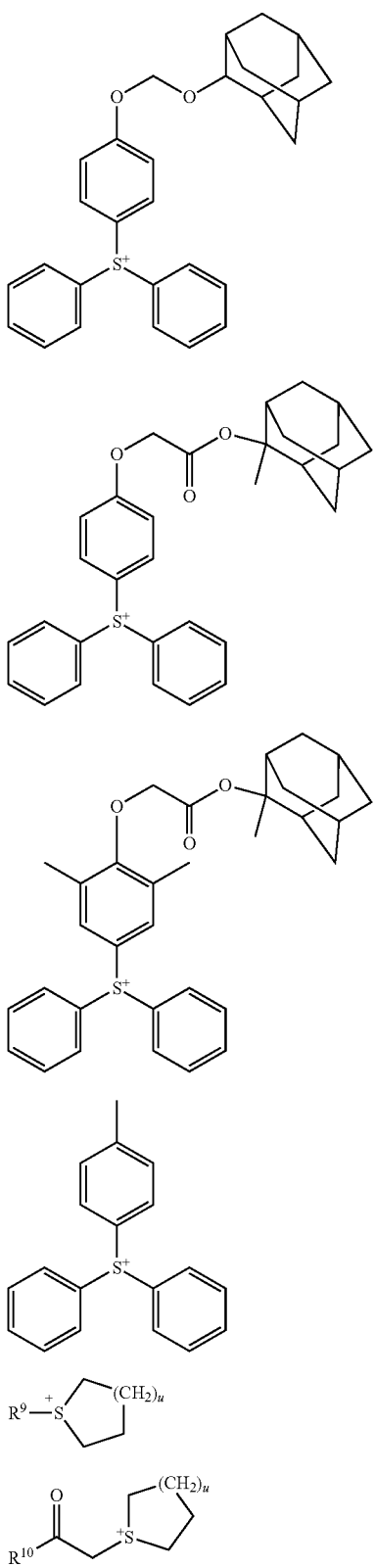

(I-1-5)

(I-1-6)

(I-1-7)

(I-1-8)

(I-1-9)

(I-1-10)

$R^{4\prime\prime\prime}$ represents a linear, branched or cyclic alkyl group, a halogenated alkyl group, an aryl group or an alkenyl group which may have a substituent, and is the same as defined above for $R^{20}$ in the formula $R^{20}SO_3^-$.

In formula (b-2), each of $R^{5\prime\prime\prime}$ and $R^{6\prime\prime\prime}$ independently represents an aryl group or an alkyl group. At least one of $R^{5\prime\prime\prime}$ and $R^{6\prime\prime\prime}$ represents an aryl group. It is preferable that $R^{5\prime\prime\prime}$ and $R^{6\prime\prime\prime}$ both represent aryl groups.

Examples of the aryl groups and alkyl groups for $R^{5\prime\prime\prime}$ and $R^{6\prime\prime\prime}$ include the same aryl groups and alkyl groups as those described above for $R^2$ and $R^3$ in formula (b1-2).

It is particularly desirable that $R^{5\prime\prime\prime}$ and $R^{6\prime\prime\prime}$ both represent phenyl groups.

Examples of $R^{4\prime\prime\prime}$ in formula (b-2) include the same groups as those mentioned above for $R^{4\prime\prime\prime}$ in formula (b-1).

Specific examples of the onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts has been replaced by an alkylsulfonate such as methanesulfonate, n-propanesulfonate, n-butanesulfonate, n-octanesulfonate, 1-adamantanesulfonate, 2-norbornanesulfonate, d-camphor-10-sulfonate, benzenesulfonate, perfluorobenzenesulfonate or p-toluenesulfonate.

Further, onium salts in which the anion moiety of these onium salts has been replaced by an anion moiety represented by any one of formulas (b1) to (b12) shown above, and formulas (b-3) to (b-9) shown above, can also be used.

Furthermore, sulfonium salts having a cation moiety represented by general formula (b-15) or (b-16) shown below may also be used as the onium salt acid generator.

[Chemical Formula 53]

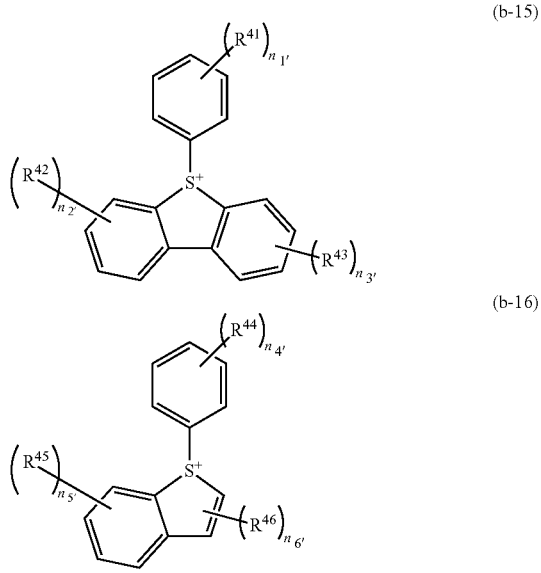

(b-15)

(b-16)

In the formulas, $R^{41}$ to $R^{46}$ are the same as defined above for $R^{31}$ to $R^{39}$, each of $n_1'$ to $n_5'$ represents an integer of 0 to 3, and $n_6'$ represents an integer of 0 to 2.

If there are two or more of an individual $R^{41}$ to $R^{46}$ group, as indicated by the corresponding value of $n_1'$ to $n_6'$, then the two or more of the individual $R^{41}$ to $R^{46}$ group may be the same or different from each other.

$n_1'$ is preferably 0 to 2, more preferably 0 or 1, and still more preferably 0.

It is preferable that each of $n_2'$ and $n_3'$ independently represents 0 or 1, and more preferably 0.

$n_4'$ is preferably 0 to 2, and more preferably 0 or 1.

$n_5'$ is preferably 0 or 1, and more preferably 0.

$n_6'$ is preferably 0 or 1, and more preferably 1.

There are no particular limitations on the anion moiety of the sulfonium salt having a cation moiety represented by formula (b-15) or (b-16), and the same anion moieties that have already been proposed for onium salt acid generators may be used. Examples of such anion moieties include fluorinated alkylsulfonate ions such as the anion moieties ($R^{4"'}SO_3^-$) for the onium salt acid generators represented by general formula (b-1) or (b-2) shown above, and anion moieties represented by formulas (b-3) to (b-9) shown above.

In the present description, an oxime sulfonate acid generator is a compound having at least one group represented by general formula (B-1) shown below, and has a feature of generating acid by irradiation. Such oxime sulfonate acid generators are widely used for chemically amplified resist compositions, and any of these known compounds may be selected as appropriate.

[Chemical Formula 54]

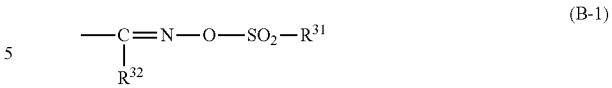

(B-1)

In the formula (B-1), each of $R^{31}$ and $R^{32}$ independently represents an organic group.

The organic group for $R^{31}$ and $R^{32}$ refers to a group containing a carbon atom, and may include atoms other than carbon atoms (such as a hydrogen atom, oxygen atom, nitrogen atom, sulfur atom or halogen atom (such as a fluorine atom or chlorine atom) or the like).

As the organic group for $R^{31}$, a linear, branched, or cyclic alkyl group or aryl group is preferable. The alkyl group or aryl group may have a substituent. There are no particular limitations on the substituent, and examples thereof include a fluorine atom and a linear, branched or cyclic alkyl group of 1 to 6 carbon atoms. The expression that the alkyl group or aryl group "may have a substituent" means that some or all of the hydrogen atoms of the alkyl group or aryl group may be substituted with substituents.

The alkyl group preferably contains 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably contains 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of the hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched or cyclic alkyl group, an aryl group, or a cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent, or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 55]

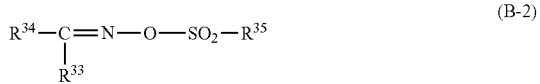

(B-2)

In formula (B-2), $R^{33}$ represents a cyano group, an alkyl group having no substituent or a halogenated alkyl group, $R^{34}$ represents an aryl group, and $R^{35}$ represents an alkyl group having no substituent or a halogenated alkyl group.

[Chemical Formula 56]

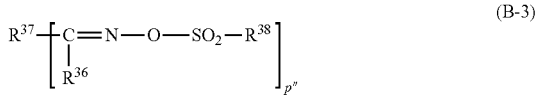
(B-3)

In formula (B-3), $R^{36}$ represents a cyano group, an alkyl group having no substituent or a halogenated alkyl group, $R^{37}$ represents a divalent or trivalent aromatic hydrocarbon group, $R^{38}$ represents an alkyl group having no substituent or a halogenated alkyl group, and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more fluorinated, and most preferably 90% or more fluorinated.

Examples of the aryl group for $R^{34}$ include groups in which one hydrogen atom has been removed from an aromatic hydrocarbon ring, such as a phenyl group, biphenylyl group, fluorenyl group, naphthyl group, anthryl group or phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group or halogenated alkyl group as the substituent preferably contains 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably contains 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more fluorinated, and still more preferably 90% or more fluorinated. A completely fluorinated alkyl group in which 100% of the hydrogen atoms have been substituted with fluorine atoms is particularly desirable.

In general formula (B-3), examples of the alkyl group having no substituent and the halogenated alkyl group for $R^{36}$ include the same groups as those described above for the alkyl group having no substituent and the halogenated alkyl group for $R^{33}$.

Examples of the divalent or trivalent aromatic hydrocarbon group for $R^{37}$ include groups in which an additional one or two hydrogen atoms have been removed from the aryl group for $R^{34}$.

Examples of the alkyl group having no substituent or the halogenated alkyl group for $R^{38}$ include the same groups as those described above for the alkyl group having no substituent or the halogenated alkyl group for $R^{35}$.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in JP-09-208554-A (Chemical Formulas 18 and 19 shown in paragraphs [0012] to [0014]) and oxime sulfonate-based acid generators disclosed in WO 04/074242 pamphlet (Examples 1 to 40 described on pages 65 to 86) may also be used favorably.

Furthermore, the following compounds may also be used as preferred examples.

[Chemical Formula 57]

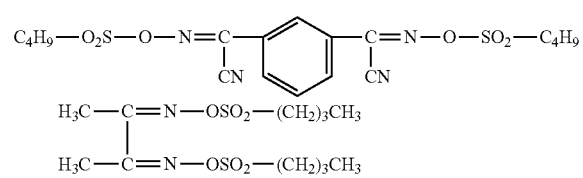

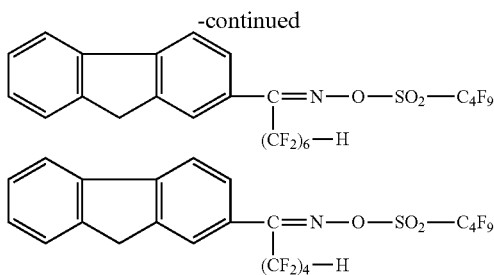

Of the above-mentioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in JP-11-035551-A, JP-11-035552-A and JP-11-035573-A may also be used favorably.

Furthermore, examples of poly(bis-sulfonyl)diazomethanes include those disclosed in JP-11-322707-A, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B2), one type of acid generator described above may be used alone, or two or more types of acid generators may be used in combination.

In the present invention, a single type of component (B) may be used alone, or two or more types may be used in combination. Using two or more different types of the component (B) in combination yields better improvement in the MEEF, and is therefore preferred. Further, in those cases where two or more types of the component (B) are combined, either two or more types of the component (B1) may be combined (the former case), or two or more components selected from the component (B1) and the component (B2) may be combined (the latter case).

In the former case, one type of the component (B1) is preferably a component (hereinafter referred to as "component (B11)") containing an anion moiety selected from among (b1) to (b11), and another type is preferably a component (hereinafter referred to as "component (B12)") containing a d-camphor-10-sulfonate ion, an anion represented by formula (b12) or (b-7), or a 1-adamantanecarboxylate ion as the anion moiety. The anion of the component (B12) is most preferably a d-camphor-10-sulfonate ion, as such components offer superior improvement in the LWR and the EL margin.

The weight ratio between the component (B11) and the component (B12) is preferably within a range from 99:1 to 50:50, more preferably from 95:5 to 60:40, and still more preferably from 90:10 to 65:35.

In the latter case, the component (B1) is preferably a component containing an anion moiety selected from among (b1) to (b11) (namely, the component (B11), and the component (B2) is preferably a component (hereinafter referred to as "component (B22)") containing a d-camphor-10-sulfonate ion, an anion represented by formula (b12) or (b-7), or a 1-adamantanecarboxylate ion as the anion moiety.

The weight ratio between the component (B11) and the component (B22) is preferably within a range from 99:1 to 50:50, more preferably from 95:5 to 60:40, and still more preferably from 90:10 to 65:35.

The total amount of the overall component (B) within the resist composition of the present invention is preferably within a range from 1 to 70 parts by weight, more preferably from 3 to 60 parts by weight, and still more preferably from 5 to 50 parts by weight, relative to 100 parts by weight of the component (A). When the amount of the component (B) is within the above-mentioned range, formation of a resist pattern can be performed satisfactorily. Further, a uniform solution can be obtained and the storage stability tends to improve.

<Optional Components>

[Component (D)]

The resist composition of the present invention preferably further includes a nitrogen-containing organic compound (D) (hereafter referred to as "component (D)") as an optional component There are no particular limitations on the component (D) provided it functions as an acid diffusion control agent, namely, a quencher which traps the acid generated from the component (B) upon exposure. A multitude of these components (D) have already been proposed, and any of these known compounds may be used. Among these conventional compounds, an aliphatic amine, and particularly a secondary aliphatic amine or tertiary aliphatic amine is preferable.

An "aliphatic amine" is an amine having one or more aliphatic groups, and each of the aliphatic groups preferably contains 1 to 12 carbon atoms.

Examples of these aliphatic amines include amines in which at least one hydrogen atom of ammonia ($NH_3$) has been substituted with an alkyl group or hydroxyalkyl group of not more than 12 carbon atoms (namely, alkylamines or alkyl alcohol amines), and cyclic amines.

Specific examples of the alkylamines and alkyl alcohol amines include monoalkylamines such as n-hexylamine, n-heptylamine, n-octylamine, n-nonylamine and n-decylamine, dialkylamines such as diethylamine, di-n-propylamine, di-n-heptylamine, di-n-octylamine and dicyclohexylamine, trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decanylamine and tri-n-dodecylamine, and alkyl alcohol amines such as diethanolamine, triethanolamine, diisopropanolamine, triisopropanolamine, di-n-octanolamine and tri-n-octanolamine. Among these, trialkylamines of 5 to 10 carbon atoms are preferred, and tri-n-pentylamine or tri-n-octylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)

ethyl}amine, tris[2-{2-(2-hydroxyethoxy)ethoxy}ethyl]amine and triethanolamine triacetate, and of these, triethanolamine triacetate is preferred.

Further, an aromatic amine may also be used as the component (D).

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonyl pyrrolidine.

As the component (D), a single compound may be used alone, or two or more different compounds may be used in combination.

The component (D) is typically used in an amount within a range from 0.01 to 5.0 parts by weight, relative to 100 parts by weight of the component (A). By ensuring that the amount of the component (D) is within the above-mentioned range, the shape of the resist pattern and the post exposure stability of the latent image formed by the pattern-wise exposure of the resist layer are improved.

[Component (E)]

In the resist composition of the present invention, for the purposes of preventing any deterioration in sensitivity, and improving the resist pattern shape and the post exposure stability of the latent image formed by the pattern-wise exposure of the resist layer, at least one compound (E) (hereinafter referred to as "component (E)") selected from the group consisting of organic carboxylic acids, and phosphorus oxo acids and derivatives thereof may be added as an optional component.

Examples of the organic carboxylic acids include acetic acid, malonic acid, citric acid, malic acid, succinic acid, benzoic acid and salicylic acid.

Examples of the phosphorus oxo acids include phosphoric acid, phosphonic acid and phosphinic acid. Among these, phosphonic acid is particularly desirable.

Examples of the phosphorus oxo acid derivatives include esters in which a hydrogen atom within an aforementioned oxo acid is substituted with a hydrocarbon group. Examples of the hydrocarbon group include alkyl groups of 1 to 5 carbon atoms and aryl groups of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one compound may be used alone, or two or more different compounds may be used in combination.

The component (E) is preferably an organic carboxylic acid, and is most preferably salicylic acid.

The component (E) is typically used in an amount within a range from 0.01 to 5.0 parts by weight relative to 100 parts by weight of the component (A).

If desired, other miscible additives besides those described above may also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the components that constitute the resist composition in an organic solvent (S) (hereinafter, frequently referred to as "component (S)").

The component (S) may be any organic solvent which can dissolve the respective components to give a uniform solution, and one or more types of organic solvent may be selected appropriately from those solvents which have been conventionally known as solvents for chemically amplified resists.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; polyhydric alcohol derivatives, including compounds having an ester bond such as ethylene glycol monoacetate, diethylene glycol monoacetate, propylene glycol monoacetate and dipropylene glycol monoacetate, and compounds having an ether bond such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene.

As the component (S), one the above organic solvents may be used alone, or two or more solvents may be used as a mixed solvent.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is also preferable. The mixing ratio (weight ratio) of this mixed solvent can be determined appropriately with due consideration of the compatibility of the PGMEA with the polar solvent, but is preferably in the range of 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME ratio is preferably from 1:9 to 9:1, more preferably from 2:8 to 8:2, and still more preferably from 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Moreover, a mixed solvent containing PGMEA, PGME and cyclohexanone is also preferred as the component (S). In this case, the mixing ratio of PGMEA:PGME:cyclohexanone is preferably within a range from (35 to 55):(25 to 45):(10 to 30).

The amount used of the component (S) is not particularly limited, and may be adjusted appropriately to a concentration which enables coating of a coating solution onto a substrate in accordance with the thickness of the coating film. In general, the organic solvent is used in an amount that yields a solid content for the resist composition that is within a range from 0.5 to 20% by weight, and preferably from 1 to 15% by weight.

Dissolution of the components that constitute the resist composition in the component (S) can be conducted by simply mixing and stirring each of the above components together using conventional methods. If necessary, the composition may also be mixed and dispersed using a dispersion device such as a dissolver, homogenizer or triple roll mill. Furthermore, following mixing, the composition may also be filtered using a mesh or membrane filter or the like.

As described above, the component (B1) used in the resist composition of the present invention is a novel compound that is not currently known.

By including the component (B1) within the component (B), the lithography properties of the resist composition of the present invention, such as the EL margin, MEEF and LWR, can be improved.

Although the reasons that the above effects are obtained are not entirely clear, it is thought that because the component (B1) includes a polar group represented by formula (b1-1) within the cation moiety, the component (B1) is able to disperse uniformly through the resist film. Further, it is also thought that because the group represented by formula (b1-1) has a bulky structure, diffusion of the acid generated from the uniformly dispersed component (B1) can be better controlled, resulting in an improvement in the lithography properties of the formed resist pattern.

<<Method of Forming Resist Pattern>>

The method of forming a resist pattern according to the second aspect of the present invention includes: forming a resist film on a substrate using the resist composition of the first aspect described above, conducting exposure of the resist film, and developing the resist film to form a resist pattern.

The method of forming a resist pattern according to the present invention can be performed, for example, as follows.

Firstly, the resist composition described above is applied onto a substrate using a spinner or the like, and a prebake (post applied bake (PAB)) is conducted under temperature conditions of 80 to 150° C. for 40 to 120 seconds, and preferably 60 to 90 seconds, to form a resist film. Subsequently, for example, using an electron beam lithography apparatus or the like, the resist film is subjected to selective exposure with an electron beam (EB) through a desired mask pattern, and PEB (post exposure baking) is then conducted under temperature conditions of 80 to 150° C. for 40 to 120 seconds, and preferably 60 to 90 seconds. The resist film is then subjected to a developing treatment.

In the case of an alkali developing process, an alkali developing treatment is performed using an alkali developing solution such as a 0.1 to 10% by weight aqueous solution of tetramethylammonium hydroxide (TMAH).

Further, in the case of a solvent developing process, the developing treatment is performed using an organic solvent. As this organic solvent, any solvent that is capable of dissolving the component (A) (namely, the component (A) prior to exposure) may be used, and the solvent may be selected appropriately from conventional organic solvents. Examples of the organic solvent include polar solvents such as ketone solvents, ester solvents, alcohol solvents, amide solvents and ether solvents, as well as hydrocarbon solvents. Among these, ester solvents are preferable. Butyl acetate is particularly preferred as the ester solvent.

Following the developing treatment, a rinse treatment is preferably performed. In the case of an alkali developing process, a water rinse using pure water is preferable. In the case of a solvent developing process, the use of a rinse solution containing the types of organic solvents listed above is preferred.

Subsequently, drying is performed. If required, a bake treatment (post bake) may be conducted following the developing treatment. In this manner, a resist pattern that is faithful to the mask pattern can be obtained.

There are no particular limitations on the substrate, and a conventionally known substrate may be used. For example, substrates for electronic components, and such substrates having wiring patterns formed thereon can be used. Specific examples of the material of the substrate include metals such as silicon wafer, copper, chromium, iron and aluminum, as well as and glass. Suitable materials for the wiring pattern include copper, aluminum, nickel, and gold.

Further, as the substrate, any one of the above-mentioned substrates that has been provided with at least one film selected from the group consisting of inorganic films and organic films on the surface thereof may also be used. As the inorganic film, an inorganic antireflection film (inorganic BARC) can be used. As the organic film, an organic antireflection film (organic BARC) can be used.

The wavelength to be used for exposure is not particularly limited, and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is more effective for use with a KrF excimer laser, ArF excimer laser, EB or EUV, and is particularly effective for an ArF excimer laser.

The exposure of the resist film may employ either a general exposure method (dry exposure) conducted in air or an inert gas such as nitrogen, or a liquid immersion lithography method.

In liquid immersion lithography, exposure is conducted in a state where the region between the lens and the resist film formed on the wafer, which is conventionally filled with air or an inert gas such as nitrogen, is filled with a solvent (an immersion medium) that has a larger refractive index than the refractive index of air.

More specifically, in liquid immersion lithography, the region between the resist film formed in the aforementioned manner and the lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point that is preferably within a range from 70 to 180° C., and more preferably from 80 to 160° C. A fluorine-based inert liquid having a boiling point within the above-mentioned range is advantageous in that the removal of the immersion medium after the exposure can be conducted by a simple method.

As the fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point: 102° C.), and one example of a suitable perfluoroalkylamine compound is perfluorotributylamine (boiling point: 174° C.).

As the immersion medium, water is preferable in terms of cost, safety, environmental issues and versatility.

<<Compound>>

The compound that represents the third aspect of the present invention is a compound represented by general formula (b1-2) shown below. The compound represented by general formula (b1-2) shown below is the same as the compound represented by formula (b1-2) described in connection with the component (B1) contained in the component (B) of the resist composition according to the first aspect of the present invention described above.

[Chemical Formula 58]

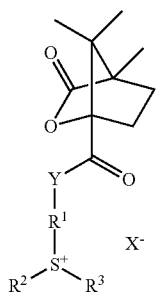

(b1-2)

In the formula, Y represents a divalent linking group, $R^1$ represents an arylene group which may have a substituent, each of $R^2$ and $R^3$ independently represents an organic group, $R^2$ and $R^3$ may be bonded to each other to form a ring with the sulfur atom in the formula, and $X^-$ represents a counter anion.

(Method of Producing the Compound)

There are no particular limitations on the method of producing the compound (b1-2), and for example in those cases where Y is a divalent linking group having —O— at the linking portion with the aforementioned formula (b1-1), the compound (b1-2) represented by general formula (b1-2) can be produced by reacting a compound (i-1) represented by general formula (i-1) shown below with a compound (i-2) represented by general formula (i-2) shown below to obtain a compound (i-3) represented by general formula (i-3), and subsequently reacting the compound (i-3) with a compound $X^-M^+$ (1-4) having a desired anion $X^-$.

[Chemical Formula 59]

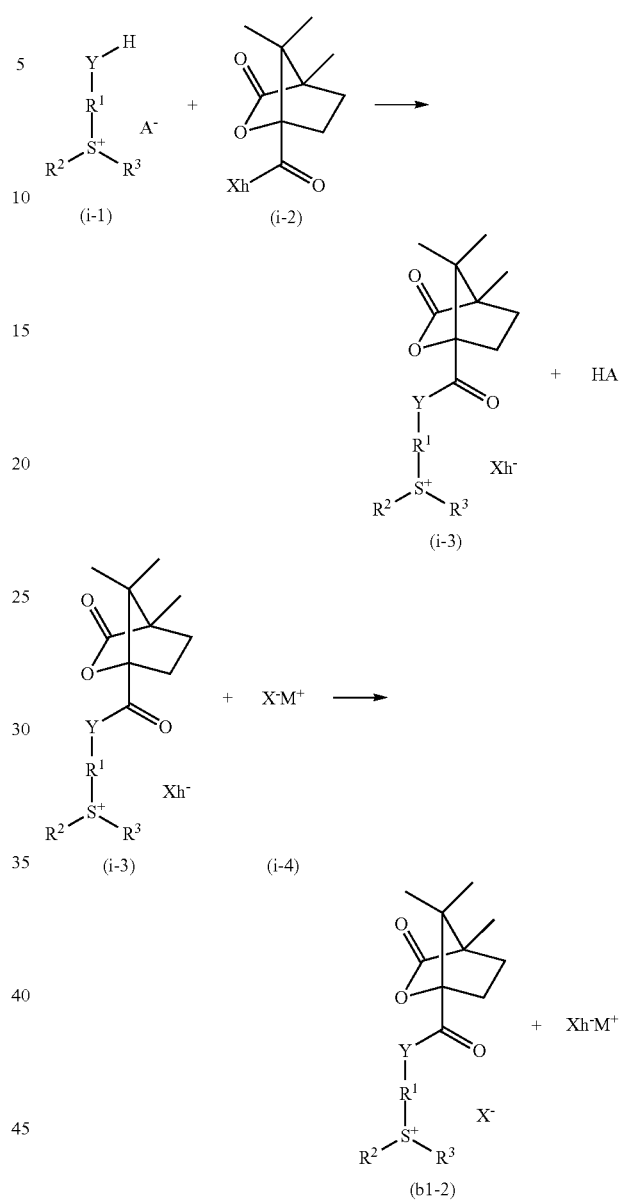

In the above formulas, $R^1$ to $R^3$, Y and $X^-$ are same as defined above for $R^1$ to $R^3$, Y and $X^-$ in general formula (b1-2), Xh represents a halogen atom, $A^-$ represents a counter anion, and $M^+$ represents an alkali metal ion or an ammonium ion which may have a substituent.

In the formula (i-1), $R^1$ to $R^3$ and Y are the same as defined above, $A^-$ represents a counter anion, and Xh represents a halogen atom, and is preferably a fluorine atom, chlorine atom, bromine atom or iodine atom.

There are no particular limitations on the method used for reacting the compound (i-1) and the compound (i-2), and in one sample method, the compound (i-1) is first dissolved in an appropriate organic solvent, and the resulting solution is stirred in the presence of an appropriate base. The compound (i-2) is then added and stirred, and following reaction, the reaction mixture is washed and the product is recovered.

As the compound (i-1) and the compound (i-2), commercially available compounds may be used, or the compounds may be synthesized.

In the aforementioned reaction, a chlorinated hydrocarbon solvent such as dichloromethane is preferably used as the organic solvent, and the amount of the solvent is preferably within a range from 0.5 to 100 parts by weight, and more preferably from 0.5 to 20 parts by weight, per 1 part by weight of the compound (i-1). As the solvent, a single organic solvent may be used alone, or two or more solvents may be used in combination.

Examples of the base include potassium carbonate, tertiary amines such as triethylamine, and aromatic amines such as pyridine, and any one of these bases may be used alone, or two or more bases may be used in combination. The amount used of the base need only be a catalytic amount, and is typically within a range from approximately 0.01 to 5 mols per 1 mol of the compound (i-1).

The reaction time for the above reaction varies depending on the reactivity between the compound (i-1) and the compound (i-2), and the reaction temperature and the like, but in most cases, is preferably within a range from 1 to 80 hours, and more preferably from 2 to 60 hours.

The reaction temperature of the above reaction is preferably within a range from 0° C. to 200° C., and more preferably from approximately 0° C. to 150° C.

The amount of the compound (i-2) used in the above reaction is preferably within a range from approximately 0.5 to 5 mols, and more preferably from 0.8 to 4 mols, per 1 mol of the compound (i-1).

In the above formula (i-4), $X^-$ is the same as defined above for $X^-$ in formula (b1-2), and $M^+$ represents an alkali metal ion or an ammonium ion which may have a substituent.

Examples of the alkali metal ion for $M^+$ include a sodium ion, lithium ion or potassium ion. Of these, a sodium ion or lithium ion is preferred.

Examples of the ammonium ion which may have a substituent for $M^+$ include cations represented by general formula (0-1) shown below.

[Chemical Formula 60]

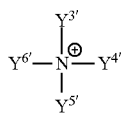

(0-1)

In the formula, each of $Y^{3'}$ to $Y^{6'}$ independently represents a hydrogen atom or a hydrocarbon group which may have a substituent, provided that at least one of $Y^{3'}$ to $Y^{6'}$ represents a hydrocarbon group which may have a substituent, and at least two of $Y^{3'}$ to $Y^{6'}$ may be bonded to each other to form a ring.

In formula (0-1), each of $Y^{3'}$ to $Y^{6'}$ independently represents a hydrogen atom or a hydrocarbon group which may have a substituent, provided that at least one of $Y^{3'}$ to $Y^{6'}$ represents a hydrocarbon group which may have a substituent.

Examples of the hydrocarbon group for $Y^{3'}$ to $Y^{6'}$ include the same hydrocarbon groups as those described above for $X^3$.

The hydrocarbon group may be either an aliphatic hydrocarbon group or an aromatic hydrocarbon group. When the hydrocarbon group is an aliphatic hydrocarbon group, the aliphatic hydrocarbon group is preferably an alkyl group of 1 to 12 carbon atoms which may have a substituent.

At least one of $Y^{3'}$ to $Y^{6'}$ represents a hydrocarbon group, and two or three of $Y^{3'}$ to $Y^{6'}$ are preferably hydrocarbon groups.

At least two of $Y^{3'}$ to $Y^{6'}$ may be bonded to each other to form a ring. For example, two of $Y^{3'}$ to $Y^{6'}$ may be bonded to each other to form a single ring, three of $Y^{3'}$ to $Y^{6'}$ may be bonded to each other to form a single cyclic structure, or two pairs of $Y^{3'}$ to $Y^{6'}$ may be respectively bonded to each other to form two separate rings.

The ring that is formed when at least two of $Y^{3'}$ to $Y^{6'}$ are bonded to each other to form a ring together with the nitrogen atom in the formula (namely, a heterocyclic ring including the nitrogen atom as a hetero atom) may be an aliphatic heterocyclic ring or an aromatic heterocyclic ring. Further, the heterocyclic ring may be either monocyclic or polycyclic.

Specific examples of the ammonium ion represented by formula (0-1) include ammonium ions derived from an amine.

In this description, an "ammonium ion derived from an amine" include cations formed by bonding a hydrogen atom to the nitrogen atom of an amine, and quaternary ammonium ions formed by bonding another substituent to the nitrogen atom of an amine.

The amine that gives rise to the above ammonium ion may be either an aliphatic amine or an aromatic amine.

Examples of the aliphatic amines include amines in which at least one hydrogen atom of ammonia ($NH_3$) has been substituted with an alkyl group or hydroxyalkyl group of not more than 12 carbon atoms (namely, alkylamines or alkyl alcohol amines), and cyclic amines.

Specific examples of the alkylamines and alkyl alcohol amines include monoalkylamines such as n-hexylamine, n-heptylamine, n-octylamine, n-nonylamine and n-decylamine, dialkylamines such as diethylamine, di-n-propylamine, di-n-heptylamine, di-n-octylamine and dicyclohexylamine, trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine, and alkyl alcohol amines such as diethanolamine, triethanolamine, diisopropanolamine, triisopropanolamine, di-n-octanolamine and tri-n-octanolamine.

Examples of the cyclic amines include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Examples of the aromatic amines include aniline, pyridine, 4-dimethylaminopyridine (DMAP), pyrrole, indole, pyrazole and imidazole.

Specific examples of the quaternary ammonium ion include a tetramethylammonium ion, tetraethylammonium ion and tetrabutylammonium ion.

As the ammonium ion represented by formula (0-1), ammonium ions in which at least one of $Y^{3'}$ to $Y^{6'}$ represents an alkyl group and at least one of $Y^{3'}$ to $Y^{6'}$ represents a hydrogen atom are preferable.

Among these, ammonium ions in which three of $Y^{3'}$ to $Y^{6'}$ represent alkyl groups and the remaining one of $Y^{3'}$ to $Y^{6'}$ represents a hydrogen atom (namely, trialkylammonium ions), and ammonium ions in which two of $Y^{3'}$ to $Y^{6'}$ represent alkyl groups and one of the remainder represents a hydrogen atom (namely, dialkylammonium ions) are particularly desirable.

Each of the alkyl groups within a trialkylammonium ion or dialkylammonium ion preferably independently represents an alkyl group of 1 to 10 carbon atoms, more preferably an alkyl group of 1 to 8 carbon atoms, and most preferably an alkyl group of 1 to 5 carbon atoms. Specific examples include a methyl group, ethyl group, propyl group, butyl group, pentyl group, hexyl group, heptyl group, octyl group, nonyl group and decanyl group. Among these, an ethyl group is the most preferred.

As the compound (1-4), a commercially available compound may be used, or the compound may be synthesized.

There are no particular limitations on the method used for reacting the compound (i-3) obtained using the method described above with the compound (i-4) to produce the compound (b1-2), and in one sample method, the compound (i-3) and the compound (i-4) are combined within an organic solvent and reacted under stirring, and the product is then recovered.

Examples of the organic solvent include dichloromethane, chloroform and ethyl acetate. The amount used of the organic solvent is preferably within a range from 0.5 to 100 parts by weight, and more preferably from 0.5 to 20 parts by weight, per 1 part by weight of the compound (i-3). As the solvent, a single organic solvent may be used alone, or two or more solvents may be used in combination.

The reaction time for the above reaction varies depending on the reactivity between the compound (i-3) and the compound (i-4), and the reaction temperature and the like, but in most cases, is preferably within a range from 0.5 to 50 hours, and more preferably from 1 to 20 hours.

The reaction temperature of the above reaction is preferably within a range from 20° C. to 200° C., and more preferably from approximately 20° C. to 150° C.

The amount of the compound (i-3) used in the above reaction is preferably within a range from approximately 0.5 to 5 mols, and more preferably from 0.8 to 4 mols, per 1 mol of the compound (i-4).

Following completion of the reaction, the compound (b1-2) within the reaction solution may be isolated and purified. Conventional methods may be used to isolate and purify the product, including concentration, solvent extraction, distillation, crystallization, recrystallization and chromatography, which may be used individually or in combinations of two or more different methods.

The structure of the compound of the present invention obtained in the manner described above can be confirmed by conventional organic analysis methods such as $^{1}$H nuclear magnetic resonance (NMR) spectroscopy, $^{13}$C-NMR spectroscopy, $^{19}$F-NMR spectroscopy, infrared (IR) absorption spectroscopy, mass spectrometry (MS), elemental analysis methods, and X-ray crystal diffraction methods.

The compound of the present invention described above is a novel compound that is useful as an acid generator for resist compositions, and can be added to a resist composition as an acid generator.

<<Acid Generator>>

The acid generator of the fourth aspect of the present invention is a compound represented by the above general formula (b1-2).

This acid generator is useful as an acid generator for a chemically amplified resist composition, such as the acid generator component (B) of the resist composition according to the first aspect of the present invention.

EXAMPLES

A more detailed description of the present invention is presented below based on a series of examples, although the present invention is in no way limited by these examples.

In the examples, for the NMR analyses, tetramethylsilane (TMS) was used as an internal standard for $^{1}$H-NMR, and hexafluorobenzene was used as an internal standard for $^{19}$F-NMR (with the hexafluorobenzene peak designated as –160 ppm).

Synthesis Example 1

Synthesis of PAG-B

PAG-A (20.1 g) and dichloromethane (140.9 g) were combined under a nitrogen atmosphere, and the resulting solution was cooled to 10° C. or lower using an ice bath. Triethylamine (TEA) (6.1 g) was added dropwise to the solution, and a solution prepared by dissolving (–)-camphanic acid chloride (11.9 g) in dichloromethane (24 g) was then added dropwise to the reaction mixture. Following stirring for 3 hours at a temperature of 10° C. or lower, pure water (64 g) was added, and following phase separation, the organic layer was collected. The organic layer was washed repeatedly with dilute aqueous hydrochloric acid and water, and was then concentrated under reduced pressure to yield PAG-B (23.0 g).

The thus obtained compound was analyzed using NMR, and the structure was identified on the basis of the following results.

$^{1}$H-NMR (400 MHz), DMSO-d6): δ (ppm)=7.76 to 7.90 (m, 12H, ArH), 2.62 to 2.69 (m, 1H, camphane), 2.08 to 2.26 (m, 8H, Ar—CH$_3$+camphane), 1.65 to 1.72 (m, 1H, camphane), 1.19 (s, 3H, CH$_3$), 1.09 (s, 3H, CH$_3$), 1.04 (s, 3H, CH$_3$).

Based on the results of the above analysis, the obtained compound PAG-B was confirmed as having the structure shown below.

[Chemical Formula 61]

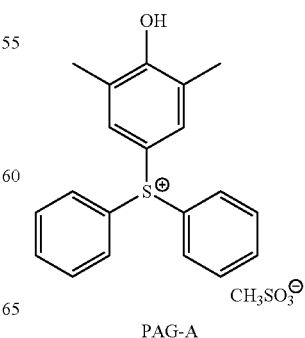

PAG-A

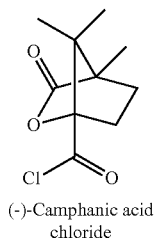

(-)-Camphanic acid chloride

→ TEA, CH₂Cl₂, < 10 deg. C., 3 h

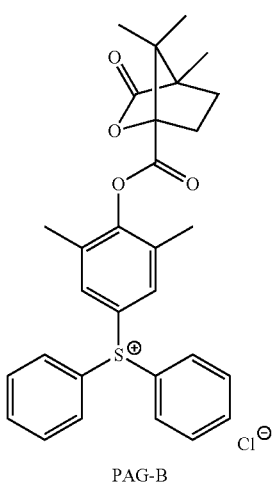

PAG-B

+ CH₃SO₃H

Synthesis Example 2

Synthesis of PAG-1

A round-bottom flask was charged with the PAG-B (5.3 g) obtained in the above Synthesis Example 1, an Anion-1 (4.4 g), dichloromethane (39.4 g) and pure water (21.5 g), and the resulting mixture was stirred for one hour at room temperature.

Subsequently, the dichloromethane layer was washed with 1% aqueous hydrochloric acid, and then washed repeatedly with pure water (20.0 g) until the wash water was neutral. The organic layer was then concentrated under reduced pressure, yielding 7.4 g of PAG-1 as a white solid.

The thus obtained compound was analyzed using NMR, and the structure was identified on the basis of the following results.

¹H-NMR (400 MHz), DMSO-d6): δ (ppm)=7.76 to 7.90 (m, 12H, ArH), 2.62 to 2.69 (m, 1H, camphane), 2.08 to 2.26 (m, 8H, Ar—CH₃+camphane), 1.65 to 1.72 (m, 1H, camphane), 1.19 (s, 3H, CH₃), 1.09 (s, 3H, CH₃), 1.04 (s, 3H, CH₃).

¹⁹F-NMR (376 MHz, DMSO-d6): δ (ppm)=−77.3, −111.5, −118.1, −122.4.

Based on the results of the above analysis, the obtained compound PAG-1 was confirmed as having the structure shown below.

[Chemical Formula 62]

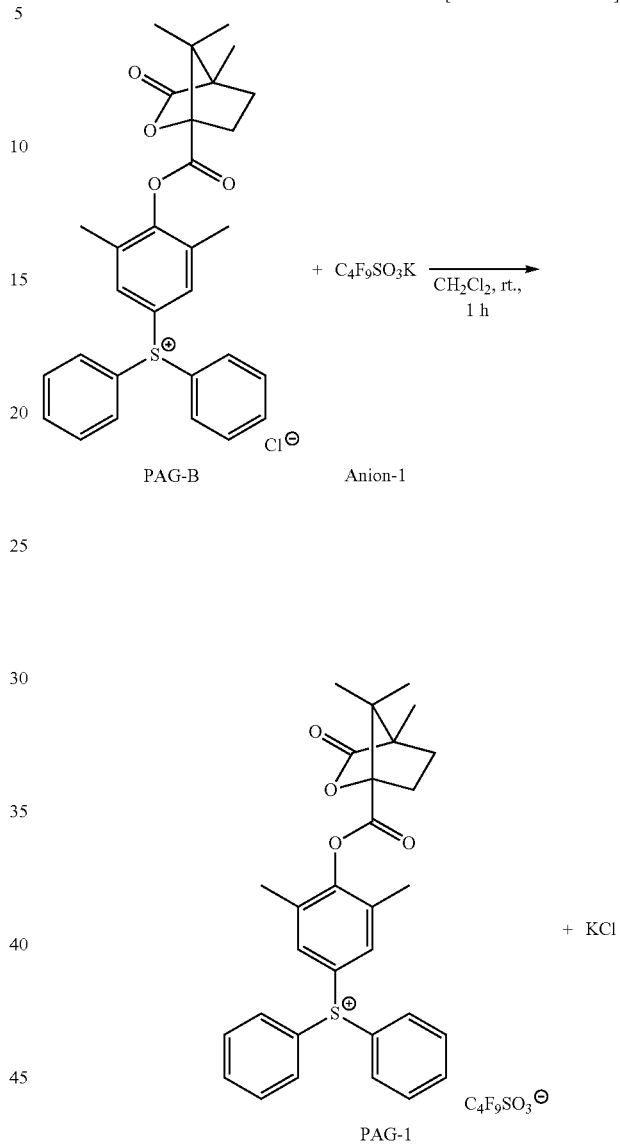

Synthesis Examples 3 to 33

Syntheses of PAG-2 to PAG-32

With the exception of replacing the Anion-1 with each of the compounds (M⁺-X⁻) (an equimolar amount) shown in Table 1 to Table 11 below, syntheses were performed in the same manner as Synthesis Example 1 described above. This yielded the compounds (products: PAG-2 to PAG-32) shown in Table 1 to Table 11.

Each compound (product) was analyzed by NMR, and the results of these analyses are also listed in Table 1 to Table 11.

TABLE 1

| Compound | NMR | Compound (M⁺ – X⁻) | Product |
|---|---|---|---|
| PAG-2 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3).<br>19F-NMR (376 MHz, DMSO-d6) : δ (ppm) = −75.0. | $CF_3SO_3^-\ K^+$ | |
| PAG-3 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3).<br>19F-NMR (376 MHz, DMSO-d6) : δ (ppm) = −77.3, −112.5, −121.7. | $C_3F_7SO_3^-\ K^+$ | |
| PAG-4 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3).<br>19F-NMR (376 MHz, DMSO-d6) : δ (ppm) = −116.9, −123.0. | | |

TABLE 2
| Compound | NMR | Compound (M⁺ – X⁻) | Product |
|---|---|---|---|
| PAG-5 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −75.9, −76.0, −114.7. | 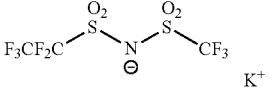 | 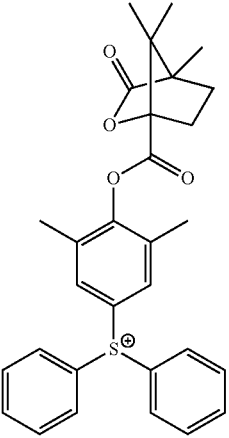 [SMILES: Cc1cc([S+](c2ccccc2)c2ccccc2)cc(C)c1OC(=O)C12CCC(C)(C(=O)O1)C2(C)C] |
| PAG-6 | 1H-NMR (400 MHz, DMSO-d6): δ (ppm) = 7.76-7.90 (m, 12H, ArH), 5.83-5.92(m, 1H, anion CH), 5.41(dd, 1H, anion CH), 5.21 (dd, 1H, anion CH), 4.45 (s, 2H, anion CH2) 2.62-2.69 (m, 1H, camphane), 2.08-2.26 (m, 8H, Ar—CH3 + camphane), 1.65-1.72(m, 1H, camphane), 1.19 (s, 3H, CH3), 1.09 (s, 3H, CH3), 1.04 (s, 3H, CH3). 19F-NMR (376 MHz, DMSO-d6): δ (ppm) = −80.0, −113.0 | 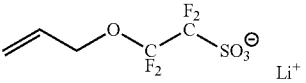 | 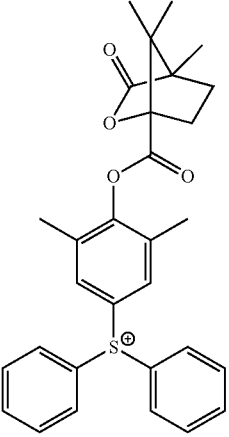 [SMILES: Cc1cc([S+](c2ccccc2)c2ccccc2)cc(C)c1OC(=O)C12CCC(C)(C(=O)O1)C2(C)C] |

TABLE 2-continued
| Compound | NMR | Compound (M⁺ – X⁻) | Product |
|---|---|---|---|
| PAG-7 | 1H-NMR (400 MHz, DMSO-d6): δ (ppm) = 7.76-7.90 (m, 12H, ArH), 4.40 (t, 2H, CH2), 4.21 (t, 2H, CH2), 2.62-2.69 (m, 1H, camphane), 2.08-2.26 (m, 8H, Ar—CH3 + camphane), 1.61-1.98 (m, 16H, camphane + adamantane), 1.19 (s, 3H, CH3), 1.09 (s, 3H, CH3), 1.04(s, 3H, CH3). 19F-NMR (376 MHz, DMSO-d6): δ (ppm) = −106.6. | 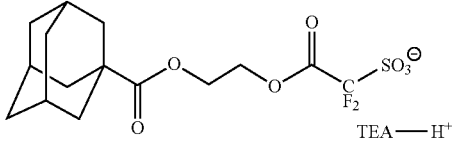 | 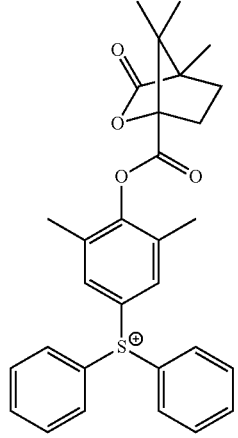 [SMILES: Cc1cc([S+](c2ccccc2)c2ccccc2)cc(C)c1OC(=O)C12CCC(C)(C(=O)O1)C2(C)C] |

TABLE 3
| Compound | NMR | Compound (M+ – X–) | Product |
|---|---|---|---|
| PAG-8 | 1H-NMR (400 MHz, DMSO-d6): δ (ppm) = 7.76-7.90 (m, 12H, ArH), 4.40-4.50 (m, 4H, CH2) 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −106.7, −154.0, −160.0, −161.5. | 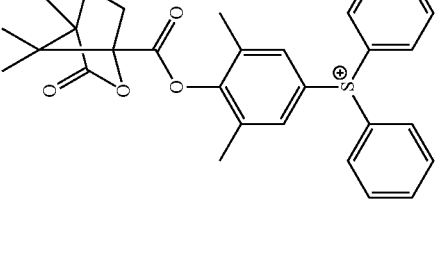 | 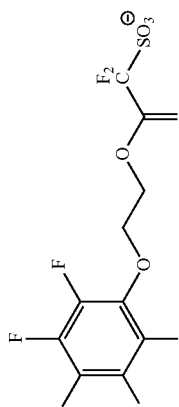 |

TABLE 3-continued
| Com- pound | NMR | Compound (M+ – X−) | Product |
|---|---|---|---|
| PAG-9 | 1H-NMR (400 MHz, DMSO-d6): δ (ppm) = 7.76-7.90 (m, 12H, ArH), 4.41 (t, 2H, CH2), 4.23 (t, 2H, CH2), 0.79-2.89 (m, 40H, Ar—CH3 + camphene + undecane). 19F-NMR (376 MHz, DMSO-d6): δ (ppm) = −106.8. | 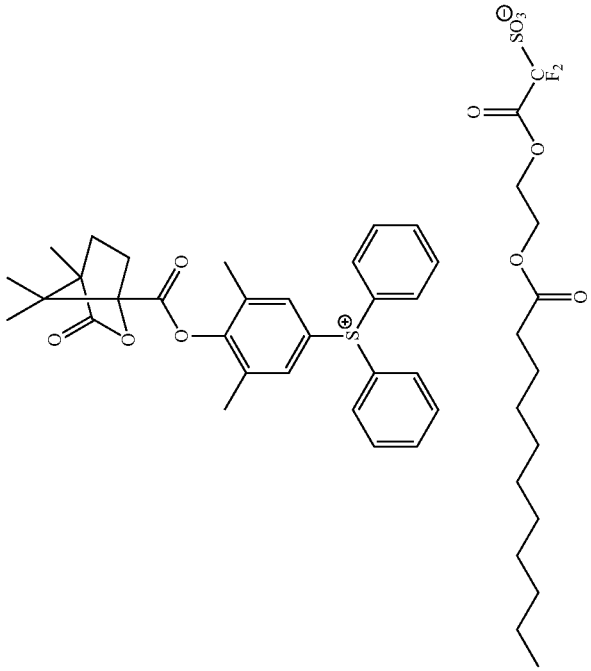<br>TEA—H+ | 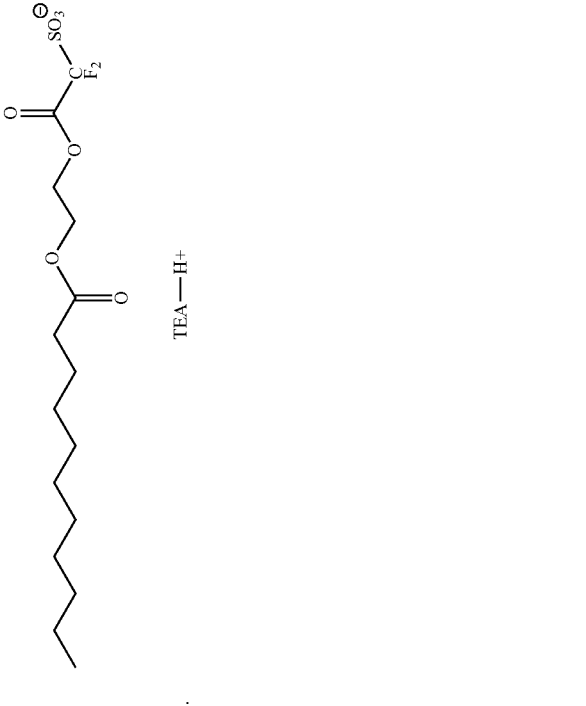 |

TABLE 3-continued

| Compound | | |
|---|---|---|
| Compound pound | NMR | Compound (M⁺−X⁻) | Product |
| PAG-10 | 1H-NMR (400 MHz, DMSO-d6); δ (ppm) = 7.76-7.90 (m, 1H, sultone), 4.78 (m, 12H, ArH), 4.66 (t, 1H, sultone), 3.88 (t, 1H, sultone), 3.34 (m, 1H, sultone), 2.62-2.69(m, 1H, camphane), 2.47-2.49 (m, 1H, sultone), 1.74-2.26 (m, 12H, Ar—CH3 + camphane + sultone), 1.65-1.72 (m, 1H, camphene), 1.19 (s, 3H, CH3), 1.09 (s, 3H, CH3), 1.04 (s, 3H, CH3). 19F-NMR (376 MHz, DMSO-d6); δ (ppm) = −107.7. | [structure with CF₂, SO₃⁻, Na⁺, sultone] | [sulfonium product structure] |

TABLE 4

| Compound | NMR | Compound (M⁺ – X⁻) | Product |
|---|---|---|---|
| PAG-11 | 1H-NMR (400 MHz, DMSO-d6): δ (ppm) = 8.74-8.82 (m, 2H, Py—H), 7.76-7.90 (m, 14H, Py—H + ArH), 4.54-4.61 (m, 4H, CH2CH2), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −106.5. | (isonicotinate-CH2CH2-O-CO-CF2-SO3⁻) TEA—H+ | (camphanyl ester of dimethylphenol-triphenylsulfonium with isonicotinate-CH2CH2-O-CO-CF2-SO3⁻) |
| PAG-12 | 1H-NMR (400 MHz, DMSO-d6): δ (ppm) = 7.76-7.90 (m, 12H, ArH), 5.46 (t, 1H, oxo-norbornane), 4.97 (s, 1H, oxo-norbornane), 4.71 (d, 1H, oxo-norbornane), 4.57 (d, 1H, oxo-norbornane), 2.62-2.73 (m, 2H, Camphane + oxo-norbornane), 2.06-2.26 (m, 10H, Ar—CH3 + camphane + oxo-norbornane), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −107.1. | (oxo-norbornane-O-CO-CF2-SO3⁻) Na⁺ | (camphanyl ester of dimethylphenol-triphenylsulfonium with oxo-norbornane-O-CO-CF2-SO3⁻) |

TABLE 4-continued

| Compound | NMR | Compound (M⁺ – X⁻) | Product |
|---|---|---|---|
| PAG-13 | 1H-NMR (400 MHz, DMSO-d6): δ (ppm) = 7.76-7.90 (m, 12H, ArH), 4.55 (t, 2H, CF2CH2), 2.62-2.69 (m, 1H, camphane), 2.08-2.26 (m, 8H, Ar—CH3 + camphane), 1.94 (m, 3H, Adamantane), 1.82 (m, 6H, Adamantane), 1.64-1.72 (m, 7H, camphene + Adamantane), 1.19(s, 3H, CH3), 1.09 (s, 3H, CH3), 1.04 (s, 3H, CH3). 19F-NMR (376 MHz, DMSO-d6): δ (ppm) = −111.2. | 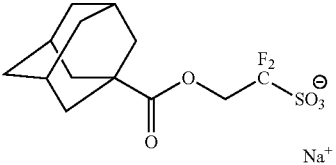 | 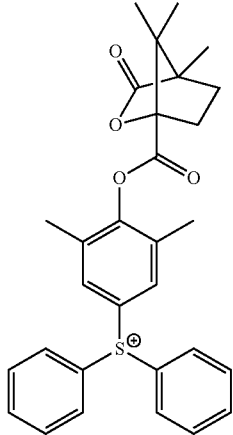 [SMILES: Cc1cc([S+](c2ccccc2)c2ccccc2)cc(C)c1OC(=O)C12CCC(C)(C(=O)O1)C2(C)C] |

TABLE 5

| Compound | NMR | Compound (M⁺ – X⁻) | Product |
|---|---|---|---|
| PAG-14 | 1H-NMR (400 MHz, DMSO~d6): δ (ppm) = 7.76-7.90 (m, 12H, ArH), 4.40 (t, 2H, CH2), 4.20 (t, 2H, CH2), 2.62-2.69 (m, 1H, camphane), 2.08-2.26 (m, 8H, Ar—CH3 + camphane), 2.05 (s, 2H, CH2), 1.53-1.95 (m, 16H, camphene + Adamantane), 1.19 (s, 3H, CH3), 1.09 (s, 3H, CH3), 1.04 (s, 3H, CH3). 19F-NMR (376 MHz, DMSO-d6): δ (ppm) = −111.2. | 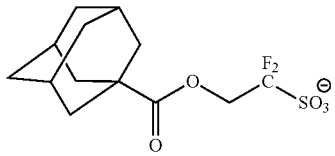 | 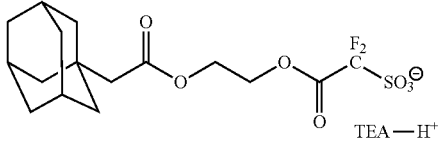 |

TABLE 5-continued
| Compound | NMR | Compound (M⁺ – X⁻) | Product |
|---|---|---|---|
| PAG-15 | 1H-NMR (400 MHz, DMSO-d6): δ (ppm) = 7.76-7.90 (m, 12H, ArH), 4.19 (s, 2H, CH2), 2.62-2.69 (m, 1H, camphane), 2.08-2.26 (m, 8H, Ar—CH3 + camphane), 1.55-1.87 (m, 16H, camphene + Adamantane), 1.19 (s, 3H, CH3), 1.09 (s, 3H, CH3), 1.04 (s, 3H, CH3). 19F-NMR (376 MHz, DMSO-d6): δ (ppm) = −77.7. | 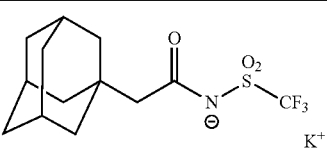 | 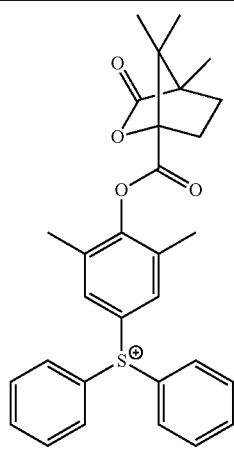 |
| PAG-16 | 1H-NMR (400 MHz, DMSO-d6): δ (ppm) = 7.76-7.90 (m, 12H, ArH), 2.77-2.81 (m, 1H, Cyclohexyl), 2.62-2.69 (m, 1H, camphane), 2.09-2.26 (m, 8H, Ar—CH3 + camphane), 2.04-2.07 (m, 2H, Cyclohexyl), 1.73-1.75 (m, 2H, Cyclohexyl), 1.56-1.72 (m, 2H, camphane + Cyclohexyl), 1.07-1.33 (s, 11H, CH3 + Cyclohexyl), 1.04 (s, 3H, CH3). 19F-NMR (376 MHz, DMSO-d6): δ (ppm) = −74.7 | 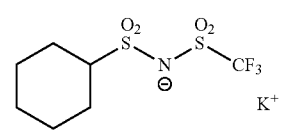 [SMILES: O=S(=O)([N-]S(=O)(=O)C(F)(F)F)C1CCCCC1 ; [K+]] | 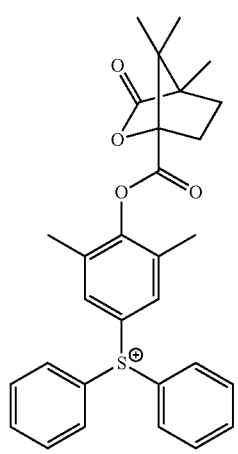 [SMILES: Cc1cc([S+](c2ccccc2)c2ccccc2)cc(C)c1OC(=O)C12CCC(C)(C(=O)O1)C2(C)C] |

TABLE 6
| Compound | NMR | Compound (M⁺ – X⁻) | Product |
|---|---|---|---|
| PAG-17 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.55-1.88(m, 16H, camphane + Adamantane), 1.19 (s, 3H, CH3), 1.09 (s, 3H, CH3), 1.04 (s, 3H, CH3). 19F-NMR (376 MHz, DMSO-d6): δ (ppm) = −74.5. | 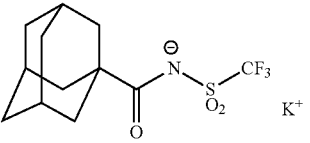 [SMILES: O=C([N-]S(=O)(=O)C(F)(F)F)C12CC3CC(CC(C3)C1)C2 ; [K+]] | 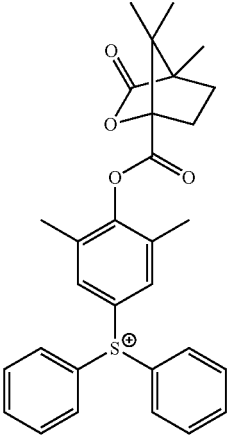 [SMILES: Cc1cc([S+](c2ccccc2)c2ccccc2)cc(C)c1OC(=O)C12CCC(C)(C(=O)O1)C2(C)C] 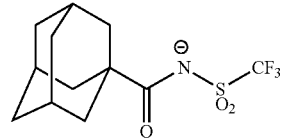 [SMILES: O=C([N-]S(=O)(=O)C(F)(F)F)C12CC3CC(CC(C3)C1)C2] |
| PAG-18 | 1H-NMR (400 MHz, DMSO-d6): δ (ppm) = 7.76-7.90 (m, 12H, ArH), 2.62-2.69 (m, 1H, camphane), 2.08-2.26 (m, 11H, Ar—CH3 + camphane + Adamantane), 1.59-1.99 (m, 13H, camphane + Adamantane), 1.19 (s, 3H, CH3), 1.09 (s, 3H, CH3), 1.04 (s, 3H, CH3). 19F-NMR (376 MHz, DMSO-d6): δ (ppm) = −69.2, −76.0, −112.9. | 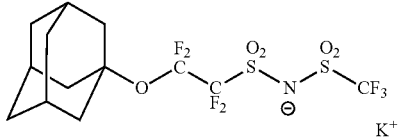 [SMILES: O=S(=O)([N-]S(=O)(=O)C(F)(F)C(F)(F)OC12CC3CC(CC(C3)C1)C2)C(F)(F)F ; [K+]] | 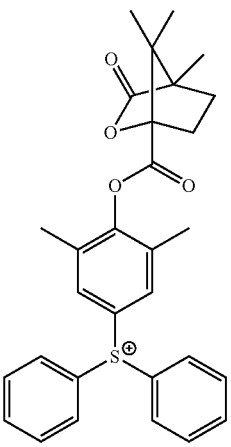 [SMILES: Cc1cc([S+](c2ccccc2)c2ccccc2)cc(C)c1OC(=O)C12CCC(C)(C(=O)O1)C2(C)C] 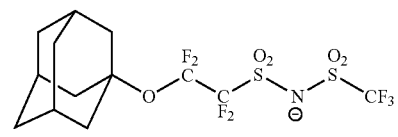 [SMILES: O=S(=O)([N-]S(=O)(=O)C(F)(F)C(F)(F)OC12CC3CC(CC(C3)C1)C2)C(F)(F)F] |

TABLE 6-continued
| Compound | NMR | Compound (M⁺ – X⁻) | Product |
|---|---|---|---|
| PAG-19 | 1H-NMR (400 MHz, DMSO-d6): δ (ppm) = 7.51-7.96 (m, 19H, ArH + Naph-H), 5.20 (s, 2H, CH2), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −80.5, 113.7. | 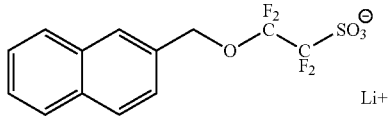 | 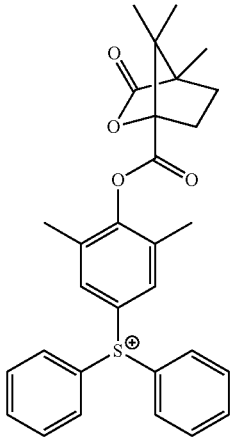 [SMILES: Cc1cc([S+](c2ccccc2)c2ccccc2)cc(C)c1OC(=O)C12CCC(C)(C(=O)O1)C2(C)C] |
TABLE 7
| Compound | NMR | Compound (M⁺ – X⁻) | Product |
|---|---|---|---|
| PAG-20 | 1H-NMR (400 MHz, DMSO-d6): δ (ppm) = 7.76-7.90 (m, 12H, ArH), 2.62-2.69 (m, 1H, camphane), 2.08-2.26 (m, 6H, Ar—CH3 + camphene + Adamantane), 1.56-1.96 (m, 13H, camphene + Adamantane), 1.19 (s, 3H, CH3), 1.09 (s, 3H, CH3), 1.04 (s, 3H, CH3). 19F-NMR (376 MHz, DMSO-d6): δ (ppm) = −70.1, −113.4. | 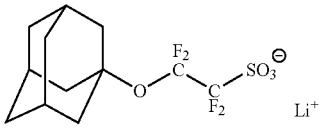 | 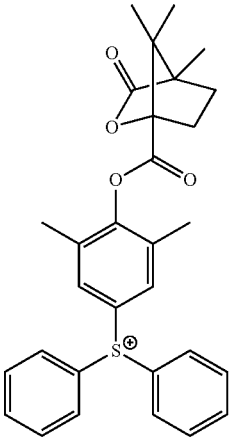 [SMILES: Cc1cc([S+](c2ccccc2)c2ccccc2)cc(C)c1OC(=O)C12CCC(C)(C(=O)O1)C2(C)C] 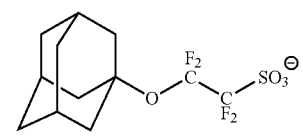 |

TABLE 7-continued
| Compound | NMR | Compound (M⁺ – X⁻) | Product |
|---|---|---|---|
| PAG-21 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, GH3).<br>19F-NMR (376 MHz, DMSO-d6): δ (ppm) = −73.7. | 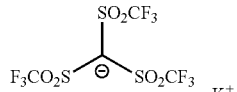 | 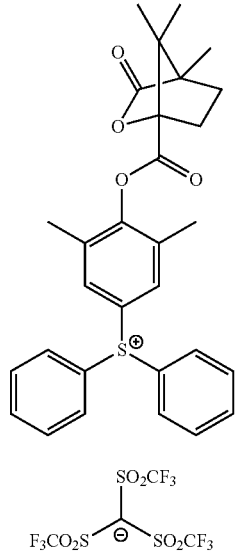 |
| PAG-22 | 1H-NMR (400 MHz, DMSO-d6): δ (ppm) = 7.76-7.90 (m, 12H, ArH), 2.62-2.69 (m, 1H, camphane), 2.08-2.26 (m, 8H, Ar—CH3 + camphane), 1.65-1.72 (m, 1H, camphane), 1.19 (s, 3H, CH3), 1.09 (s, 3H, CH3), 1.04 (s, 3H, CH3).<br>19F-NMR (376 MHz, DMSO-d6): δ (ppm) = −161.1, −149.7, −131.6, −76.2. | 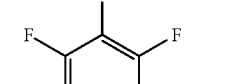 | 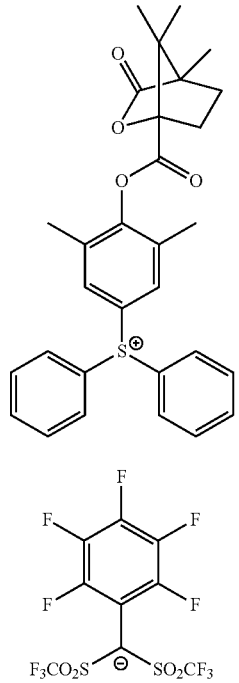 |

TABLE 8
| Compound | NMR | Compound (M⁺ – X⁻) | Product |
|---|---|---|---|
| PAG-23 | 1H-NMR (400 MHz, DMSO-d6): δ (ppm) = 7.76-7.90 (m, 12H, ArH), 2.88 (d, 1H, CH), 2.66-2.74 (m, 1H, CH), 2.62-2.69 (m, 1H, camphane), 2.37 (d, 1H, CH), 2.08-2.26 (m, 9H, Ar—CH3 + camphane + CH), 1.90 (t, 1H, CH), 1.74-1.89 (m, 2H, CH2), 1.65-1.72 (m, 1H, camphane), 1.22-1.29 (m, 2H, CH2), 1.19 (s, 3H, CH3), 1.09 (s, 3H, CH3), 1.04 (s, 3H, CH3), 1.03 (s, 3H, CH3), 0.71 (s, 3H, CH3). | 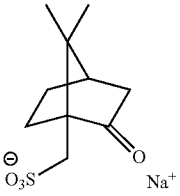 | 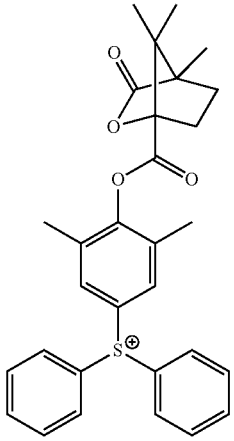 [SMILES: Cc1cc([S+](c2ccccc2)c2ccccc2)cc(C)c1OC(=O)C12CCC(C)(C(=O)O1)C2(C)C] |
| PAG-24 | 1H-NMR (400 MHz, DMSO-d6): δ (ppm) = 7.76-7.90 (m, 12H, ArH), 4.49-4.51(m, 2H, O—CH2), 4.30-4.32(m, 2H, O—CH2), 2.62-2.69 (m, 1H, camphane), 2.31(t, 2H, CO—CH2), 2.08-2.26 (m, 8H, Ar—CH3 + camphane), 1.65-1.72 (m, 1H, camphane), 1.51-1.56(m, 2H, CH2), 1.15-1.35 (m, 9H, CH3 + CH2), 1.09 (s, 3H, CH3), 1.04 (s, 3H, CH3), 0.87 (t, 3H, CH3). 19F-NMR (376 MHz, DMSO-d6): δ (ppm) = −106.7. | 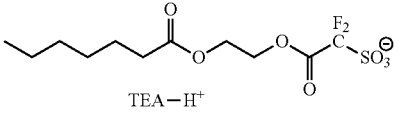 | 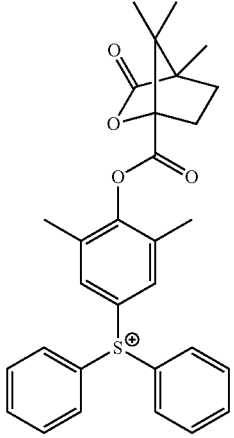 [SMILES: Cc1cc([S+](c2ccccc2)c2ccccc2)cc(C)c1OC(=O)C12CCC(C)(C(=O)O1)C2(C)C] |

TABLE 8-continued

| Compound | NMR | Compound (M⁺ – X⁻) | Product |
|---|---|---|---|
| PAG-25 | 1H-NMR (400 MHz, DMSO-d6): δ (ppm) = 7.76-7.90 (m, 12H, ArH), 4.50-4.54 (m, 4H, OCH2CH2O), 3.57(d, 1H, CH2SO2), 3.36 (sd, 1H, CH2SO2), 2.62-2.69 (m, 1H, camphane), 2.27-2.34 (m, 2H, camphor), 2.08-2.26 (m, 8H, Ar—CH3 + camphane), 2.07 (t, 1H, camphor), 1.92-1.99 (m, 2H, camphor), 1.65-1.72 (m, 1H, camphane), 1.56-1.62 (m, 1H, camphor), 1.42-1.45 (m, 1H, camphor), 1.19 (s, 3H, CH3), 1.09 (s, 3H, CH3), 1.04 (m, 6H, CH3), 0.84 (s, 3H, CH3). 19F-NMR (376 MHz, DMSO-d6): δ (ppm) = –106.5. | 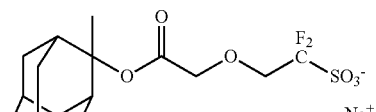 | |

TABLE 9

| Compound | NMR | Compound (M⁺ – X⁻) | Product |
|---|---|---|---|
| PAG-26 | 1H-NMR (400 MHz, DMSO-d6): δ (ppm) = 7.76-7.90 (m, 12H, ArH), 4.22 (s, 2H, CH2O), 4.05 (t, 2H, CH2CF2), 2.62-2.69 (m, 1H, camphane), 2.08-2.26 (m, 10H, Ar—CH3 + camphene + Adamantane ), 1.53-1.99 (m, 16H, camphane + Adamantane + CH3), 1.19 (s, 3H, CH3), 1.09 (s, 3H, CH3), 1.04 (s, 3H, CH3). 19F-NMR (376 MHz, DMSO-d6): δ (ppm) = –111.0. | 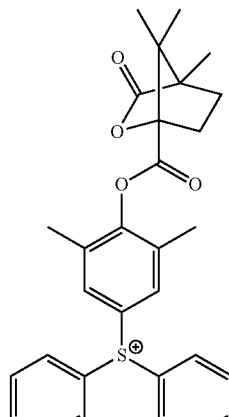 | |

TABLE 9-continued
| Compound | NMR | Compound (M⁺ – X⁻) | Product |
|---|---|---|---|
| PAG-27 | 1H-NMR (400 MHz, DMSO-d6): δ (ppm) = 7.76-7.90 (m, 12H, ArH), 4.84 (ddd, 1H, CH2O), 4.68 (ddd, 1H, CH2O), 2.62-2.69 (m, 1H, camphane), 2.38-2.45 (m, 1H, camphanic), 2.08-2.26 (m, 8H, Ar—CH3 + camphane), 1.93-2.06 (m, 2H, camphanic), 1.65-1.72 (m, 1H, camphane), 1.55-1.61 (m, 1H, camphanic), 1.19 (s, 3H, CH3), 1.09 (s, 3H, CH3), 1.04 (m, 6H, CH3), 1.03 (s, 3H, CH3), 0.85 (s, 3H, CH3). 19F-NMR (376 MHz, DMSO-d6): δ (ppm) = −111.0. | 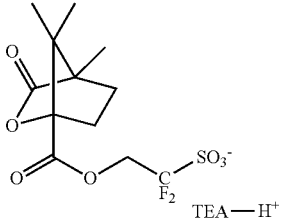 | 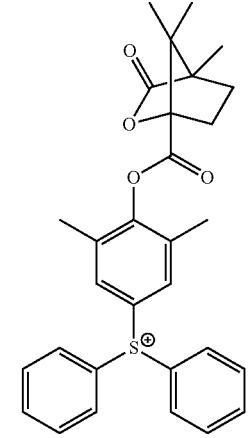 [SMILES: Cc1cc([S+](c2ccccc2)c2ccccc2)cc(C)c1OC(=O)C12CCC(C)(C(=O)O1)C2(C)C] |
| PAG-28 | 1H-NMR (400 MHz, DMSO-d6): δ (ppm) = 7.76-7.90 (m, 12H, ArH), 5.02 (s, 1H, CH), 4.21(s, 1H, CH), 2.93 (s, 1H, CH), 2.62-2.69 (m, 1H, camphene), 1.41-2.29 (m, 19H, Hyperlactone + Ar—CH3 + camphane), 1.19 (s, 3H, CH3), 1.09 (s, 3H, CH3), 1.04 (s, 3H, CH3). 19F-NMR (376 MHz, DMSO-d6): δ (ppm) = −107.3. | 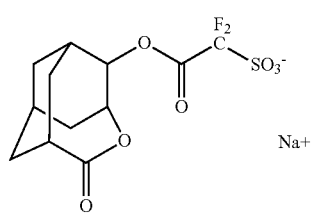 | 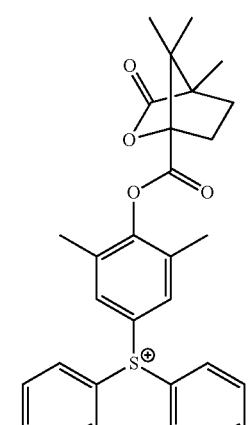 |

TABLE 10
| Compound | NMR | Compound (M⁺ – X⁻) | Product |
|---|---|---|---|
| PAG-29 | 1H-NMR (400 MHz, DMSO-d6): δ (ppm) = 7.76-7.90 (m, 12H, ArH), 6.01(s, 1H, C=CH), 5.62(s, 1H, C=CH), 3.95-4.00 (t, 2H, CH2), 3.09-3.15 (t, 2H, CH2), 2.62-2.69 (m, 1H, camphane), 2.08-2.26 (m, 8H, Ar—CH3 + camphane), 1.83 (s, 3H, CH3), 1.65-1.72 (m, 1H, camphane), 1.19 (s, 3H, CH3), 1.09 (s, 3H, CH3), 1.04 (s, 3H, CH3). 19F-NMR (376 MHz, DMSO-d6): δ (ppm) = −76.0. | 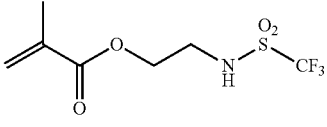 [SMILES: C=C(C)C(=O)OCCNS(=O)(=O)C(F)(F)F] | 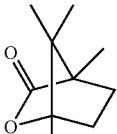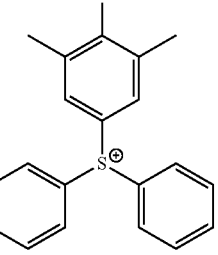 |
| PAG-30 | 1H-NMR (400 MHz, DMSO-d6): δ (ppm) = 7.76-7.90 (m, 12H, ArH), 4.39-4.60 (m, 4H, OCH2CH2O), 2.62-2.69 (m, 1H, camphane), 2.36-2.53 (m, 1H, Camphane), 2.08-2.26 (m, 8H, Ar—CH3 + camphane), 1.88-2.03 (m, 2H, Camphane), 1.65-1.72 (m, 1H, camphane), 1.47-1.62 (m, 1H, Camphane), 1.19 (s, 3H, CH3), 0.81-1.11 (m, 15H, CH3) 19F-NMR (376 MHz, DMSO-d6): δ (ppm) = −106.6. | 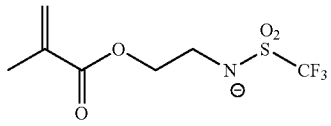 [SMILES: C=C(C)C(=O)OCC[N-]S(=O)(=O)C(F)(F)F] TEA—H⁺ | 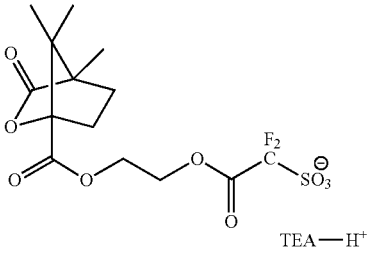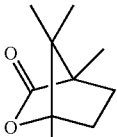 |

TABLE 10-continued

| Compound | NMR | Compound (M⁺ – X⁻) | Product |
|---|---|---|---|
| PAG-31 | 1H-NMR (400 MHz, DMSO-d6): δ (ppm) = 7.76-7.90 (m, 12H, ArH), 5.21 (m, 1H, CFH), 4.82(m, 1H, OCH2), 4.57 (m, 1H, OCH2), 2.62-2.69 (m, 1H, camphane), 2.51 (m, 1H, Camphane), 2.08-2.26 (m, 8H, Ar—CH3 + camphane), 2.03 (m, 2H, Camphane), 1.65-1.72 (m, 1H, camphane), 1.19 (s, 3H, CH3), 1.59 (m, 1H, Camphane), 1.10 (m, 9H, CH3), 1.04 (s, 3H, CH3), 0.85 (s, 3H, CH3). 19F-NMR (376 MHz, DMSO-d6): δ (ppm) = –108.6, –116.5, –204.2. | 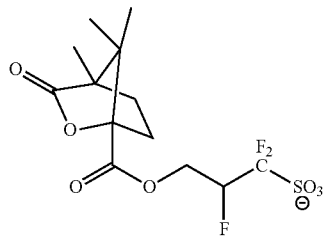 | 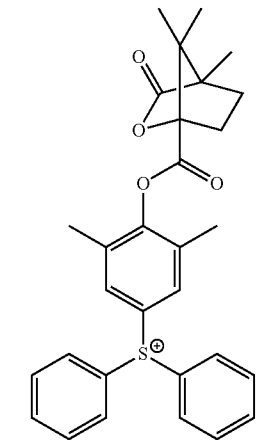 [SMILES: Cc1cc([S+](c2ccccc2)c2ccccc2)cc(C)c1OC(=O)C12CCC(C)(C(=O)O1)C2(C)C] |

TABLE 11

| Compound | NMR | Compound (M⁺ – X⁻) | Product |
|---|---|---|---|
| PAG-32 | 1H-NMR (400 MHz, DMSO-d6): δ (ppm) = 7.76-7.90 (m, 12H, ArH), 6.22 (m, 1H, CH=CH), 6.07 (m, 1H, CH=CH), 4.76 (m, 1H, sultone), 4.65-4.34 (m, 3H, CF2CH2 + sultone), 3.87 (m, 1H, sultone), 3.58-3.38 (m, 3H, CHC=O + sultone), 3.11 (m, 2H, Norbornene), 2.62-2.69 (m, 1H, camphane), 2.37 (m, 1H, sultone), 2.08-2.26 (m, 9H, Ar—CH3 + camphane + sultone), 1.65-1.89 (m, 4H, camphane + sultone), 1.19 (s, 3H, CH3), 1.09 (s, 3H, cH3), 1.44-1.21 (m, 2H, Norbornene), 1.04 (s, 3H, CH3). 19F-NMR (376 MHz, DMSO-d6): δ (ppm) = –118.5~–118.9. | 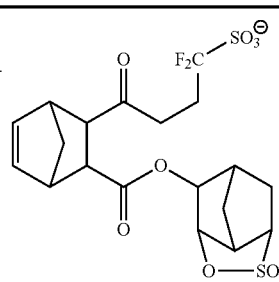 | 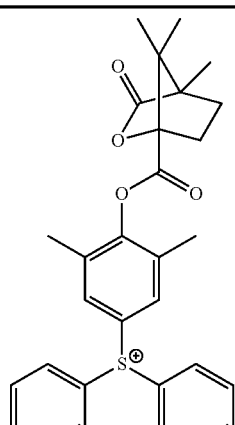 |

Examples 1 to 20, Comparative Examples 1 to 4

The components shown in Tables 12 and 13 were mixed together and dissolved to prepare a series of positive resist compositions.

TABLE 12

|  | Component (A) | Component (B) | Component (D) | Component (E) | Component (S) | |
|---|---|---|---|---|---|---|
| Comparative Example 1 | (A)-1 [100] | (B)-A [8.00] | — | (D)-1 [1.2] | (E)-1 [1.32] | (S)-1 [10.0] | (S)-2 [2557] |
| Comparative Example 2 | (A)-2 [100] | (B)-A [8.00] | — | (D)-1 [1.2] | (E)-1 [1.32] | (S)-1 [10.0] | (S)-2 [2557] |
| Comparative Example 3 | (A)-1 [100] | (B)-B [10.67] | — | (D)-1 [1.2] | (E)-1 [1.32] | (S)-1 [10.0] | (S)-2 [2557] |
| Comparative Example 4 | (A)-2 [100] | (B)-B [10.67] | — | (D)-1 [1.2] | (E)-1 [1.32] | (S)-1 [10.0] | (S)-2 [2557] |
| Example 1 | (A)-1 [100] | (B)-1 [11.59] | — | (D)-1 [1.2] | (E)-1 [1.32] | (S)-1 [10.0] | (S)-2 [2557] |
| Example 2 | (A)-1 [100] | (B)-2 [11.25] | — | (D)-1 [1.2] | (E)-1 [1.32] | (S)-1 [10.0] | (S)-2 [2557] |
| Example 3 | (A)-1 [100] | (B)-3 [12.06] | — | (D)-1 [1.2] | (E)-1 [1.32] | (S)-1 [10.0] | (S)-2 [2557] |
| Example 4 | (A)-1 [100] | (B)-4 [11.11] | — | (D)-1 [1.2] | (E)-1 [1.32] | (S)-1 [10.0] | (S)-2 [2557] |
| Example 5 | (A)-1 [100] | (B)-5 [11.48] | — | (D)-1 [1.2] | (E)-1 [1.32] | (S)-1 [10.0] | (S)-2 [2557] |
| Example 6 | (A)-1 [100] | (B)-6 [12.14] | — | (D)-1 [1.2] | (E)-1 [1.32] | (S)-1 [10.0] | (S)-2 [2557] |
| Example 7 | (A)-1 [100] | (B)-7 [13.67] | — | (D)-1 [1.2] | (E)-1 [1.32] | (S)-1 [10.0] | (S)-2 [2557] |
| Example 8 | (A)-1 [100] | (B)-8 [10.92] | — | (D)-1 [1.2] | (E)-1 [1.32] | (S)-1 [10.0] | (S)-2 [2557] |
| Example 9 | (A)-1 [100] | (B)-9 [10.95] | — | (D)-1 [1.2] | (E)-1 [1.32] | (S)-1 [10.0] | (S)-2 [2557] |
| Example 10 | (A)-1 [100] | (B)-10 [10.95] | — | (D)-1 [1.2] | (E)-1 [1.32] | (S)-1 [10.0] | (S)-2 [2557] |
| Example 11 | (A)-1 [100] | (B)-11 [13.18] | — | (D)-1 [1.2] | (E)-1 [1.32] | (S)-1 [10.0] | (S)-2 [2557] |

TABLE 13

|  | Component (A) | Component (B) | | Component (D) | Component (E) | Component (S) | |
|---|---|---|---|---|---|---|---|
| Example 12 | (A)-1 [100] | (B)-1 [11.59] | (B)-12 [2.61] | — | (E)-1 [1.32] | (S)-1 [10.0] | (S)-2 [2557] |
| Example 13 | (A)-1 [100] | (B)-1 [11.59] | (B)-12 [3.79] | (D)-1 [1.2] | (E)-1 [1.32] | (S)-1 [10.0] | (S)-2 [2557] |
| Example 14 | (A)-2 [100] | (B)-5 [11.48] | — | (D)-1 [1.2] | (E)-1 [1.32] | (S)-1 [10.0] | (S)-2 [2557] |
| Example 15 | (A)-2 [100] | (B)-8 [10.92] | — | (D)-1 [1.2] | (E)-1 [1.32] | (S)-1 [10.0] | (S)-2 [2557] |
| Example 16 | (A)-1 [100] | (B)-1 [11.59] | (B)-13 [3.79] | — | (E)-1 [1.32] | (S)-1 [10.0] | (S)-2 [2557] |
| Example 17 | (A)-1 [100] | (B)-1 [11.59] | (B)-13 [5.51] | (D)-1 [1.2] | (E)-1 [1.32] | (S)-1 [10.0] | (S)-2 [2557] |
| Example 18 | (A)-1 [100] | (B)-1 [11.59] | (B)-14 [3.10] | — | (E)-1 [1.32] | (S)-1 [10.0] | (S)-2 [2557] |
| Example 19 | (A)-1 [100] | (B)-1 [11.59] | (B)-15 [2.40] | — | (E)-1 [1.32] | (S)-1 [10.0] | (S)-2 [2557] |
| Example 20 | (A)-1 [100] | (B)-1 [11.59] | (B)-16 [2.76] | — | (E)-1 [1.32] | (S)-1 [10.0] | (S)-2 [2557] |

In Tables 12 and 13, the reference symbols have the meanings shown below. Further, the numerical values in brackets [ ] indicate the amount (in parts by weight) of the component added.

(A)-1: the polymeric compound (A)-1 shown below.
(A)-2: the polymeric compound (A)-2 shown below.
(B)-A: the compound (B)-A shown below.
(B)-B: the compound (B)-B shown below.
(B)-1: the compound PAG-10 described above.
(B)-2: the compound PAG-13 described above.
(B)-3: the compound PAG-14 described above.
(B)-4: the compound PAG-12 described above.
(B)-5: the compound PAG-28 described above.
(B)-6: the compound PAG-9 described above.
(B)-7: the compound PAG-32 described above.
(B)-8: the compound PAG-1 described above.
(B)-9: the compound PAG-4 described above.
(B)-10: the compound PAG-18 described above.
(B)-11: the compound PAG-21 described above.
(B)-12: the compound (B)-12 shown below.
(B)-13: the compound PAG-23 described above.
(B)-14: the compound (B)-14 shown below.
(B)-15: the compound (B)-15 shown below.
(B)-16: the compound (B)-16 shown below.
(D)-1: tri-n-pentylamine (E)-1: salicylic acid
(S)-1: γ-butyrolactone
(S)-2: a mixed solvent of PGMEA/PGME/cyclohexanone=45/35/20 (weight ratio)

[Chemical Formula 63]

(A)-1

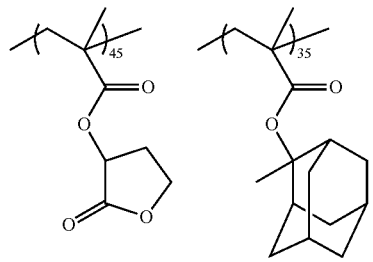

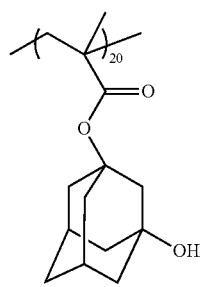

[Mw=7,000, Mw/Mn=1.70, wherein the subscript numerals shown to the bottom right of the parentheses ( ) indicate the copolymer composition ratio (molar ratio).]

[Chemical Formula 64]

(A)-2

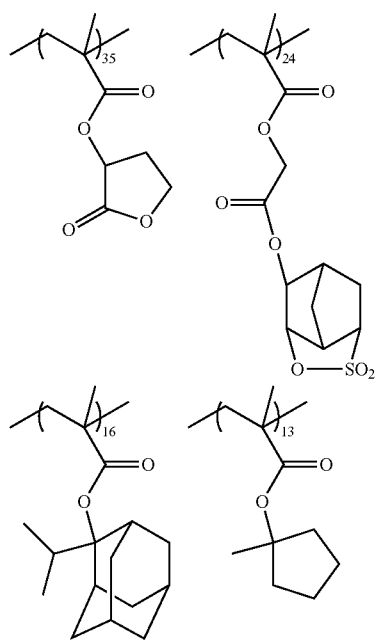

-continued

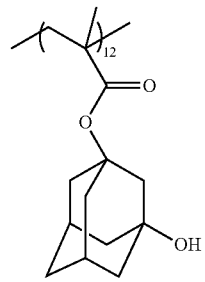

[Mw=7,900, Mw/Mn=1.56, wherein the subscript numerals shown to the bottom right of the parentheses ( ) indicate the copolymer composition ratio (molar ratio).]

[Chemical Formula 65]

(B)-A

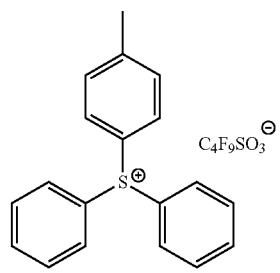

(B)-B (B)-12

(B)-14

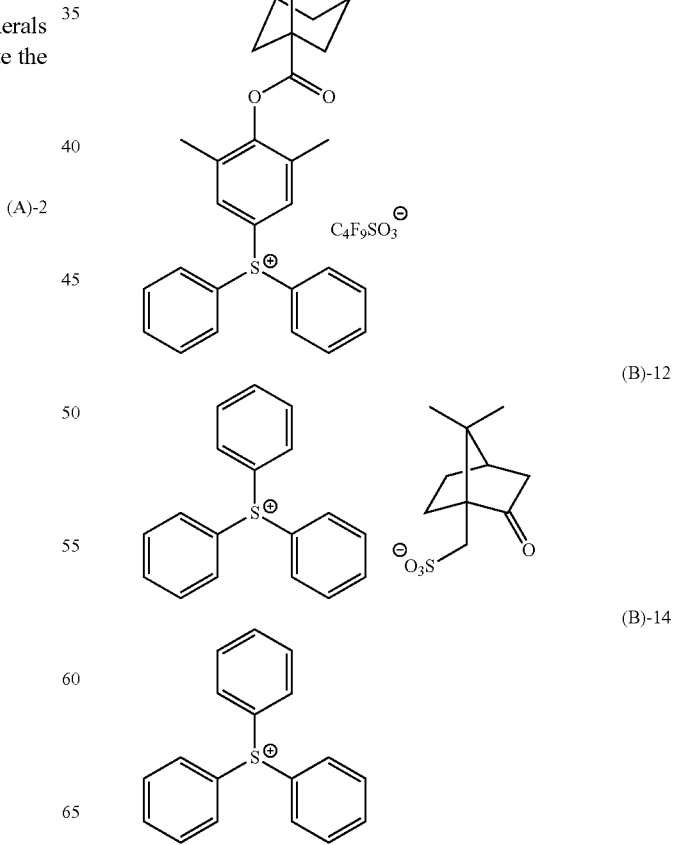

-continued

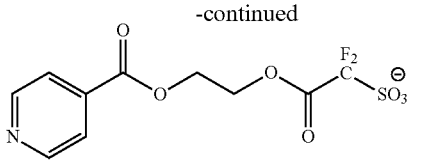
(B)-15

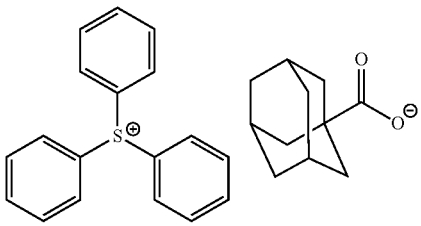
(B)-16

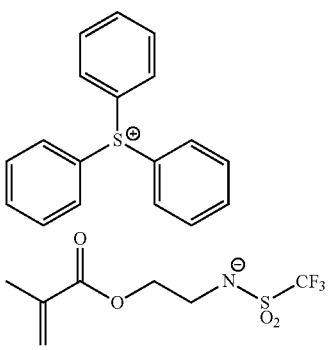

Using the obtained positive resist compositions, resist patterns were formed using the procedure described below, and each of the resist patterns was then evaluated in the manner described below.

[Formation of Resist Pattern]

An organic anti-reflection film composition ARC29A (a product name, manufactured by Brewer Science Ltd.) was applied onto an 8-inch silicon wafer using a spinner, and the composition was then baked and dried on a hot plate at 205° C. for 60 seconds, thereby forming an organic anti-reflection film having a thickness of 82 nm. Each of the resist compositions obtained above was applied onto this type of anti-reflection film using a spinner, and was then prebaked (PAB) on a hot plate at a temperature indicated in Table 14 for 60 seconds and dried, thereby forming a resist film having a thickness of 150 nm.

Subsequently, using an ArF exposure apparatus NSR-5302 (manufactured by Nikon Corporation, NA (numerical aperture)=0.60, 2/3 annular illumination), the resist film was selectively irradiated with an ArF excimer laser (193 nm) through a mask pattern (6% half-tone mask). Next, a post exposure bake (PEB) treatment was conducted at a temperature indicated in Table 14 for 60 seconds, and the resist film was then developed for 30 seconds at 23° C. in a 2.38% by weight aqueous solution of tetramethylammonium hydroxide (TMAH) NMD-3 (manufactured by Tokyo Ohka Kogyo Co., Ltd.). The resist film was then rinsed for 30 seconds with pure water, and shaken dry.

As a result, in each of the examples, a line and space (1:1) resist pattern (LS pattern) having a line width of 120 nm and a pitch of 240 nm was formed in the resist film. The optimum exposure dose Eop (mJ/cm$^2$) for formation of the LS pattern, namely the sensitivity, was determined. The results are shown in Table 14.

[Evaluation of LWR (Line Width Roughness)]

For each of the LS patterns having a line width of 120 nm and a pitch of 240 nm formed at the above-mentioned Eop value, the space width was measured at 400 points along the lengthwise direction of the space using a measuring scanning electron microscope (SEM) (scanning electron microscope, accelerating voltage: 800 V, product name: S-9220, manufactured by Hitachi, Ltd.), and from these results, the value of 3 times the standard deviation (s) (namely, 3s) was determined. The average value of 3s across 400 locations was calculated as an indicator of the LWR. The results are shown in Table 14.

The smaller the value of 3s, the lower the level of roughness in the line width, indicating an LS pattern of more uniform width.

[Evaluation of MEEF]

Using the same procedure as that described above for formation of the resist pattern, and at the above-mentioned Eop, LS patterns were formed using a mask pattern targeting an LS pattern having a line width of 120 nm and a pitch of 260 nm and a mask pattern targeting an LS pattern having a line width of 130 nm and a pitch of 260 nm. The value of the MEEF was then determined using the formula shown below. The results are shown in Table 14.

$$MEEF = |CD_{130} - CD_{120}|/|MD_{130} - MD_{120}|$$

In this formula, $CD_{130}$ and $CD_{120}$ represent the respective line widths (nm) of the actual LS patterns formed using the mask pattern targeting a line width of 130 nm and the mask pattern targeting a line width of 120 nm respectively, and $MD_{130}$ and $MD_{120}$ represent the respective target line widths (nm) of the mask patterns, meaning $MD_{130} = 130$ and $MD_{120} = 120$.

The closer the MEEF value is to 1, the more faithful the formed resist pattern is to the mask pattern.

[Evaluation of Exposure Margin (EL Margin)]

The exposure dose at which an LS pattern having a line width within a range specified by: [targeted dimension (line width of 120 nm)±5%] (namely, within a range from 114 nm to 126 nm) was formed was determined, and the EL margin (unit: %) was determined using the formula shown below. The results are shown in Table 14.

$$EL\ margin\ (\%) = (|E1 - E2|/Eop) \times 100$$

In the formula, E1 represents the exposure dose (mJ/cm$^2$) for forming an LS pattern with a space width of 114 nm, and E2 represents the exposure dose (mJ/cm$^2$) for forming an LS pattern with a space width of 126 nm.

The larger the value for the EL margin, the smaller the variation in the pattern size caused by fluctuation in the exposure dose.

TABLE 14

| | PAB (° C.) | PEB (° C.) | Eop (mJ/cm$^2$) | LWR (nm) | MEEF | EL (±5%) |
|---|---|---|---|---|---|---|
| Comparative Example 1 | 110 | 110 | 25.8 | 12.7 | 3.11 | 4.80 |
| Comparative Example 2 | 90 | 90 | 28.4 | 12.5 | 3.09 | 4.94 |
| Comparative Example 3 | 110 | 110 | 39.5 | 12.4 | 3.08 | 4.85 |
| Comparative Example 4 | 90 | 90 | 42.1 | 12.2 | 3.04 | 5.09 |
| Example 1 | 110 | 110 | 46.8 | 11.6 | 3.01 | 5.98 |
| Example 2 | 110 | 110 | 43.4 | 12.1 | 2.25 | 6.01 |
| Example 3 | 110 | 110 | 42.9 | 11.8 | 2.56 | 5.87 |
| Example 4 | 110 | 110 | 42.8 | 11.7 | 2.64 | 5.68 |
| Example 5 | 110 | 110 | 49.4 | 11.1 | 1.92 | 6.69 |
| Example 6 | 110 | 110 | 40.6 | 11.6 | 2.78 | 6.14 |

TABLE 14-continued

| | PAB (° C.) | PEB (° C.) | Eop (mJ/cm$^2$) | LWR (nm) | MEEF | EL (±5%) |
|---|---|---|---|---|---|---|
| Example 7 | 110 | 110 | 40.2 | 11.8 | 2.71 | 6.09 |
| Example 8 | 110 | 110 | 41.0 | 11.9 | 2.87 | 6.04 |
| Example 9 | 110 | 110 | 42.3 | 12.0 | 2.93 | 5.97 |
| Example 10 | 110 | 110 | 47.5 | 11.8 | 2.95 | 5.97 |
| Example 11 | 110 | 110 | 45.1 | 12.1 | 2.79 | 5.78 |
| Example 12 | 110 | 110 | 40.5 | 12.1 | 2.89 | 5.59 |
| Example 13 | 110 | 110 | 45.8 | 11.9 | 2.96 | 5.55 |
| Example 14 | 90 | 90 | 51.9 | 10.8 | 1.88 | 5.51 |
| Example 15 | 90 | 90 | 42.8 | 11.4 | 2.62 | 6.00 |
| Example 16 | 110 | 110 | 43.9 | 11.7 | 2.78 | 5.73 |
| Example 17 | 110 | 110 | 48.6 | 11.4 | 2.81 | 5.67 |
| Example 18 | 110 | 110 | 45.7 | 12.1 | 2.94 | 5.38 |
| Example 19 | 110 | 110 | 40.8 | 11.9 | 2.80 | 5.91 |
| Example 20 | 110 | 110 | 46.1 | 12.0 | 2.76 | 5.64 |

The above results in Table 14 confirmed that, compared with the resist compositions of Comparative Examples 1 to 4, the resist compositions of Examples 1 to 20 exhibited superior lithography properties such as LWR, MEEF and EL margin.

What is claimed is:

1. A resist composition, comprising a base component (A) which exhibits changed solubility in a developing solution under action of acid, and an acid generator component (B) which generates acid upon exposure, wherein
the acid generator component (B) comprises an acid generator (B1) having a group represented by general formula (b1-2) shown below:

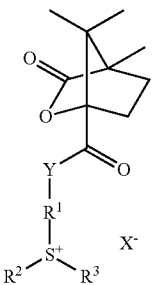

(b1-2)

wherein Y represents a divalent linking group, R$^1$ represents an arylene group which may have a substituent, each of R$^2$ and R$^3$ independently represents an organic group, R$^2$ and R$^3$ may be bonded to each other to form a ring with a sulfur atom in the formula, and X$^-$ represents a counter anion.

2. The resist composition according to claim 1, wherein the base component (A) is a base component (A0) that exhibits increased polarity under action of acid.

3. The resist composition according to claim 2, wherein the base component (A0) is a resin component (A1) having a structural unit (a1), which is derived from an acrylate ester that may have an atom other than a hydrogen atom or a substituent bonded to a carbon atom on an α-position, and comprises an acid-degradable group that exhibits increased polarity under action of acid.

4. The resist composition according to claim 3, wherein the resin component (A1) further comprises at least one structural unit (a2) selected from the group consisting of structural units derived from an acrylate ester which comprises an —SO$_2$-containing cyclic group and may have an atom other than a hydrogen atom or a substituent bonded to a carbon atom on an α-position, and structural units derived from an acrylate ester which comprises a lactone-containing cyclic group and may have an atom other than a hydrogen atom or a substituent bonded to a carbon atom on an α-position.

5. The resist composition according to claim 3, wherein the resin component (A1) further comprises a structural unit (a3) derived from an acrylate ester which contains a polar group-containing aliphatic hydrocarbon group and may have an atom other than a hydrogen atom or a substituent bonded to a carbon atom on an α-position.

6. The resist composition according to claim 1, further comprising a nitrogen-containing organic compound (D).

7. A method of forming a resist pattern, the method comprising: forming a resist film on a substrate using the resist composition according to any one of claims 1 to 6, conducting exposure of the resist film, and developing the resist film to form a resist pattern.

8. A compound represented by general formula (b1-2) shown below:

[Chemical Formula 3]

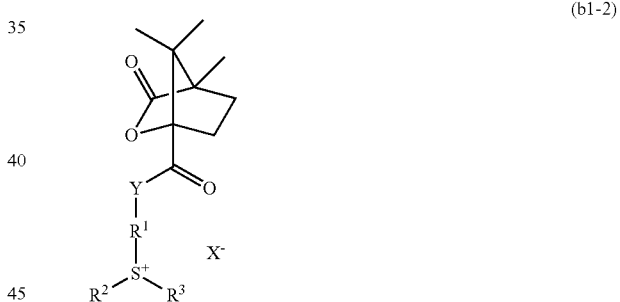

(b1-2)

wherein Y represents a divalent linking group, R$^1$ represents an arylene group which may have a substituent, each of R$^2$ and R$^3$ independently represents an organic group, R$^2$ and R$^3$ may be bonded to each other to form a ring with a sulfur atom in the formula, and X$^-$ represents a counter anion.

9. An acid generator, comprising the compound according to claim 8.

* * * * *